US012793816B2

(12) United States Patent
Wilson et al.

(10) Patent No.: US 12,793,816 B2
(45) Date of Patent: Nov. 10, 2026

(54) SIMULATING CLINICAL TRIALS USING WHOLE BODY DIGITAL TWIN TECHNOLOGY

(71) Applicant: Twin Health, Inc., Mountain View, CA (US)

(72) Inventors: James Wilson, Sunnyvale, CA (US); Abhik Banerjee, Milpitas, CA (US); Terrence Chun Yin Poon, Foster City, CA (US); Jahangir Mohammed, Mountain View, CA (US)

(73) Assignee: Twin Health, Inc., Mountain View, CA (US)

( * ) Notice: Subject to any disclaimer, the term of this patent is extended or adjusted under 35 U.S.C. 154(b) by 976 days.

(21) Appl. No.: 17/963,928

(22) Filed: Oct. 11, 2022

(65) Prior Publication Data

US 2023/0111605 A1 Apr. 13, 2023

Related U.S. Application Data

(60) Provisional application No. 63/254,491, filed on Oct. 11, 2021.

(51) Int. Cl.
*G16H 10/20* (2018.01)
*G06N 5/022* (2023.01)
(Continued)

(52) U.S. Cl.
CPC ............. *G16H 10/20* (2018.01); *G06N 5/022* (2013.01); *G06N 5/04* (2013.01); *G16H 10/60* (2018.01);
(Continued)

(58) Field of Classification Search
CPC ........ G16H 10/20; G16H 10/60; G16H 20/00; G16H 40/67; G16H 50/20; G16H 50/70; G06N 5/022; G06N 5/04
See application file for complete search history.

(56) References Cited

U.S. PATENT DOCUMENTS

2018/0075194 A1* 3/2018 Allen .................... G16H 70/20
2019/0252079 A1 8/2019 Constantin et al.
(Continued)

OTHER PUBLICATIONS

Sinisi, Stefano, et al. "Optimal personalised treatment computation through in silico clinical trials on patient digital twins." arXiv preprint arXiv:2106.10684 (2021). (Year: 2021).*
(Continued)

*Primary Examiner* — Kevin W Figueroa
*Assistant Examiner* — Victor Adelard Nault
(74) *Attorney, Agent, or Firm* — FENWICK & WEST LLP

(57) ABSTRACT

A Digital Twin clinical trial simulator generates a plurality of candidate treatments for causing a target improvement in metabolic health. Each candidate treatment comprises one or more intervention parameters and instructions for adjusting the one or more intervention parameters of the one or more intervention parameters to cause the target improvement. For each candidate treatment, the Digital Twin clinical trial simulator identifies a cohort of patients sensitive to adjustments to the one or more intervention parameters. The Digital Twin clinical trial simulator inputs the candidate treatment to patient-specific metabolic models, which predict the effectiveness of the candidate treatment for each patient of the cohort. The Digital Twin clinical trial simulator identifies a shortlist of effective treatments based on the predictions of the patient-specific metabolic models and generates instructions for performing physical experiments to validate the effectiveness of each shortlisted candidate treatment.

21 Claims, 17 Drawing Sheets

(51) Int. Cl.

| | |
|---|---|
| ***G06N 5/04*** | (2023.01) |
| ***G16H 10/60*** | (2018.01) |
| ***G16H 20/00*** | (2018.01) |
| ***G16H 40/67*** | (2018.01) |
| ***G16H 50/20*** | (2018.01) |
| ***G16H 50/70*** | (2018.01) |

(52) U.S. Cl.

CPC ............. *G16H 20/00* (2018.01); *G16H 40/67* (2018.01); *G16H 50/20* (2018.01); *G16H 50/70* (2018.01)

(56) References Cited

U.S. PATENT DOCUMENTS

| | | | | |
|---|---|---|---|---|
| 2020/0411141 | A1 | 12/2020 | Foster et al. | |
| 2021/0045694 | A1 | 2/2021 | Hadley et al. | |
| 2021/0202103 | A1* | 7/2021 | Bostic | G16H 50/80 |
| 2021/0219910 | A1 | 7/2021 | Mohammed et al. | |
| 2021/0241116 | A1* | 8/2021 | Bulut | A61B 5/4824 |
| 2021/0319887 | A1 | 10/2021 | Derrick et al. | |
| 2022/0044826 | A1 | 2/2022 | Schaeffer et al. | |
| 2022/0076841 | A1* | 3/2022 | Abu El Ata | G16H 10/40 |
| 2022/0102010 | A1* | 3/2022 | Hendriks | A61B 5/6898 |
| 2022/0157413 | A1* | 5/2022 | Fisher | G16H 20/10 |
| 2022/0392609 | A1 | 12/2022 | Hadad et al. | |
| 2025/0166794 | A1* | 5/2025 | Ceballos Lentini | G06T 7/0012 |

OTHER PUBLICATIONS

Shamanna, Paramesh, et al. "Reducing HbA1c in type 2 diabetes using digital twin technology-enabled precision nutrition: a retrospective analysis." Diabetes Therapy 11.11 (2020): 2703-2714. (Year: 2020).*

Barbiero, Pietro, Ramon Vinas Torne, and Pietro Lio. "Graph representation forecasting of patient's medical conditions: toward a digital twin." Frontiers in genetics 12 (2021): 652907. (Year: 2021).*

International Search Report and Written Opinion, Patent Cooperation Treaty Application No. PCT/US2022/046322, Mar. 27, 2023, 17 pages.

United States Office Action, U.S. Appl. No. 17/963,933, Feb. 5, 2026, 19 pages.

United States Office Action, U.S. Appl. No. 17/963,932, Mar. 10, 2025, 42 pages.

United States Office Action, U.S. Appl. No. 17/963,932, Oct. 27, 2025, 35 pages.

* cited by examiner

200

SIMULATING CLINICAL TRIALS USING WHOLE BODY DIGITAL TWIN TECHNOLOGY

CROSS REFERENCE TO RELATED APPLICATIONS

This application claims the benefit of U.S. Provisional Patent Application No. 63/254,491, filed on Oct. 11, 2021, which is incorporated by reference herein in its entirety for all purposes

BACKGROUND

Field of Art

The disclosure relates generally to a patient health management platform, and more specifically, to a patient health management platform for simulating clinical trials for candidate metabolic treatment recommendations using digital representations of metabolic states for population of patients.

Description of the Related Art

Conventional medicine relies on clinical trials to validate medical treatments. Because such clinical trials are often expensive, time-intensive, and labor-intensive, the number of clinical trials that can be run during a given time period is limited. This is particularly challenging for lifestyle interventions such as improvements in nutrition, physical activity, sleep, and meditative breathing, because each intervention is highly complex with an extremely large number of possible treatments (e.g., a large number of possible nutrition plans based on a combination of many different foods, quantities, timings, etc.). Further complicating the problem, attempts to personalize these nutrition plans are inhibited by an insufficient amount of data or by an insufficient number of similar patients to perform a trial that would yield a significant result. Due to these issues, the results of clinical trials are often averaged across the trial population instead of being tailored towards individual patients. Further, the effectiveness of the trial may be affected by variations in physiological and medical conditions across the tested populations.

Additionally, given the amount of time that lifestyle interventions take to affect the metabolism of a patient, clinical trials may take years and an excess of financial funding. As a result, traditional approaches to validating medical treatments often result in effective lifestyle treatments being disregarded because of the high resource cost for completing a clinical trial.

SUMMARY

A Digital Twin clinical trial simulator simulates various aspects of clinical trials using digital models of individuals that each capture the biology of the individual's body (e.g., a whole body digital twin or WBDT). The models are generated using an array of inputs, such as biomarkers from sensors (e.g., wearable sensors), parameters taken from laboratory or other testing (e.g., blood tests), symptoms and other information reported by a user, medications reported to be consumed by the user, etc., and that outputs. Using these digital models that act as representatives or twins of individuals, the Digital Twin clinical trial simulator effectively has a population of patients for whom it can perform various clinical trial simulations with a substantial savings in time, expense, and labor relative to what is typically required with conventional clinical trials where live tests are performed on actual patients. The Digital Twin clinical trial simulator can test a large number of scenarios without the negative consequences to patients that clinical trials sometimes entail. In addition, it allows for analysis across more controlled populations and has access to a larger population of patients and substantially more data than is possible in a conventional clinical trial, ultimately providing a more accurate and tailored result.

In one embodiment, the Digital Twin clinical trial stimulator generates a pool of candidate treatments for effecting a target improvement in health (e.g., metabolic health). Each candidate treatment provides instructions for adjusting a distinct combination of one or more intervention parameters. Intervention parameters refer to the various aspects of patient data known to affect metabolic health, for example micronutrients, macronutrients, biota nutrients, lifestyle data, physical activity routines, and sleep habits.

For each candidate treatment, the Digital Twin clinical trial simulator identifies a cohort of sensitive patients based on a likelihood that the candidate treatment will affect the patient's metabolic health. Described differently, patients in the identified cohort are determined to have the strongest correlation between the intervention parameter(s) adjusted by the candidate treatment and their own metabolic health.

The Digital Twin clinical trial simulator inputs a feature vector representation of each candidate treatment recommendation to patient-specific metabolic models of each patient in the cohort to generate a prediction of whether the candidate treatment will affect the metabolic health of the patient to achieve the target improvement. Accordingly, the Digital Twin clinical trial simulator predicts the efficacy of each candidate treatment. The Digital Twin clinical trial simulator may additionally identify new intervention parameters or new features of metabolic health by extracting novel correlations between the metabolic profiles of patients in the identified cohort and intervention parameters identified in effective or ineffective candidate treatments. The Digital Twin clinical trial simulator may additionally identify features of metabolic health where the Digital Twin clinical trial simulator lacks sufficient data for patient-specific metabolic models to generate accurate predictions. For such features, the Digital Twin clinical trial simulator may supplement the data with synthetically generated data and validate the candidate treatment using the supplemented data.

Based on the predicted effectiveness of each candidate treatment, the Digital Twin clinical trial simulator identifies a shortlist of the most effective candidate treatments for further evaluation by physical experiments. The shortlist of candidate treatments may additionally be generated based on the accuracy of the predictions and the confidence intervals of the predictions. The Digital Twin clinical trial simulator may additionally define instructions/procedures and additional insight for performing the physical experiments.

In one embodiment, the clinical trial simulator generates a plurality of candidate treatment recommendations for causing a target improvement in metabolic state. Each candidate treatment recommendation comprises one or more intervention parameters and instructions for adjusting the one or more intervention parameters to cause the target improvement. For each of the candidate treatment recommendations, the Digital Twin clinical trial simulator identifies a cohort of patients from a population of patients. Each patient of the cohort is sensitive to adjustments to the one or more intervention parameters. For each patient of the cohort of patients, the Digital Twin clinical trial simulator predicts effects of the candidate treatment recommendation on a metabolic state of the patient by inputting the candidate treatment recommendation to a digital twin of the patient. The Digital Twin clinical trial simulator identifies a shortlist of one or more effective treatments based on the effects predicted by the plurality of patient-specific metabolic models of the digital twin for the pin. The Digital Twin clinical trial simulator displays the shortlist of candidate treatment recommendations to a patient or medical provider via an application on a computing device.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

A patient health management platform simulates clinical trials using digital twin technology and machine-learned models to predict the metabolic health impacts of various types of treatment interventions. For example, the platform can generate and test candidate treatment recommendations, such as nutritional interventions for improving a metabolic state. By simulating the clinical trials using personalized digital twins generated for patients of a particular type, the patient health management platform validates candidate treatment recommendation in a far shorter period of time than traditional, exploratory clinical trials.

As will be discussed below, a patient's digital twin is a digital model capturing the biology and metabolism of the patient's body. The digital twin models a patient's metabolic health based on a combination of inputs including biosignals measured by wearable sensors, during lab tests, symptoms reported by the patients, medicines consumed by the patients, food consumed by the patients, and lifestyle decisions (including activity and sleep behaviors) made by the patients. A patient's digital twin generates predictions of the patient's metabolic state based on relationships between aspects of a patient's health and various factors known to affect metabolic health.

The results of the simulated clinical trials are additionally personalized to individual patients or types of patients. Based on the personalized effectiveness of each candidate treatment, the Digital Twin clinical trial simulator can perform various analyses relevant for clinical trials, such as identifying a shortlist of treatments that can be further validated using physical experiments. The Digital Twin clinical trial simulator additionally generates definitions and procedures for each of the shortlisted experiments.

Figure 1:
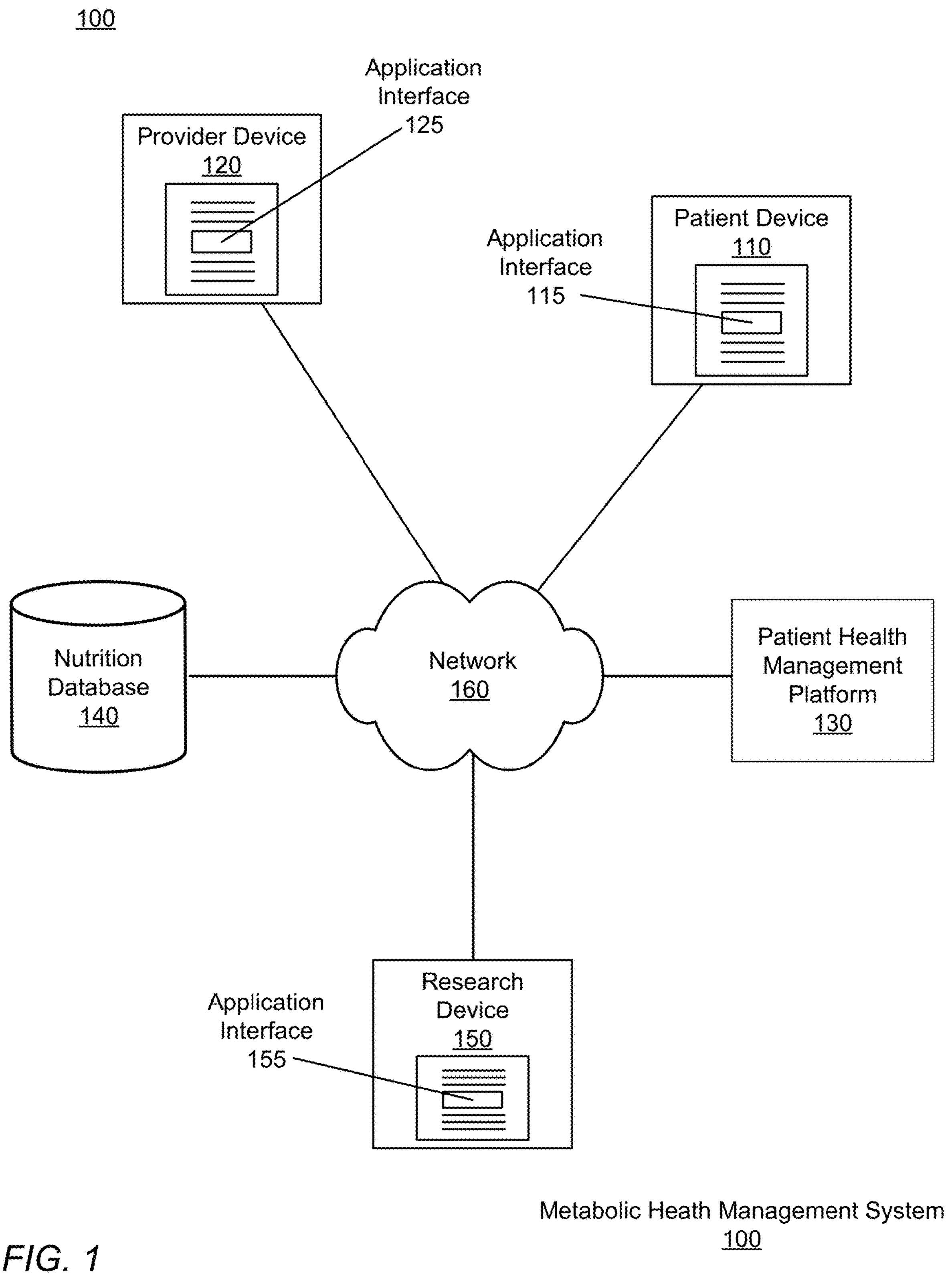
FIG. 1 shows a metabolic health manager for monitoring metabolic health of a patient, performing analytics on the metabolic health data, and providing a patient-specific recommendation for treating metabolic health-related concerns, according to one embodiment.

FIG. 1 shows a metabolic health manager 100 for monitoring a patient's metabolic health, for performing analytics on metabolic health data recorded for the patient, and for generating a patient-specific recommendation for treating any metabolic health-related concerns, according to one embodiment. The metabolic health manager 100 includes patient device(s) 110, provider device(s) 120, a patient health management platform 130, a nutrition database 140, research device(s) 150 and a network 160. However, in other embodiments, the system 100 may include different and/or additional components. For example, the patient device 110 can represent thousands or millions of devices for patients (e.g., patient mobile devices) that interact with the system in locations around the world. Similarly, the provider device 120 can represent thousands or millions of devices of providers (e.g., mobile phones, laptop computers, in-provider-office recording devices, etc.). In some cases, a single provider may have more than one device that interacts with the platform 130.

The patient device 110 is a computing device with data processing and data communication capabilities that is capable of receiving inputs from a patient. An example physical implementation is described more completely below with respect to FIG. 2. In addition to data processing, the patient device 110 may include functionality that allows the device 110 to record speech responses articulated by a patient operating the device (e.g., a microphone), and to graphically present data to a patient (e.g., a graphics display). Examples of the patient device 110 include desktop computers, laptop computers, portable computers, GOOGLE HOME, AMAZON ECHO, etc. The patient device 110 may present information generated by the communication platform 130 via a mobile application configured to display and record patient responses. For example, through a software application interface 115, a patient may receive a recommendation or an update regarding their metabolic health.

Application 115 provides a user interface (herein referred to as a "patient dashboard") that is displayed on a screen of the patient device 110 and allows a patient to input commands to control the operation of the application 115. The patient dashboard enables patients to track and manage changes in a patient's metabolic health. For example, the dashboard allows patients to observe changes in their metabolic health over time, receive recommendation notifications, exchange messages about treatment with a health care provider, and so on. The application 115 may be coded as a web page, series of web pages, or content otherwise coded to render within an internet browser. The application 115 may also be coded as a proprietary application configured to operate on the native operating system of the patient device 110. In addition to providing the dashboard, application 115 may also perform some data processing on biological and food data locally using the resources of patient device 110 before sending the processed data through the network 150. Patient data sent through the network 150 is received by the patient health management platform 130 where it is analyzed and processed for storage and retrieval in conjunction with a database.

Similarly, a provider device 120 is a computing device with data processing and data communication capabilities that is capable of receiving input from a provider. The provider device 120 is configured to present a patient's medical history or medically relevant data (i.e., a display screen). The above description of the functionality of the patient device 110 also can apply to the provider device 120. The provider device 120 can be a personal device (e.g., phone, tablet) of the provider, a medical institution computer (e.g., a desktop computer of a hospital or medical facility), etc. In addition, the provider device 120 can include a device that sits within the provider office such that the patient can interact with the device inside the office. In such implementations, the provider device is a customized device with audio and/or video capabilities (e.g., a microphone for recording, a display screen for text and/or video, an interactive user interface, a network interface, etc.). The provider device 120 may also present information to medical providers or healthcare organizations via a mobile application similar to the application described with reference to patient device 110.

Application 125 provides a user interface (herein referred to as a "provider dashboard") that is displayed on a screen of the provider device 120 and allows a medical provider or trained professional/coach to input commands to control the operation of the application 125. The provider dashboard enables providers to track and manage changes in a patient's metabolic health. The application 125 may be coded as a web page, series of web pages, or content otherwise coded to render within an internet browser. The application 125 may also be coded as a proprietary application configured to operate on the native operating system of the patient device 110.

The patient health management platform 130 is a medium for dynamically generating recommendations for improving a patient's metabolic health based on biological data recorded from a plurality of sources including wearable sensors (or other types of IoT sensors), lab tests, etc., and food or diet-related data recorded by the patient. The patient health management platform 130 predicts a patient's metabolic response based on periodically recorded patient data (e.g., nutrition data, symptom data, lifestyle data). Accordingly, a patient's metabolic response describes a change in metabolic health for a patient resulting from the food they most recently consumed and their current metabolic health. Based on such a change, the platform 130 generates a recommendation including instructions for a patient to improve their metabolic health or to maintain their improved metabolic health. Additionally, in real-time or near real-time, the patient health management platform 130 may provide feedback to a patient identifying potential inconsistencies or errors in the food or biological data entered manually by the patient based on a comparison of the patient's true metabolic state and their predicted metabolic state.

The nutrition database 140 stores nutrition data extracted from a collection of nutrient sources, for example food or vitamins. Data within the nutrition database 140 may be populated using data recorded by a combination of public sources and third-party entities such as the USDA, research programs, or affiliated restaurants. The stored data may include, but is not limited to, nutrition information (for example, calories, macromolecule measurements, vitamin concentrations, cholesterol measurements, or other facts) for individual foods or types of foods and relationships between foods and metabolic responses (for example, an impact of a given food on insulin sensitivity). Data stored in the nutrition database 140 may be applicable to an entire population (i.e., general nutrition information) or personalized to an individual patient (i.e., a personalized layer of the nutrition database). For example, the nutrition database 140 may store information describing a patient's particular biological (i.e., metabolic) response to a food. In such embodiments, the nutrition database 140 may be updated based on feedback from the patient health management platform 140.

In some embodiments, for example the embodiment illustrated in FIG. 1, the analytics system 100 additionally comprises a research device 150 that analyzes information generated by the patient health management platform to analyze a patient's metabolic response. For example, the research device 150 may receive a patient's current metabolic state, their previous metabolic state, and a treatment recommendation that contributed to the current metabolic state. By continuously comparing current metabolic state and the previous metabolic state, the research device 150 may evaluate the effectiveness of the treatment recommendation as a whole. Alternatively, the research device 150 may evaluate the effectiveness of certain aspects of the treatment recommendation. The research device 150 is a computing device capable of receiving input from a provider with data processing and data communication capabilities. The research device 150 is configured to present a patient's medical history or medically relevant data (i.e., a display screen). The above description of the functionality of the patient device 110 and the provider device 120 also can apply to the research device 150. The research device 150 can be a personal device (e.g., phone, tablet) of the provider, a medical institution computer (e.g., a desktop computer of a hospital or medical facility), etc. In addition, the provider device 150 can include a device that sits within the research office such that a patient can interact with the device inside the office. In such implementations, the research device 150 is a customized device with audio and/or video capabilities (e.g., a microphone for recording, a display screen for text and/or video, an interactive user interface, a network interface, etc.). The research device 150 may also present information to a research team via a mobile application similar to the application described with reference to patient device 110.

Application 155 provides a user interface (herein referred to as a "research dashboard") that is displayed on a screen of the research device 150 and allows a researcher to input commands to control the operation of the application 155. The research dashboard enables providers to track and manage changes in a patient's metabolic health. The application 155 may be coded as a web page, series of web pages, or content otherwise coded to render within an internet browser. The application 155 may also be coded as a proprietary application configured to operate on the native operating system of the patient device 110.

Interactions between the patient device 110, the provider device 120, the patient health management platform 130, and the nutrition database 140 are typically performed via the network 150, which enables communication between the patient device 120, the provider device 130, and the patient communication platform 130. In one embodiment, the network 150 uses standard communication technologies and/or protocols including, but not limited to, links using technologies such as Ethernet, 802.11, worldwide interoperability for microwave access (WiMAX), 3G, 4G, LTE, digital subscriber line (DSL), asynchronous transfer mode (ATM), InfiniBand, and PCI Express Advanced Switching. The network 150 may also utilize dedicated, custom, or private communication links. The network 150 may comprise any combination of local area and/or wide area networks, using both wired and wireless communication systems.

Figure 2:
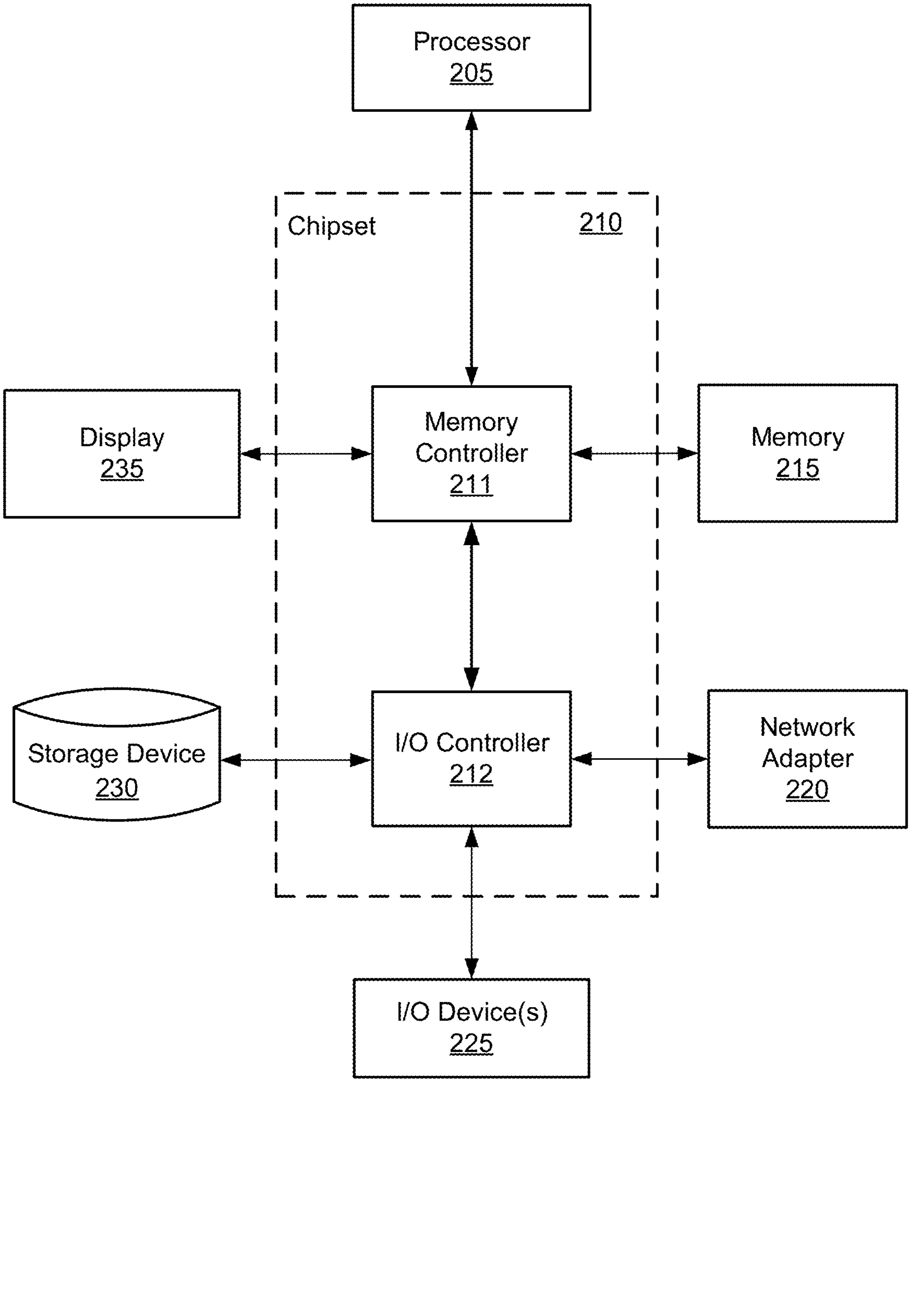
FIG. 2 is a high-level block illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

II. Overview of Metabolic Health Manager

The patient health management platform 130, as described herein, recognizes that a patient's body is a unique system in a unique state in which metabolism is a core biochemical process. Accordingly, the treatment and nutrition recommendations generated by the platform 130 are tailored to suit a patient's unique metabolic state and the unique parameters or conditions that impact or have previously impacted their metabolic state. To enable a patient to achieve good or optimal metabolic health, the platform 130 records measurements of various factors and aims to improve these measurements to levels representative of an optimized metabolic state. For example, five factors commonly considered include blood sugar, triglycerides, good cholesterol (high-density lipoprotein), blood pressure, and waist circumference. Each human body is different and continuously evolving. To guide a patient towards optimal metabolic health, the platform establishes a deep understanding of the dynamic states of each human body over time by capturing continuous biosignals and deriving insights from these biosignals.

For each patient, the platform 130 leverages a combination of personalized treatments that are tailored to a patient's unique metabolic state based on a combination of timely, accurate, and complete recordings of metabolic biosignals. Such measurements are collectively referred to herein as "TAC measurements." The platform determines a current metabolic state of a human body by analyzing a unique combination of continuous biosignals received from various sources including, but not limited to, near-real-time data from wearable sensors (e.g. continuous blood glucose, heart rate, etc.), periodic lab tests (e.g., blood work), nutrition data (e.g., macronutrients, micronutrients, and biota nutrients from food and supplements of the patient), medicine data (e.g., precise dosage and time of medications taken by the patient), and symptom data (e.g., headache, cramps, frequent urination, mood, energy, etc., reported by each patient via a mobile app). This analysis is performed continuously to establish a time series of metabolic states. As a result, the platform understands not only the current state of each patient, but also the full history of states that led to the current state. Using a patient's current metabolic state and their full history of metabolic states, the platform is able to deeply personalize the treatment for each patient.

The platform applies various technologies and processing techniques to gain a deep understanding of the combination of factors contributing to a patient's metabolic state and to establish a personalized metabolic profile for each patient. For example, the platform implements a combination of analytics (e.g., analyzing trends, outliers, and anomalies in biosignals as well as correlations across multiple biosignals), rule based artificial intelligence (AI), machine learning-based AI, and automated cohorting or clustering.

For the sake of explanation, the concepts and techniques described herein are often described with reference to diabetes. However, one of skill in the art would recognize that the concepts and techniques may also be applied to any other disease resulting from an impaired metabolism. As will be described herein, a patient's metabolic health describes the overall effectiveness of their metabolism. For example, a patient's metabolic health may be categorized as impaired, functional, or optimal. To gain insight into a patient's metabolic health, the patient health management platform 130 identifies metabolic states occurring over a period of time and changes between those metabolic states. As described herein, a metabolic state represents a patient's state of metabolic health at a specific time (e.g., a state of metabolic health resulting from consumption of a particular food or adherence to a particular medication/treatment).

In addition, the term "continuously" is used throughout the description to characterize the collection of biosignals and other data regarding the patient. This term can refer to a rate of collection that is truly continuous (e.g., a constantly recorded value) or near continuous (e.g., collection at every time point or time increment, such as every millisecond, second, or minute), such as biosignals recorded by a wearable device. In some cases, continuously recorded data may refer to particular biosignals that occur semi-regularly, such as a lab test that is taken at a recurring time interval (e.g., every 10 minutes, 30 minutes, hour, 5 hours, day or number of days, week or number of weeks, etc.). The term "continuously" does not exclude situations in which wearable sensors may be removed during certain activities or at times of day (e.g., while showering). In other embodiments, the platform collects multiple biosignals that, in combination, represent a continuous or near continuous signal collection even though some biosignals are collected more frequently than others.

Figure 3:
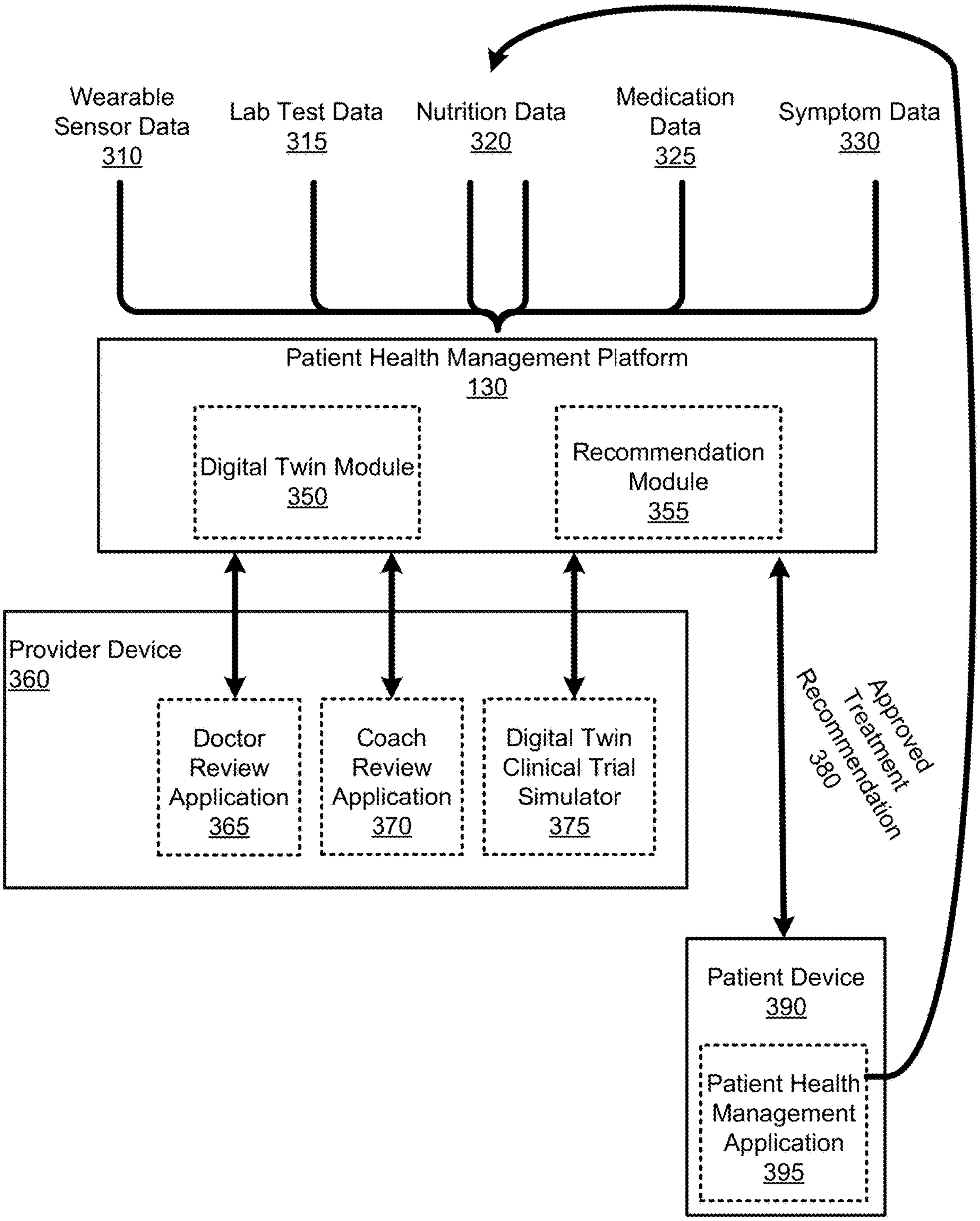
FIG. 3 is an illustration of the interactions between various components of the metabolic health manager involved in generating and providing a patient-specific recommendation to a patient, according to one embodiment.

FIG. 3 is an illustration of the interactions between various components of the metabolic health manager 100 that are involved in generating and providing a patient-specific recommendation, according to one embodiment. A patient health management platform 130 receives biosignals recorded for a patient by a variety of sources at varying intervals. The patient health management platform 130 continues to receive biosignal data from each source and, as data is received, assigns the biosignal data to a particular metabolic state. Accordingly, the platform 130 continuously augments a patient's current metabolic state with biosignal data and continuously refines recommendations based on the current metabolic state. Types of biosignal data include, but are not limited to, wearable sensor data 310, lab test data 315, nutrition data 320, medication data 325, and symptom data 330. Biosignal input data is further described below in Section III Biosignal Data. Based on the combination of received biosignals, the patient health management platform 130 generates a patient-specific recommendation describing a treatment to improve or maintain a patient's metabolic health in the long-term.

As illustrated in FIG. 3, the patient health management platform 130 comprises a digital twin module 350 and a recommendation module 355. However, in other embodiments, the patient health management platform 130 may include different and/or additional components. The digital twin module 350 generates a digital replica of the patient's metabolic health based on a combination of biological data and patient data, hereafter referred to as a digital twin. The digital twin module 350 considers different aspects of a patient's health and well-being to generate and continuously update a patient's digital twin. Accordingly, as described herein, a digital twin is a dynamic digital representation of the metabolic function of a patient's human body. The digital twin module 350 continuously monitors biological data and patient data and correlates a patient's metabolic history with their ongoing medical history to identify changes in the patient's metabolic state.

The digital twin module 350 implements a combination of analytic techniques to process the combination of biosignals into a holistic representation of a patient's describes a treatment to improve or maintain a patient's metabolic heath more immediately, for example a subsequent metabolic metabolic health. The digital twin module 350 generates a representation of a patient's true, metabolic state (or metabolic response) by inputting the most recently recorded wearable sensor data 310 and lab test data 315 to patient-specific metabolic models. Each metabolic model may be trained based on a training dataset of recorded biosignal data and known metabolic states. Accordingly, over time, the patient health management platform 130 generates a comprehensive record of how a patient's metabolic health has either improved, deteriorated, or been maintained in the form of a time sequence of metabolic states recorded for a period of time.

The digital twin module 350 additionally predicts a patient's metabolic response based on nutrition data, medication data, and symptom data recorded by a patient. During an initialization period when a patient first begins using the platform 130, the platform 130 accesses a set of metabolic states output by each metabolic model. From the accessed set of metabolic states, the digital twin module 350 identifies correlations between changes in the metabolic states and the nutrient data, the medication data, and the symptom data recorded during the initialization period. In this way, digital twin module 350 may generate a prediction of a patient's current metabolic state based on the most recently entered nutrition data 320, medication data 325, and symptom data 330. For a given period of time, the patient health management platform 130 may compare the predicted metabolic state with the true metabolic state to verify the accuracy and precision of a patient's recorded entries (e.g., recorded nutrition data, medication data, and symptom data). Additionally, as a patient continues to use the platform 130, certain correlations identified by each metabolic model are either confirmed as consistently relevant correlations or ignored as single instance anomalies. The metabolic model may be adjusted or, over time, be updated to consider one or more of the consistently relevant correlations in the generation of the metabolic model.

Based on nutrition data, medication data, symptom data, lifestyle data, and supplemental nutrition information retrieved by the nutrient data module 440, the digital twin module 350 generates a prediction of the patient's metabolic state (herein referred to as a patient's "predicted metabolic state"). The digital twin module 350 implements one or more machine-learned, metabolic models to analyze the patient data recorded over a given period of time to generate a prediction of the patient's metabolic state for that period of time. Accordingly, the prediction of the patient's metabolic state is a function of a large number of metabolic factors recorded in the patient data (e.g., fasting blood glucose, sleep, and exercise) and a nutrition profile (e.g., macronutrients, micronutrients, biota nutrients).

In one embodiment, the digital twin module 350 includes several machine-learned metabolic models, such that each metabolic model is trained to predict an effect of a single aspect of the patient data. For example, a first model may be trained to predict an impact of a patient's symptoms on their metabolic state, a second model may be trained to predict an impact of various lifestyle choices (e.g., sleep and exercise habits) on the patient's metabolic state, and a third model may be trained to predict on impact of nutrition data recorded for a period of time on the patient's metabolic state. The digital twin module 350 aggregates the output of each metabolic model to determine a holistic representation of patient's metabolic state that characterizes the combined effect of the patient's symptoms, lifestyle choices, and nutrition on their metabolic state.

As described herein, metabolic models used to predict a patient's biological response (e.g., a change in their metabolic state) are trained using a training data set comprised of labeled metabolic states and a record of patient data that contributed to each labeled metabolic state. During the training process, the metabolic model determines the impact of an aspect patient data or (e.g., particular types of foods, medications, symptoms, or lifestyle adjustments) on a patient's metabolic state by drawing correlations and relationships between recorded patient data and each labeled metabolic state, for example the impact of given foods or medications on insulin sensitivity. Once trained, the metabolic model predicts a patient's metabolic state given an aspect of the patient data as an input(s). By aggregating the output of each metabolic model, the digital twin module 350 generates a predicted change in patient's metabolic state resulting from a complete set of patient data inputs by aggregating the output of each metabolic model.

The digital twin module 350 and the various types of metabolic models implemented by the digital twin module 350 to generate a predicted metabolic state are further described with reference to FIG. 5.

The digital twin module 350 communicates the predicted metabolic state to the recommendation module 355. In one embodiment, the recommendation module 355 compares a patient's predicted metabolic state to baseline metabolic state for a patient with a functional metabolism. For patients who already have a functional metabolism, the recommendation module 355 compares the predicted metabolic state to a baseline metabolic state for a patient with an optimal metabolism. In either implementation, the recommendation module 355 determines discrepancies between the patient-specific predicted metabolic state and the baseline metabolic state and identifies one or more biosignals which could be adjusted such that the predicted state becomes more similar to the baseline state, for example lower blood glucose levels in the predicted metabolic state or an imbalance between certain micronutrients and micronutrients.

Based on a patient's true metabolic response, the recommendation module 355 generates a recommendation to improve or maintain the patient's metabolic health. The recommendation is a patient-specific a set of objectives for a patient to complete to improve the patient's metabolic health. A treatment recommendation may be a combination of several recommendations including, but not limited to, a medication regimen recommendation, a nutrition regimen recommendation, and a lifestyle recommendation. As described herein, a medication regimen recommendation may include a list of recommended medications, a recommended dosage for each medication, and a recommendation adherence schedule for each medication. In some implementations, a treatment recommendation also includes a list of alternate medications with similar medical effects to the recommended medications or treatments. A nutrition recommendation may include a list of foods that a patient can consume to supplement any macromolecules, micromolecules, or biota molecules in which they are deficient. The medication regimen, food schedule, and supplement schedule may prescribe medications, food items, or supplements which may either replenish nutrients in which a patient is deficient, offset the effects of nutrients for which a patient has an excess, or a combination thereof. The medication regimen, food schedule, and supplement schedule may also alleviate or mitigate the symptoms (as indicated by symptom data recorded by a patient) that a patient is experiencing by addressing the biological root cause of the symptoms.

One example of a medication regimen may include a recommended medication or combination of medications and an adherence schedule for each medication. One example of a food schedule may include a recommended food item or, more broadly, a category of food item and an amount of the food item to be consumed. Similarly, a lifestyle adjustment may prescribe particular lifestyle adjustments for addressing a patient's symptoms or nutrient abnormalities. Examples of lifestyle adjustments include, but are not limited to, increasing physical activity or increasing a patient's amount of sleep. In some implementations, the content of lifestyle adjustments may broadly overlap with food or medication adjustments. For example, a lifestyle adjustment may recommend a patient replace refined carbohydrates with wholegrain foods, while the food schedule includes a set of particular wholegrain foods.

The recommendation module 355 may apply several data processing techniques to interpret the data from a patient's metabolic state when generating a patient-specific recommendation. In one implementation, the recommendation module 355 applies a rule-based model, which generates at least a portion of the recommendation based on medical practices that are known to be consistently effective. The rule-based model accesses and applies one or more rules defined by experts that codify and automate a physician's medical knowledge. For example, if a patient has bloodwork showing hemoglobin A1c (HbA1C) within a certain range A1 and has a body mass index (BMI) within a certain range B1, prescribe Medicine A at a certain dosage to the patient. However, if another patient has Hba1C in a different range A2 and BMI in a different range B2, then prescribe a combination of Medicines B and C at certain dosages to that patient. Additionally, the recommendation module 355 may implement a cohorting model to assign patients with similar metabolic states or, more generally, similar metabolic health to the same cohort and then generate a treatment that is tailored for a specific cohort. In some implementations, the recommendation module 355 includes a personalized nutrition engine configured to generate the personalized layer of the nutrition database 140 as described above.

For example, in a phenomenon known as the Dawn effect, a significant number of patients suffering from diabetes are affected by an abnormal increase in blood glucose in the early morning hours while they are asleep. To inhibit the Dawn effect, a patient-specific recommendation may instruct a patient to consume a nutrient-rich food item or quantity of food item, for example a spoonful of medium-chain triglyceride (MCT)-rich coconut oil, known to contain nutrients that inhibit the Dawn effect. Upon doing so, the patient's metabolism will metabolize the consumed nutrient in time to allow the metabolized ketones to counteract the Dawn Effect. Biological interactions including the Dawn effect may be identified or determined based on an analysis of a patient's metabolic history (e.g., the progress tracker illustrated in FIG. 3). Accordingly, the recommendation module 355 may generate a recommendation prescribing one of any number of nutrients to inhibit one of any number of metabolic interactions. In such implementations, the recommendation module 355 relies on analysis of a population of patients to initially identify such metabolic interactions, and then relies on patient-level data to personalize the identification of such interactions, for example by narrowing the list to only relevant metabolic interactions.

In some implementations, the recommendation module 355 generates multiple candidate recommendations and communicates each candidate recommendation to digital twin module 350. Each candidate recommendation prescribes a different possible intervention (e.g., adjustments or changes in a patient's nutrition, exercise, and sleep habits). For each candidate recommendation, the digital twin module 350 predicts a patient's metabolic response that would result from adherence to the candidate recommendation. Based on the predicted response, the recommendation module 355 compares multiple candidate recommendations to confirm which candidate recommendations will have the most positive effects on the patient's metabolic health. The digital twin module 350 uses a combination of metabolic models to predict a future metabolic state of a that would result if the patient adhered to the recommendation.

After generating the patient-specific recommendation, the recommendation module 355 communicates the recommendation to a health care provider device 120 to be reviewed by a doctor or a coach. Via a review application (e.g., the doctor review application 365) the doctor, or another trained professional, may review the treatment recommendation to identify any errors or potential risks in the generated recommendation. Optimally, the adherence of the recommendation module 355 to a set of medical rules applied by the rule-based model generates a recommendation including a combination of medications, nutrient sources, and lifestyle adjustments that would be most beneficial to the patient. However, in some cases, the doctor may be aware of certain knowledge that has not been captured in the system yet. For example, the patient may not have responded well to a given medication in the past. Via the doctor review application, a doctor may manually identify such an exception and report that exception back to the recommendation module 355. In addition to identifying the exception, the doctor may also return a corrected recommendation to the recommendation module 355. The recommendation module 355 may dynamically re-train the rule-based model using the new knowledge to prevent the same error from being made in future recommendations. Alternatively, the recommendation module 355 generates an alternative recommendation based on the exception identified by the doctor and returns the revised recommendation to the provider device 120 for further review. The recommendation module 355 is further described with reference to FIG. 5

More information regarding the patient health management platform can be found in U.S. patent application Ser. No. 16/993,177, filed on Aug. 13, 2020, which is incorporated by reference herein in its entirety.

The patient health management platform 130 may communicate the treatment recommendation to a provider device 120, where a doctor reviews the recommendation to confirm its medical accuracy or effectiveness via a doctor review application interface 365. The patient health management platform 130 may also communicate the recommendation to a provider device 120, where a metabolic health coach may review the recommendation to confirm the practicality and ease of adherence of a patient to the recommendation via a coach review application 370. In some implementations, (e.g., during a training period) the platform 130 may communicate a recommendation to a doctor or a health coach for review until the platform 130 has sufficient insight to accurately understand how nutrition, treatment, and lifestyle changes will affect an individual patient's metabolic health. Until the platform 130 has sufficient insight into the kinds of nutrition, treatment, and lifestyle changes that are not only conducive for a patient, the platform 130 may communicate treatment recommendations to a provider device, a patient device, or both for approval by a metabolic health coach or doctor. In implementations in which the doctor or coach revises or adjusts a treatment recommendation, the revised treatment recommendation is returned to the patient health management platform 130.

In addition to the applications 365 and 370, the provider device may also contain an application for simulating clinical trials—a clinical trial simulator. In one embodiment, the clinical trial simulator is a Digital Twin clinical trial simulator 375, which implements a digital twin of a patient's metabolic health to predict the effectiveness and validate candidate treatment recommendations. For the sake of illustration, the embodiments described herein are described with reference to a Digital Twin clinical trial simulator, for example the Digital Twin clinical trial simulator 375. However, a person of ordinary skill in the art would appreciate that the techniques discussed herein may be applied to any suitable clinical trial simulator.

The Digital Twin clinical trial simulator 375 receives candidate treatment recommendations generated by the patient health management platform 130. In some implementations, a candidate treatment recommendation is a novel recommendation whose effectiveness is unknown, for example a recommendation generated for the first time. The Digital Twin clinical trial simulator 375 validates the candidate treatment recommendation by identifying a population of patients sensitive to the instructions included in the recommendation. For example, the recommendation may call for decreased consumption of a particular nutrient. Accordingly, the Digital Twin clinical trial simulator 375 generates a cohort of patients whose metabolic state is known to be sensitive to changes in consumption of that particular nutrient. The Digital Twin clinical trial simulator 375 inputs a feature vector encoded from the candidate treatment recommendation to the patient-specific metabolic models of each patient in the cohort, also referred to below as a patient's "digital twin," to model the impact of the candidate treatment recommendation on the patient's metabolic state. Based on the modeled impact of the candidate treatment recommendation across patients of the entire cohort, the provider device 120 validates or approves one or more candidate treatment recommendations as being effective in improving a patient's metabolic state or ineffective.

Although illustrated as a component of the provider device 120, the Digital Twin clinical trial simulator may also be stored at a remote server and communicate directly with the patient health management platform 130. The Digital Twin clinical trial simulator 375 is further discussed below with reference to FIGS. 9-14B.

An approved treatment recommendation 380 is communicated to a patient device 110, which presents the recommendation to a patient via the patient health management application 395. By interacting with the patient health management application 395, the patient reviews the treatment recommendation, tracks their progress through the treatment recommendation, and receives notifications generated by the platform regarding changes in their metabolic health. In some implementations, the patient health management application 395 may receive information from the patient health management platform 110 identifying inconsistencies or errors in information recorded using the application 395 and request that the patient correct the identified errors. Examples of such identified errors include, but are not limited to, incorrectly recording the time at which food or medication was consumed, incorrectly recording the amount of food or medication consumed, forgetting to record that a food or medication was consumed, or incorrectly recording which food or medication was consumed.

Figure 4:
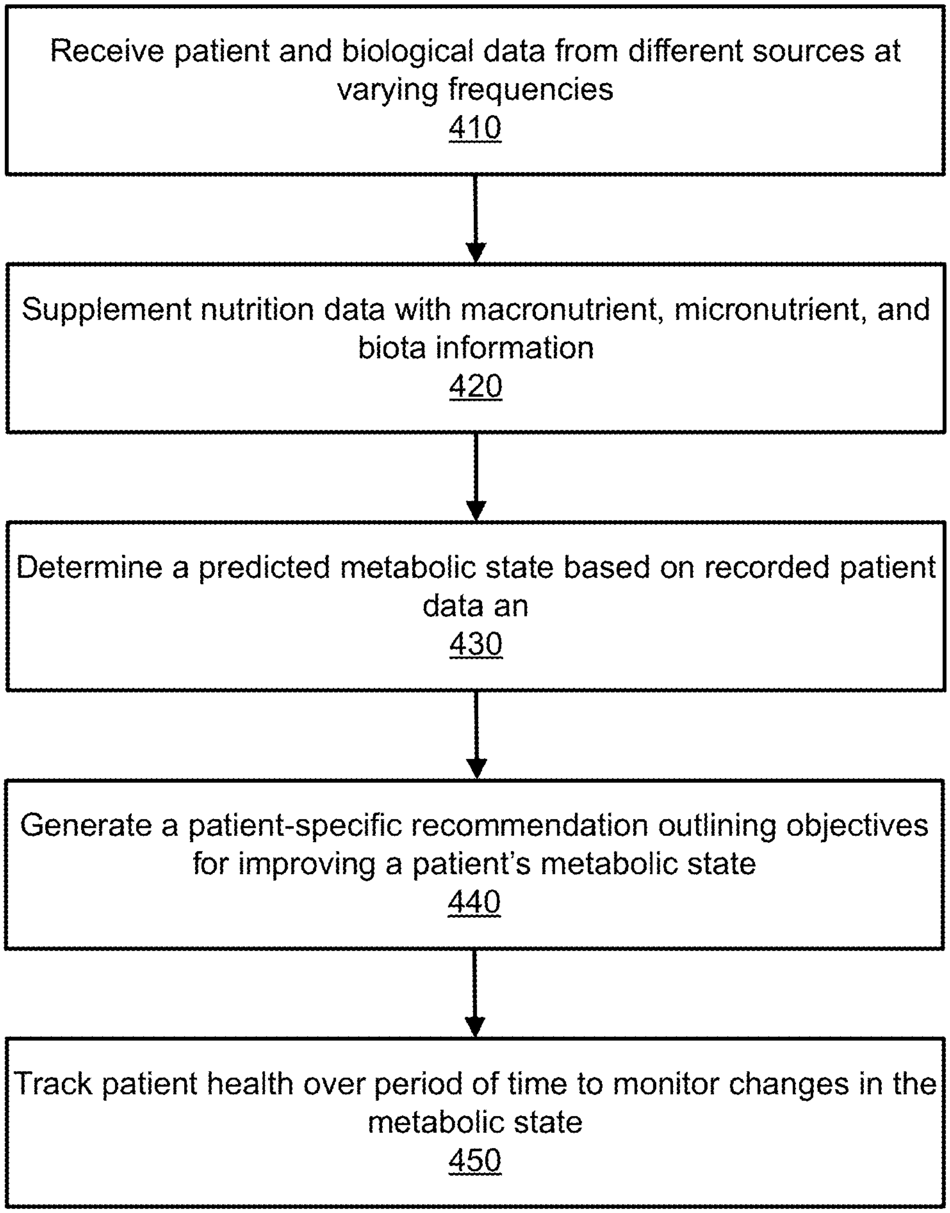
FIG. 4 is a flowchart illustrating a process for generating a patient-specific recommendation for improving metabolic health of a patient, according to one embodiment.

FIG. 4 is a flowchart illustrating a process for generating a patient-specific recommendation for improving metabolic health of a patient, according to one embodiment. The patient health management platform 130 receives 410 patient data and biological data from different sources at varying frequencies. Patient data describes data manually recorded by a patient and communicated to the platform 130. Biological data describes data manually recorded by wearable sensors or measured based on lab tests before being communicated to the platform 130.

Patient data includes nutrient data which is recorded by the patients as a list of foods which have been consumed by the patient over a period of time. While the impact of a food item by itself on a patient's metabolic state may not be known, the impact of particular macronutrients, micronutrients, and biota nutrients associated with the food item on a patient's metabolic state is known. As a result, the patient health management platform 130 accesses a nutrition database 140 storing such macronutrient, micronutrient, and biota nutrient information. Based on the accessed information, the platform 130 supplements 420 the recorded nutrition data with the accessed macronutrient, micronutrient, and biota information.

The platform 130 determines 430 a predicted metabolic state based on the recorded patient data (e.g., patient data 420). The platform 130 may categorize the predicted metabolic state as representative of poor metabolic health, functional metabolic health, or optimal metabolic health. Based on the assigned category, the platform 130 generates 440 a patient-specific recommendation outlining objectives for improving the patient's metabolic state. In particular, the recommendation may outline objectives for consuming food, taking medication, or engaging in lifestyle adjustments to supplement nutrients in which a patient is deficient and that may have contributed to the patient's deteriorated metabolic state.

Following the receipt of the recommendation, a patient continues to record patient data and wearable sensors continue to record biological data, both of which are representative of a metabolic state for a subsequent period of time. As patient data and biological data continue to be recorded, the patient health management platform 130 tracks 450 patient health over a period of time to monitor changes in the patient's metabolic state. Based on the monitored changes, the platform 130 is able to confirm whether or not a patient is adhering to the recommendation generated by the platform 130. If the patient is not adhering to the recommendation, the platform 130 may generate a notification or reminder to the patient, a doctor assigned to the patient, a coach assigned to the patient, or a combination thereof. If that patient adheres to the recommendation, the platform 130 is able to review the changes in metabolism to confirm that the recommendation is improving the patient's metabolic health. If the platform is not improving the patient's metabolic health, the platform 130 is able to dynamically revise the recommendation to correct the deficiencies of the initial recommendation. If the platform is improving the patient's metabolic health, the platform 130 is able to dynamically update the recommendation to continue to optimize the patient's metabolic health in view of their improved metabolic state.

III. Biosignal Data

A patient health management platform 130 receives biosignal data for a patient from a variety of sources including, but not limited to, wearable sensor data 310, lab test data 315, nutrition data 320, medication data 325, symptom data 330.

A patient using the metabolic health manager is outfitted with one or more wearable sensors configured to continuously record biosignals, herein referred to as wearable sensor data 310. Wearable sensor data 310 includes, but is not limited to, biosignals describing a patient's heart rate, record of exercise (e.g., steps, average number of active minutes), quality of sleep (e.g., sleep duration, sleep stages), a blood glucose measurement, a ketone measurement, systolic and diastolic blood pressure measurements, weight, BMI, percentage of fat, percentage of muscle, bone mass measurement, and percent composition of water. A wearable sensor may be a sensor that is periodically removable by a patient (e.g., a piece of jewelry worn in contact with a patient's skin to record such biosignals) or a non-removable device/sensor embedded into a patient's skin (e.g., a glucose patch). Whenever worn or activated to record wearable sensor data 310, the sensor continuously records one or more of the measurements listed above. In some implementations, a wearable sensor may record different types of wearable sensor data 310 at different rates or intervals. For example, the wearable sensor may record blood glucose measurements, heart rate measurements, and steps in 15 second intervals, but record blood pressure measurements, weight measurements, and sleep trends in daily intervals.

The patient health management platform 130 also receives lab test data 315 recorded for a patient. As described herein, lab test data 315 describes the results of lab tests performed on the patient. Examples of lab test data 315 include, but are not limited to, blood tests or blood draw analysis. Compared to the frequencies at which wearable sensor data 310 is recorded, lab test data 315 may be recorded at longer intervals, for example bi-weekly or monthly. In some implementations, the patient health management platform 130 receives data measured from 126-variable blood tests.

The patient health management platform 130 may also receive nutrition data 320 describing food that a patient is consuming or has consumed. Via an interface (e.g., the application interface 385) presented on the patient device 380, a patient enters a record of food that they have consumed on a per meal basis and a time at which each item of food was consumed. Alternatively, the patient may enter the record for food on a daily basis. The patient health management platform 130 extracts nutrition details (e.g., macronutrient, micronutrient, and biota nutrient data) from a nutrition database (not shown) based on the food record entered by the patient. As an example, via a patient device 380, a patient may record that they consumed two bananas for breakfast at 7:30 AM. The record of the two bananas is communicated to the patient health management platform 130 and the patient health management platform 130 accesses, from a nutrition database, nutrient data including the amount of potassium in a single banana. The accessed nutrient data is returned to the patient health management platform 130 as an update to the recorded nutrition data 320. Via the same interface or one similar to the interface used to record food consumed, a patient may record and communicate medication data 325 and symptom data 330 to the patient health management platform 130. Medication data 325 describes a type of medication taken, a time at which the medication was taken, and an amount of the medication taken. In addition to nutrition data 320 and medication data 325, the patient health management platform 130 may receive descriptions of a patient's energy, mood, or general level of satisfaction with their lifestyle, treatment plan, and disease management.

Examples of biosignal data recorded and communicated to the patient health management platform 130 include, but are not limited to, those listed in Table 1. Table 1 also lists a source for recording each example of biosignal data.

TABLE 1

Example Biosignal Data and Source

| Category | Type | Signal | Source |
|---|---|---|---|
| Sensor Data | Biomarker | Weight | Body Composition Scale |
| | Biomarker | Body fat % | Body Composition Scale |
| | Biomarker | Subcutaneous fat % | Body Composition Scale |
| | Biomarker | Visceral fat % | Body Composition Scale |
| | Biomarker | Body water % | Body Composition Scale |
| | Biomarker | Muscle % | Body Composition Scale |
| | Biomarker | Bone mass | Body Composition Scale |
| | Biomarker | Basal metabolic rate | Body Composition Scale |
| | Biomarker | Protein | Body Composition Scale |
| | Biomarker | Lean body weight | Body Composition Scale |
| | Biomarker | Muscle mass | Body Composition Scale |
| | Biomarker | Metabolic age | Body Composition Scale |
| | Biomarker | Continuous Blood Glucose | Continuous Glucose Meter |
| | Biomarker | Ketones | Ketone Meter |
| | Biomarker | Systolic BP | Blood Pressure Meter |
| | Biomarker | Diastolic BP | Blood Pressure Meter |
| | Heart | Resting Heart Rate | Fitness Watch |
| | Heart | Continuous Heart Rate | Fitness Watch |
| Lab Test Data | Biomarker | Skin Temperature | Patient Investigation/Test |
| | Biomarker | Oxygen Saturation | Patient Investigation/Test |
| | Biomarker | Waist Circumference | Patient Investigation/Test |
| | Biomarker | Age | Patient Interview |
| | Biomarker | Gender | Patient Interview |
| | Biomarker | Height | Patient Interview |
| | Biomarker | BMI | Patient Interview |
| | Biomarker | HbA1c | Blood Test |
| | Biomarker | 5dg-cgm | Blood Test |
| | Biomarker | 1dg-cgm | Blood Test |
| | Biomarker | Insulin | Blood Test |
| | Biomarker | Fructosamine | Blood Test |
| | Biomarker | C-Peptide | Blood Test |
| | Biomarker | HOMA-IR | Blood Test |
| | Biomarker | 5dk | Blood Test |
| | Biomarker | Cholesterol | Blood Test |
| | Biomarker | Triglycerides | Blood Test |
| | Biomarker | HDL Cholesterol | Blood Test |
| | Biomarker | LDL Cholesterol | Blood Test |
| | Biomarker | VLDL Cholesterol | Blood Test |
| | Biomarker | Triglyceride/HDL Ratio | Blood Test |
| | Biomarker | Total Cholesterol/ HDL Ratio | Blood Test |
| | Biomarker | Non - HDL Cholesterol | Blood Test |
| | Biomarker | LDL/HDL Ratio | Blood Test |
| | Biomarker | Total Iron Binding Capacity (TIBC) | Blood Test |
| | Biomarker | Serum Iron | Blood Test |
| | Biomarker | % Transferrin Saturation | Blood Test |
| | Biomarker | Amylase | Blood Test |
| | Biomarker | Lipase | Blood Test |
| | Biomarker | Ferritin | Blood Test |

TABLE 1-continued

Example Biosignal Data and Source

| Category | Type | Signal | Source |
|---|---|---|---|
| | Biomarker | Homocysteine | Blood Test |
| | Biomarker | Magnesium | Blood Test |
| | Biomarker | ALT | Blood Test |
| | Biomarker | AST | Blood Test |
| | Biomarker | ALP | Blood Test |
| | Biomarker | Total Bilirubin | Blood Test |
| | Biomarker | Direct Bilirubin | Blood Test |
| | Biomarker | Indirect Bilirubin | Blood Test |
| | Biomarker | Gamma Glutamyl Transferase (GGT) | Blood Test |
| | Biomarker | Protein | Blood Test |
| | Biomarker | Albumin | Blood Test |
| | Biomarker | A/G Ratio | Blood Test |
| | Biomarker | Globulin | Blood Test |
| | Biomarker | Urea | Blood Test |
| | Biomarker | Creatinine | Blood Test |
| | Biomarker | Uric Acid | Blood Test |
| | Biomarker | GFR | Blood Test |
| | Biomarker | Blood urea nitrogen (BUN) | Blood Test |
| | Biomarker | BUN/Creatinine Ratio | Blood Test |
| | Biomarker | Lipoprotein(a) | Blood Test |
| | Biomarker | Apolipoprotein A1 | Blood Test |
| | Biomarker | ApoB | Blood Test |
| | Biomarker | hs-CRP | Blood Test |
| | Biomarker | Apo B/Apo A1 Ratio | Blood Test |
| | Biomarker | LP-PLA2 | Blood Test |
| | Biomarker | Total Triiodothyronine [T3] | Blood Test |
| | Biomarker | Total Thyroxine [T4] | Blood Test |
| | Biomarker | TSH | Blood Test |
| | Biomarker | Sodium | Blood Test |
| | Biomarker | Chloride | Blood Test |
| | Biomarker | Potassium | Blood Test |
| | Biomarker | Bicarbonate | Blood Test |
| | Biomarker | Calcium | Blood Test |
| | Biomarker | Phosphorous | Blood Test |
| | Biomarker | Anion Gap | Blood Test |
| | Biomarker | Vitamin A | Blood Test |
| | Biomarker | Vitamin D2 | Blood Test |
| | Biomarker | Vitamin D3 | Blood Test |
| | Biomarker | Vitamin D Total | Blood Test |
| | Biomarker | Vitamin E | Blood Test |
| | Biomarker | Vitamin K | Blood Test |
| | Biomarker | Vitamin B1/Thiamin | Blood Test |
| | Biomarker | Vitamin B2/ Riboflavin | Blood Test |
| | Biomarker | Vitamin B3/ Nicotinic Acid | Blood Test |
| | Biomarker | Vitamin B5/ Pantothenic Acid | Blood Test |
| | Biomarker | Vitamin B6/ Pyridoxal-5-Phosphate | Blood Test |
| | Biomarker | Vitamin B7/Biotin | Blood Test |
| | Biomarker | Vitamin B9/Folic Acid | Blood Test |
| | Biomarker | Vitamin B12/ Cobalamin | Blood Test |
| | Biomarker | Cortisol | Blood Test |
| | Biomarker | Cystatin C | Blood Test |
| | Biomarker | Serum Zinc | Blood Test |
| | Biomarker | Serum Copper | Blood Test |
| | Biomarker | Basophils - Absolute Count | Blood Test |
| | Biomarker | Eosinophils - Absolute Count | Blood Test |
| | Biomarker | Lymphocytes - Absolute Count | Blood Test |
| | Biomarker | Monocytes - Absolute Count | Blood Test |
| | Biomarker | Mixed - Absolute Count | Blood Test |

TABLE 1-continued

| Example Biosignal Data and Source | | | |
|---|---|---|---|
| Category | Type | Signal | Source |
| | Biomarker | Neutrophils - Absolute Count | Blood Test |
| | Biomarker | Basophils | Blood Test |
| | Biomarker | Eosinophils | Blood Test |
| | Biomarker | Immature Granulocytes (Ig) | Blood Test |
| | Biomarker | Immature Granulocyte Percentage (Ig %) | Blood Test |
| | Biomarker | White Blood Cells (Leucocytes Count) | Blood Test |
| | Biomarker | Lymphocyte Percentage | Blood Test |
| | Biomarker | Mean Corpuscular Hemoglobin (Mch) | Blood Test |
| | Biomarker | Mean Corp. Hemo. Conc. (Mchc) | Blood Test |
| | Biomarker | MCV | Blood Test |
| | Biomarker | Monocytes | Blood Test |
| | Biomarker | Mean Platelet Volume (Mpv) | Blood Test |
| | Biomarker | Neutrophils | Blood Test |
| | Biomarker | Nucleated Red Blood Cells | Blood Test |
| | Biomarker | Nucleated Red Blood Cells % | Blood Test |
| | Biomarker | Plateletcrit (Pct) | Blood Test |
| | Biomarker | Hematocrit | Blood Test |
| | Biomarker | Platelet Distribution Width (Pdw- SD) | Blood Test |
| | Biomarker | Platelet To Large Cell Ratio (Plcr) | Blood Test |
| | Biomarker | Platelet Count | Blood Test |
| | Biomarker | Red Blood Cell Count | Blood Test |
| | Biomarker | Red Cell Distribution Width (Rdw-Cv) | Blood Test |
| | Biomarker | Red Cell Distribution Width - Sd (Rdw-Sd) | Blood Test |
| | Biomarker | Blood pH | Blood Test |
| | Biomarker | Hemoglobin | Blood Test |
| | Biomarker | ACCP | Blood Test |
| | Biomarker | ANA | Blood Test |
| | Biomarker | Cadmium | Blood Test |
| | Biomarker | Cobalt | Blood Test |
| | Biomarker | Chromium | Blood Test |
| | Biomarker | Caesium | Blood Test |
| | Biomarker | Mercury | Blood Test |
| | Biomarker | Manganese | Blood Test |
| | Biomarker | Molybdenum | Blood Test |
| | Biomarker | Nickel | Blood Test |
| | Biomarker | Lead | Blood Test |
| | Biomarker | Antimony | Blood Test |
| | Biomarker | Selenium | Blood Test |
| | Biomarker | Tin | Blood Test |
| | Biomarker | Strontium | Blood Test |
| | Biomarker | Thallium | Blood Test |
| | Biomarker | Uranium | Blood Test |
| | Biomarker | Vanadium | Blood Test |
| | Biomarker | Silver | Blood Test |
| | Biomarker | Aluminium | Blood Test |
| | Biomarker | Arsenic | Blood Test |
| | Biomarker | Barium | Blood Test |
| | Biomarker | Beryllium | Blood Test |
| | Biomarker | Bismuth | Blood Test |
| | Biomarker | Testosterone | Blood Test |
| Lifestyle Data | Sleep | Sleep Quality | Fitness Watch |
| | Sleep | Minutes Asleep | Fitness Watch |
| | Sleep | Minutes Awake | Fitness Watch |
| | Sleep | Minutes Light Sleep | Fitness Watch |
| | Sleep | Minutes Deep Sleep | Fitness Watch |
| | Sleep | Minutes REM Sleep | Fitness Watch |
| | Exercise | Activity Calories | Fitness Watch |
| | Exercise | Marginal Calories | Fitness Watch |
| | Exercise | BMR Calories | Fitness Watch |

TABLE 1-continued

| Example Biosignal Data and Source | | | |
|---|---|---|---|
| Category | Type | Signal | Source |
| | Exercise | Total Calories Burned | Fitness Watch |
| | Exercise | Continuous Steps (per minute) | Fitness Watch |
| | Exercise | Fairly Active Minutes | Fitness Watch |
| | Exercise | Light Active Minutes | Fitness Watch |
| | Exercise | Very Active Minutes | Fitness Watch |
| | Exercise | Sedentary Minutes | Fitness Watch |
| | Exercise | Stress | Fitness Watch |
| | Patient Information | Age | Patient Interview |
| | Patient Information | Gender | Patient Interview |
| | Patient Information | Height | Patient Interview |
| | Patient Information | BMI | Patient Interview |
| | Patient Information | Vegetarian | Patient Interview |
| | Patient Information | Tobacco | Patient Interview |
| | Patient Information | Alcohol | Patient Interview |
| | Patient Information | Caffeine | Patient Interview |
| | Family Information | Father Diabetic? | Patient Interview |
| | Family Information | Mother Diabetic? | Patient Interview |
| | Family Information | Sibling Diabetic? | Patient Interview |
| | Family Information | Grandparents Diabetic? | Patient Interview |
| | Happiness | Energy | Patient Health Management App |
| | Happiness | Mood | Patient Health Management App |
| | Happiness | Cuisine Preferences | Patient Health Management App |
| | Happiness | Food Ratings | Patient Health Management App |
| | Happiness | Meal Ratings | Patient Health Management App |
| | Happiness | Exercise Preferences | Patient Health Management App |
| Symptom Data | Symptom | Headache | Patient Health Management App |
| | Symptom | Cramps | Patient Health Management App |
| | Symptom | Numbness | Patient Health Management App |
| | Symptom | Frequent Urination | Patient Health Management App |
| | Symptom | Blurred Vision | Patient Health Management App |
| | Symptom | Tiredness | Patient Health Management App |
| | Symptom | Excess hunger | Patient Health Management App |
| | Symptom | Giddiness | Patient Health Management App |
| | Symptom | Nausea | Patient Health Management App |
| | Symptom | Vomiting | Patient Health Management App |
| | Symptom | Diarrhea | Patient Health Management App |
| | Symptom | Excess thirst | Patient Health Management App |
| | Symptom | Constipation | Patient Health Management App |
| | Symptom | Erectile dysfunction | Patient Health Management App |
| | Symptom | Sleeplessness | Patient Health Management App |
| Medication Data | Medication | Diabetes Medicine | Patient Health Management App |
| | Medication | Insulin | Patient Health Management App |
| | Medication | Hypertension Medicines | Patient Health Management App |
| | Medication | Cholesterol Medicines | Patient Health Management App |
| | Medication | Obesity Medicines | Patient Health Management App |
| | Medication | Heart Medicines | Patient Health Management App |
| | Medication | Arthritis Medicines | Patient Health Management App |
| Nutrition Data | Macronutrients | Net Carb | Nutrition Database/Patient Health Management App |
| | Macronutrients | Calories consumed | Nutrition Database/Patient Health Management App |
| | Macronutrients | Net GI Carb | Nutrition Database/Patient Health Management App |
| | Macronutrients | Fiber | Nutrition Database/Patient Health Management App |
| | Macronutrients | Fat | Nutrition Database/Patient Health Management App |
| | Macronutrients | Protein | Nutrition Database/Patient Health Management App |
| | Macronutrients | Total Carb | Nutrition Database/Patient Health Management App |

TABLE 1-continued

| Example Biosignal Data and Source | | | |
|---|---|---|---|
| Category | Type | Signal | Source |
| | Micronutrients | Fructose | Nutrition Database/Patient Health Management App |
| | Micronutrients | Sodium | Nutrition Database/Patient Health Management App |
| | Micronutrients | Potassium | Nutrition Database/Patient Health Management App |
| | Micronutrients | Magnesium | Nutrition Database/Patient Health Management App |
| | Micronutrients | Calcium | Nutrition Database/Patient Health Management App |
| | Micronutrients | Chromium | Nutrition Database/Patient Health Management App |
| | Micronutrients | Omega 3 | Nutrition Database/Patient Health Management App |
| | Micronutrients | Omega 6 | Nutrition Database/Patient Health Management App |
| | Micronutrients | ALA | Nutrition Database/Patient Health Management App |
| | Micronutrients | Q10 | Nutrition Database/Patient Health Management App |
| | Micronutrients | Biotin | Nutrition Database/Patient Health Management App |
| | Micronutrients | Flavonoids | Nutrition Database/Patient Health Management App |
| | Glycemic Controllers | Improve IS | Nutrition Database/Patient Health Management App |
| | Glycemic Controllers | Inhibit GNG | Nutrition Database/Patient Health Management App |
| | Glycemic Controllers | Inhibit Carb Absorption | Nutrition Database/Patient Health Management App |
| | Glycemic Controllers | Improve Insulin Secretion | Nutrition Database/Patient Health Management App |
| | Glycemic Controllers | Impr B-Cell Regen | Nutrition Database/Patient Health Management App |
| | Glycemic Controllers | Inhibit Hunger | Nutrition Database/Patient Health Management App |
| | Glycemic Controllers | Inhibit Glucose Kidney Reabsorption | Nutrition Database/Patient Health Management App |
| | Biotanutrients | *Lactococcus* sp. | Nutrition Database/Patient Health Management App |
| | Biotanutrients | *Lactobacillus* sp. | Nutrition Database/Patient Health Management App |
| | Biotanutrients | *Leuconostoc* sp. | Nutrition Database/Patient Health Management App |
| | Biotanutrients | *Streptococcus* sp. | Nutrition Database/Patient Health Management App |
| | Biotanutrients | *Bifidobacterium* sp. | Nutrition Database/Patient Health Management App |
| | Biotanutrients | *Saccharomyces* sp. | Nutrition Database/Patient Health Management App |
| | Biotanutrients | *Bacillus* sp. | Nutrition Database/Patient Health Management App |
| | Glycemic Impact | Glycemic Index | Nutrition Database/Patient Health Management App |
| | Fats | Saturated fat | Nutrition Database/Patient Health Management App |
| | Fats | Monounsaturated fat | Nutrition Database/Patient Health Management App |
| | Fats | Polyunsaturated fat | Nutrition Database/Patient Health Management App |
| | Fats | Trans fat | Nutrition Database/Patient Health Management App |
| | Fats | Cholesterol | Nutrition Database/Patient Health Management App |
| | Proteins | Histidine | Nutrition Database/Patient Health Management App |
| | Proteins | Isoleucine | Nutrition Database/Patient Health Management App |
| | Proteins | Lysine | Nutrition Database/Patient Health Management App |
| | Proteins | Methionine + Cysteine | Nutrition Database/Patient Health Management App |
| | Proteins | Phenylalanine + Tyrosine | Nutrition Database/Patient Health Management App |
| | Proteins | Tryptophan | Nutrition Database/Patient Health Management App |

TABLE 1-continued

| Example Biosignal Data and Source | | | |
|---|---|---|---|
| Category | Type | Signal | Source |
| | Proteins | Threonine | Nutrition Database/Patient Health Management App |
| | Proteins | Valine | Nutrition Database/Patient Health Management App |
| | Vitamins/Minerals | Vitamin A | Nutrition Database/Patient Health Management App |
| | Vitamins/Minerals | Vitamin C | Nutrition Database/Patient Health Management App |
| | Vitamins/Minerals | Vitamin D | Nutrition Database/Patient Health Management App |
| | Vitamins/Minerals | Vitamin E | Nutrition Database/Patient Health Management App |
| | Vitamins/Minerals | Vitamin K | Nutrition Database/Patient Health Management App |
| | Vitamins/Minerals | B1 | Nutrition Database/Patient Health Management App |
| | Vitamins/Minerals | B12 | Nutrition Database/Patient Health Management App |
| | Vitamins/Minerals | B2 | Nutrition Database/Patient Health Management App |
| | Vitamins/Minerals | B3 | Nutrition Database/Patient Health Management App |
| | Vitamins/Minerals | B5 | Nutrition Database/Patient Health Management App |
| | Vitamins/Minerals | B6 | Nutrition Database/Patient Health Management App |
| | Vitamins/Minerals | Folate | Nutrition Database/Patient Health Management App |
| | Vitamins/Minerals | Copper | Nutrition Database/Patient Health Management App |
| | Vitamins/Minerals | Iron | Nutrition Database/Patient Health Management App |
| | Vitamins/Minerals | Zinc | Nutrition Database/Patient Health Management App |
| | Vitamins/Minerals | Manganese | Nutrition Database/Patient Health Management App |
| | Vitamins/Minerals | Phosphorus | Nutrition Database/Patient Health Management App |
| | Vitamins/Minerals | Selenium | Nutrition Database/Patient Health Management App |
| | Vitamins/Minerals | Omega 6/omega 3 | Nutrition Database/Patient Health Management App |
| | Vitamins/Minerals | Zinc/Copper | Nutrition Database/Patient Health Management App |
| | Vitamins/Minerals | Potassium/Sodium | Nutrition Database/Patient Health Management App |
| | Vitamins/Minerals | Calcium/Magnesium | Nutrition Database/Patient Health Management App |
| | Vitamins/Minerals | PRAL Alkalinity | Nutrition Database/Patient Health Management App |
| | Metabolic Improvers | Improve BP | Nutrition Database/Patient Health Management App |
| | Metabolic Improvers | Improve Cholesterol | Nutrition Database/Patient Health Management App |
| | Metabolic Improvers | Reduce Weight | Nutrition Database/Patient Health Management App |
| | Metabolic Improvers | Improve Renal function | Nutrition Database/Patient Health Management App |
| | Metabolic Improvers | Improve Liver function | Nutrition Database/Patient Health Management App |
| | Metabolic Improvers | Improve Thyroid function | Nutrition Database/Patient Health Management App |
| | Metabolic Improvers | Improve Arthritis | Nutrition Database/Patient Health Management App |
| | Metabolic Improvers | Reduce uric acid | Nutrition Database/Patient Health Management App |
| | Food Type | Fruits | Nutrition Database/Patient Health Management App |
| | Food Type | Oils | Nutrition Database/Patient Health Management App |
| | Food Type | Spices | Nutrition Database/Patient Health Management App |
| | Food Type | Grains | Nutrition Database/Patient Health Management App |
| | Food Type | Legumes | Nutrition Database/Patient Health Management App |

TABLE 1-continued

Example Biosignal Data and Source

| Category | Type | Signal | Source |
|---|---|---|---|
| | Food Type | Nuts | Nutrition Database/Patient Health Management App |
| | Food Type | Seed Products | Nutrition Database/Patient Health Management App |
| | Cellular Stressors | Inflammatory index | Nutrition Database/Patient Health Management App |
| | Cellular Stressors | Oxidative stress index | Nutrition Database/Patient Health Management App |
| | Cellular Stressors | Gluten | Nutrition Database/Patient Health Management App |
| | Cellular Stressors | Lactose | Nutrition Database/Patient Health Management App |
| | Cellular Stressors | Alcohol | Nutrition Database/Patient Health Management App |
| | Cellular Stressors | Allergic index | Nutrition Database/Patient Health Management App |
| | Hydration | Water | Nutrition Database/Patient Health Management App |

Figure 5:
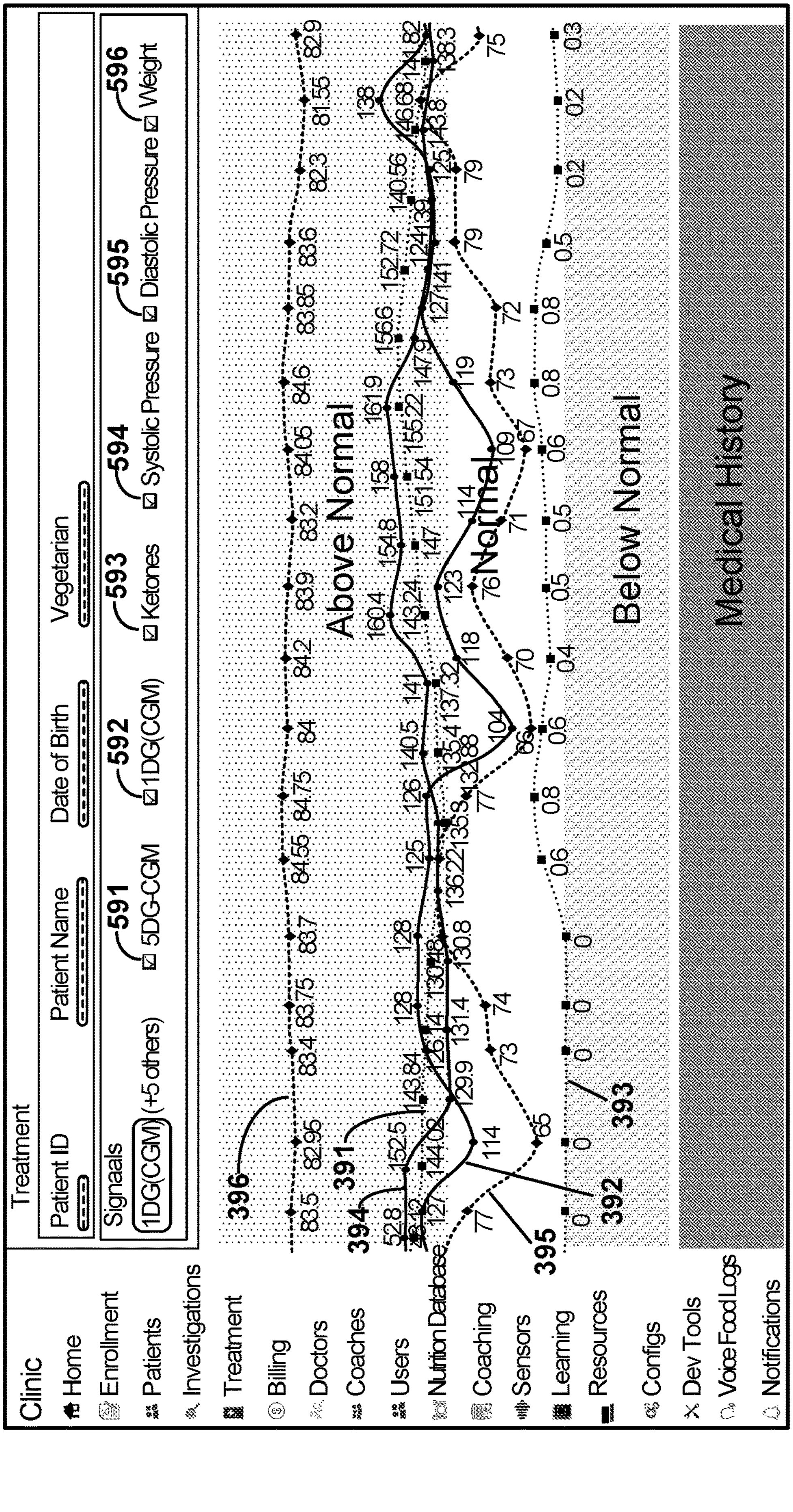
FIG. 5 is an illustration of a graphical user interface presented on a provider device to monitor a patient's metabolic progress, according to one embodiment.

FIG. 5 is an illustration of a graphical user interface presented on a provider device for monitoring a patient's metabolic progress, according to one embodiment. The illustrated interface displays biological data recorded by wearable devices over a period of time including signal curves of 5-day average blood glucose measurements (5DG-CGM) 591, 1-day average blood glucose measurements (1DG-CGM) 592, ketones 593, systolic pressure 594, diastolic pressure 595, and weight 596. The illustrated interface in FIG. 5 displays daily changes in biological data for patient (e.g., each column displayed on the interface represents a day). Each point on the signal curve represents an average value of the signal measured on that day. For example, each point along the signal curve of 1DG-CGM 592 measurements represents a patient's 1-day average glucose for a given day. In alternate embodiments, biological data may be displayed at varying frequencies, for example bidaily, weekly, etc. To determine a daily average for each measurement, wearable sensors records several measurements of each type of wearable sensor data during that interval, in some instances at varying frequencies. For example, measurements of the 5-day average blood glucose measurements 591 and the 1-day average blood glucose measurements 592 may be recorded at the same frequencies compared to the frequency at which ketones 593 are measured or the weight 596 is recorded. Additionally, measurements of the systolic pressure 594 and diastolic pressure 595 may be recorded at the same interval, compared to the other illustrated measurements. By recording such a large volume of measurements over several periods of time for several patients, the training of machine-learned models may be performed using extensive training datasets. Additionally, given the large volume of wearable sensor data, machine learned models may provide extensive insight into a patient's metabolic health at a high level of granularity.

IV. Patient Health Management Platform

IV.A Metabolic Digital Twin

Figure 6:
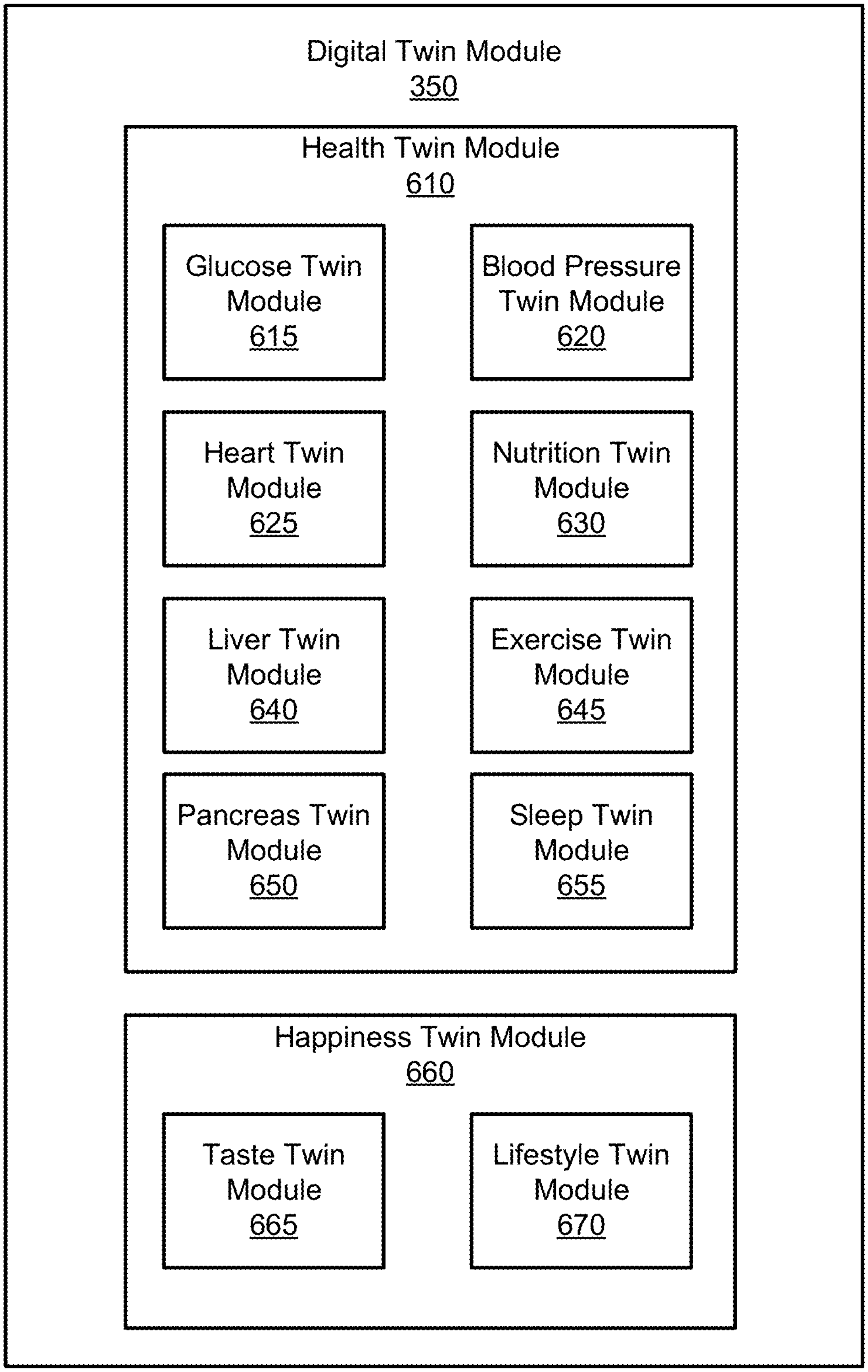
FIG. 6 is a block diagram of the system architecture of a digital twin module, according to one embodiment.

As described above, the digital twin module 350 generates a digital twin of the patient's metabolic health to continuously monitor and update different aspects of a patient's health and well-being. FIG. 6 is a block diagram of the system architecture of a digital twin module 350, according to one embodiment. The digital twin module 350 includes a health twin module 610 and a happiness twin module 660. The digital twin module 350 may include different and/or additional components to perform the same functions described with regards to the digital twin module 350. The digital twin module 350 generates a digital replica of a patient's metabolic state in two dimensions: a health dimension and a happiness dimension.

The health twin module 610 generates a digital replica of the health dimension of a metabolic state based on biological measurements recorded by wearable sensors and lab test data. In the embodiment illustrated in FIG. 6, the health twin module 610 comprises a glucose twin module 615, a blood pressure twin module 620, a heart twin module 625, a nutrition twin module 630, a liver twin module 640, an exercise twin module 645, a pancreas twin module 650, and a sleep twin module 655. Each component of the health twin module 610 captures and updates a critical aspect of a patient's metabolic health such that the digital twin represents the patient's overall metabolic health. The health twin module 610 may include additional, fewer, or a different combination of components to generate a digital twin based on varying aspects of a patient's metabolic health. In some embodiments, each component of the health twin module 610 generates an output indicating a condition of an aspect of the patient's metabolic health. For example, the heart twin module 625 may generate an output indicating the patient's heart health rating on a scale of 100, for example 85. This is derived from cardiac health biomarkers such as Lipoprotein(a), Apolipoprotein B, and High-Sensitivity C-Reactive Protein (HS-CRP).

The glucose twin module 615 tracks and analyzes glucose dynamics for a patient over time to enable the digital twin to model glucose dynamics for the patient. The glucose twin module 615 may analyze glucose dynamics recorded via a wearable sensor. The heart twin module 625, liver twin module 640, and the pancreas twin module 850 track and analyze function and physiology of a patient's heart, liver, and pancreas to enable the digital twin to model heart, liver, and pancreas function for the patient. The heart twin module 625, the liver twin module 640, and the pancreas twin module 650 may analyze function of a patient's heart, liver, and pancreas based on information recorded via one or more lab tests. The blood pressure twin module 620 tracks and analyzes blood pressure dynamics for a patient over time to enable the digital twin to model blood pressure dynamics for the patient. The blood pressure twin module 615 may analyze blood pressure dynamics recorded via a wearable sensor or via lab test data.

The nutrition twin module 630 communicates with the nutrient data module 640 to track and analyze nutrition information of food consumed by a patient to enable the digital twin to model the impact of food consumed by the patient. The nutrition twin module 630 may analyze a combination of macronutrient parameters, micronutrient parameters, and biota nutrients for each food item recorded by the patient through a patient device 380. The exercise twin module 645 tracks exercise activity for a patient and analyzes those exercise habits by correlating periods of exercise (or inactivity) with changes in the patient's metabolic state. The exercise twin module 645 may analyze exercise activity recorded by the patient through a patient device 380. Similarly, the sleep twin module 655 tracks sleep trends for a patient and analyzes those sleep trends by correlating quality, length, and frequency of sleep with changes in the patient's metabolic state. The sleep twin module 655 may analyze sleep trends recorded by the patient through a patient device 380 or by a wearable sensor.

Each module (or component) of the health twin module 610 is connected to and communicates with other modules of the health twin module 610 to capture the complex interaction effects that contribute to a patient's metabolic state. For example, blood pressure dynamics are driven by a combination of factors including blood glucose dynamics, heart function, nutrition, exercise, and sleep trends. Each of those driving factors are, in turn, driven by other factors represented in the patient's digital twin.

The happiness twin module 660 generates a digital replica of the happiness dimension of a patient's metabolic state based on feedback recorded through a patient device 380. In the embodiment illustrated in FIG. 6, the happiness twin module 660 comprises a taste twin module 665 and a lifestyle twin module 670. Each component of the happiness twin module 660 captures a critical aspect of a patient's satisfaction with their recommended treatment to their digital twin such that the digital twin also represents the patient's overall experience with treatment. The happiness twin module 620 may include additional, fewer, or a different combination of components to generate a digital twin based on varying aspects of a patient's metabolic health. In some embodiments, each of the taste twin module 660 and the lifestyle twin module 665 generate an output indicating a patient's current state of mind regarding a food item, meal recommendation, or a lifestyle recommendation prescribed by a patient-specific recommendation. For example, each food consumed by a patient may be labeled with a score on a 5-star scale, such as "4 stars".

The taste twin module 660 communicates with the nutrition twin module 630 to assign a preference to each food item recorded by the patient (e.g., a label indicating whether the patient enjoyed the food item or not). In conjunction, the nutrition twin module 630 and the taste twin module 660 may compare two foods with a similar metabolic effect and prioritize whichever food the patient enjoyed more. The food item that the patient enjoyed more will be carried forward in other future patient-specific recommendations. The lifestyle twin module 660 communicates with the exercise twin module 645 and the sleep twin module 655 to assign a preference to the activities recorded by the patient. For example, if a patient wishes to engage in more exercise, future treatment recommendations may be generated with an emphasis on more frequent exercise.

As described herein, each module of the health twin module 610 and the happiness twin module 660 includes a uniquely trained metabolic model. In particular, when generating a prediction of a patient's metabolic state, each involved metabolic model is trained to determine an impact of a particular type of patient data input on a patient's metabolic state. When generating a prediction of a patient's metabolic state, the digital twin module 350 may consider the output of the metabolic models trained to receive patient data as inputs, for example the nutrition twin module 630, the exercise twin module 645, the sleep twin module 655, and the lifestyle twin module 670. For example, the nutrition twin module 630 implements a metabolic model to predict a patient's metabolic state based on patient data identifying food items consumed by the patient. As additional examples, each of exercise twin module 645, the sleep twin module 655, and the lifestyle twin module 670 implement a metabolic model to predict a patient's metabolic state based on patient data describing the patient's exercise habits, sleep habits, and lifestyle habits, respectively. The digital twin module 350 may also consider metabolic models that are not illustrated in FIG. 6, or the other twin modules that are illustrated in FIG. 6 when generating a prediction of a patient's metabolic state.

In comparison, each metabolic model involved in determining a patient's true metabolic state is trained to determine an impact of a particular type of biosignal input on a patient's metabolic state, for example the glucose twin module 615, the blood pressure twin module 620, the heart twin module 625, the liver twin module 640, and the pancreas twin module 650. For example, the glucose twin module 615 implements a metabolic model to evaluate a patient's true metabolic state based on input biosignals describing the glucose dynamics of the patient. As additional examples, each of the heart twin module 625, the liver twin module 640, and the pancreas twin module 650 implement metabolic models to evaluate, respectively, a true performance of a patient's heart, liver, and pancreas based on input biosignals describing the functionality of those organs. As yet another example, the blood pressure twin module 620 implements a metabolic model to evaluate a patient's true metabolic state based on input biosignals describing blood pressure dynamics of the patient. The digital twin module 350 may also consider metabolic models that are not illustrated in FIG. 6, or the other twin modules that are illustrated in FIG. 6 when generating a prediction of a patient's metabolic state.

In some embodiments, modules of the digital twin module 350 may implement a combination of multiple machine-learned models to more accurately and completely characterize each aspect of a patient's metabolic health. For example, as will be described below in Section IV.D, the glucose twin module 615 may implement both a glucose impact model (as described in Section IV.D.1) and a 1-Day Average Glucose model (as described in Section IV.D.2).

After a digital twin of a patient has been initialized, components of the digital twin module 350 continuously collect data describing changes in conditions contributing to the patient's metabolic health. When any component of the digital twin module 350 receives updated data, the digital twin module 350 updates a digital twin of the patient in near real-time to reflect the updated data.

IV.D Machine-Learned Metabolic Models

Because the human body is a complex system and different patients may respond differently to the same input stimuli, the patient health management platform 130 includes mathematical models trained to learn the relationships between response signals representing a patient's metabolic states and input stimuli causing those responses. As described above, the patient health management platform 130 applies machine-learning based artificial intelligence to generate a precision treatment recommendation for improving a patient's metabolic health by predicting their response to future input stimuli. The digital twin module 350 implements a combination of machine-learned models that are trained to predict a response of the human body based on each patient's current metabolic state and a set of inputs (e.g., recorded patient data, sensor data, and biological data). Each machine-learned model enables the digital twin module 350 to automatically analyze a large combination of biosignals recorded for each patient to characterize a patient's current or potential metabolic state.

In order to model a patient's metabolic state and to track changes in their metabolic health, a model, such as a mathematical function or other more complex logical structure, is trained using the combination of input biosignals described above, to determine a set of parameter values that are stored in advance and used as part of the metabolic analysis. Briefly, a representation of a patient's metabolic state is generated by inputting wearable sensor data, lab test, and recorded patient data as input values to the model's function and parameters, and, together with values assigned to those parameters, determines a patient's metabolic health. As described herein, the term "model" refers to the result of the machine learning training process. Specifically, the model describes the generation of a function for representing a patient's metabolic state and the determined parameter values that the function incorporates. "Parameter values" describe the weight that is associated with at least one of the featured input values. "Input values" describe the variables of the function or the conditions to be used in conjunction with the parameter values to determine the risk score. Input values can be thought of as the numerical representations of the various features that the model takes into account, for example the input biosignals. During training, from input values of the training dataset, the parameter values of a model are derived. Further, the training data set is used to define the parameter values at a specified time interval, whereas the input values are continuously updated by the patient's conditions.

The digital twin module 350 may include a combination of machine-learned models to generate various representations of a metabolic state, for example a metabolic models trained to predictively model a patient's metabolic state based on recorded nutrition data, medication data, symptom data and lifestyle data, and to model a patient's true metabolic state based on sensor data and lab test data. The digital twin module 350 may input patient data 420, for example nutrition data, medication data, symptom data, or lifestyle data, into a combination metabolic models (e.g., the nutrition twin model 630 and the lifestyle twin module 670) to predict a patient's metabolic state that would result from the recorded patient data. The digital twin module 350 may compare a recorded timeline of patient data (e.g., foods consumed by the patient, medications taken by the patient, and symptoms experienced by the patient) during a time period to a metabolic state generated for the time period to determine an effect of each food item, medication, and symptom on the metabolic state of the patient.

Additionally, the digital twin module 350 may implement one or more metabolic models to predict a patient's metabolic state that would result from the recommended nutrition, medication, or lifestyle changes included in a recommendation. Alternatively, the digital twin module 350 may receive biological data, for example sensor data and lab test data, as inputs to metabolic models to determine a patient's actual metabolic response to the patient data 420.

Each metabolic model is trained using a training dataset made up of large volumes of historical patient data and biological data recorded for a significant volume of patients, respectively. The training set includes daily metabolic inputs and corresponding daily metabolic outputs. Inputs, for example, include biological data 420 recorded for a current period of time (i.e., different foods, medication, sleep, exercise, etc.) and a patient's initial metabolic state before the patient data 420 was recorded (e.g., based on biosignals derived from sensor data and lab test data). Inputs measured by wearable sensors and lab tests or recorded manually by a patient may be encoded into a vector representation, for example a feature vector, that a machine-learned model is configured to receive. A feature vector comprises an array of feature values each of which represents a measured or recorded value of an input biosignal.

Outputs, for example, include the actual biological data 410, which represents biosignals characterizing a patient's metabolic health (i.e., blood glucose level, blood pressure, and cholesterol). These act as baseline models trained on historical data that can then be applied to new patients with metabolic issues needing treatment to make predictions about those new patients based on what the models have learned from historical patients. Once trained, the machine-learned model may be applied to predict new metabolic states for the new patients based on new combinations of biosignals to predict how a novel set of input biosignals would result in different output signals, for example lowering blood glucose to improve diabetes or lowering blood pressure to improve hypertension.

The models are continuously trained by feeding the input biosignals and metabolic state outcomes for existing and new patients into these models such that the models continue to learn and are continuously updated based on these new data points. For example, after a metabolic state model determines an aspect of a patient's true metabolic state for a time period, the digital twin module 350 may update a training dataset with the determined true metabolic state and a plurality of biosignals recorded during the time period that contributed to the true metabolic state. The metabolic state model(s) are periodically re-trained based on the updated training dataset. This continuously improves the model and allows it to accurately predict future metabolic states for each patient based on their biosignal inputs. In comparison, the metabolic state model is trained or re-trained/modified on a training dataset comprising the information described above for a particular patient.

Figure 7:
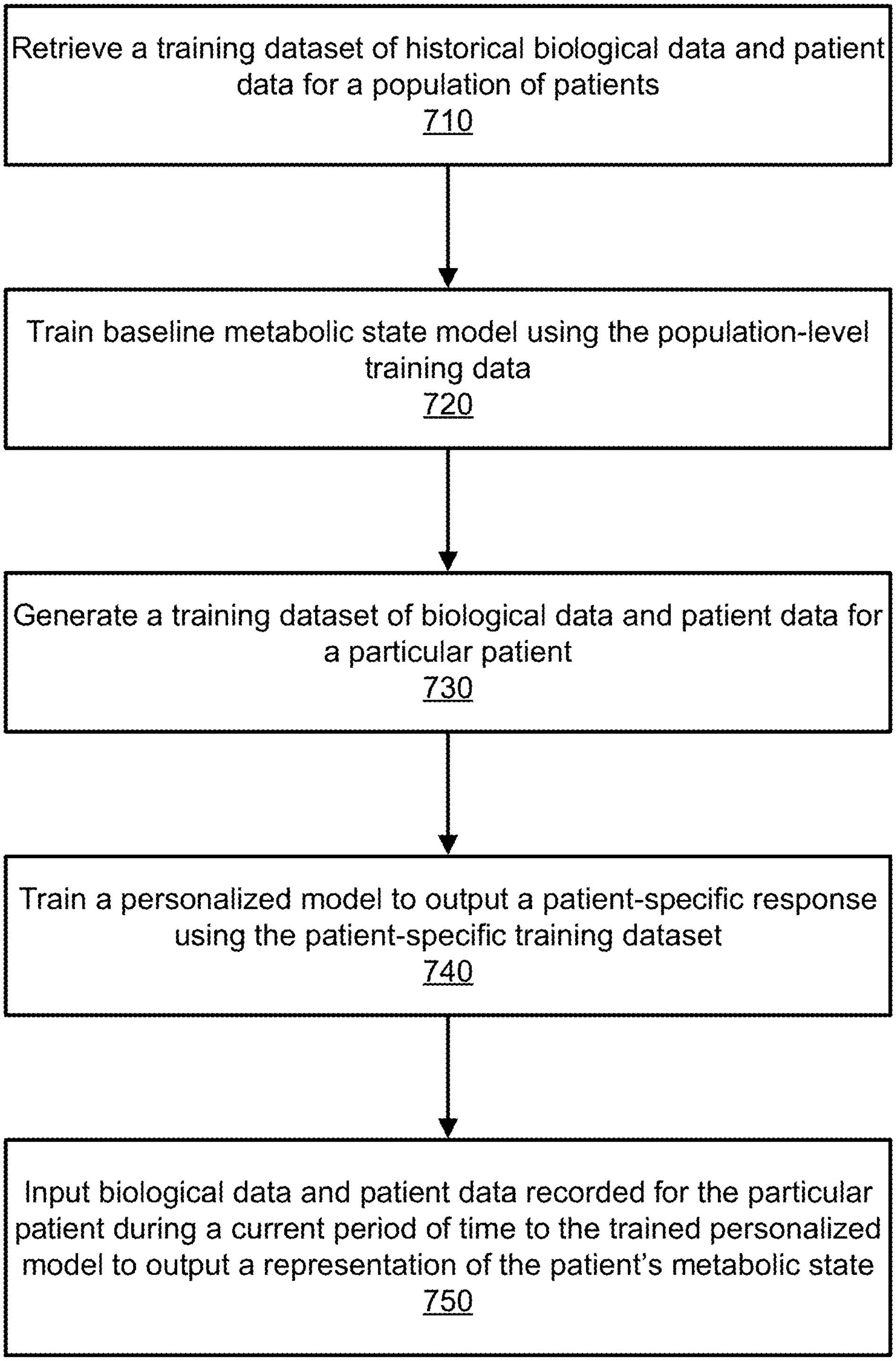
FIG. 7 is a flowchart illustrating a process for training a machine-learned model to output a representation of a patient's metabolic health, according to one embodiment.

FIG. 7 is an illustration of the process for training a machine-learned model to output an aspect of a patient's metabolic health, according to one embodiment. The digital twin module 350 retrieves 710 a training dataset comprised of historical biosignals (e.g., historical sensor data and lab test data) and patient measured and/or recorded for an entire population of patients. Each historical measurement of biological data and record of patient data is assigned a timestamp representing when the patient experienced the measurement/recording and a label identifying its impact on a patient's metabolic health, the patient's metabolic response to the measurement, or both. Using the training dataset of population-level data, the digital twin module 350 trains 720 a baseline model. The training dataset of population-level data comprises labeled metabolic states recorded for a population of patients and sensor data and lab test data that contributed to each labeled metabolic state. Once trained, the baseline model may be implemented to determine a metabolic state of a representative patient of the population of patients (e.g., an average patient) given a set of biological inputs, for example biological data or patient data.

In some implementations, the baseline model may be further trained to generate a personalized representation of a patient's metabolic health. In such implementations, the digital twin module 350 generates 730 an additional training dataset of biological data and patient data for a particular patient. The digital twin module 350 accesses both measured biological data and recorded patient data for a particular patient and aggregates that data into a training dataset. Similar to the historical training dataset, the biological data and patient data of the training dataset are assigned a timestamp and a label to characterize how each biological input impact the particular patient's metabolic state. Using the training dataset of patient-specific data, the digital twin module 350 trains 740 a personalized metabolic model. Once training, biological data and patient data recorded during a subsequent period of time may be input 750 to the trained model to output a representation of a particular patient's metabolic state.

Depending on the type of data input to either the personalized or baseline metabolic model, the digital twin module 350 may generate a representation of a patient's true metabolic state or their predicted metabolic state. Biological data, for example data recorded by a wearable sensor or a lab test, may be input to a model to generate a representation of a patient's true metabolic state consistent with the description above. Alternatively, patient data, for example nutrition data, medication data, symptom data, and lifestyle data, may be input to a model to generate a prediction of patient's current metabolic state consistent with the description above.

Training both models in such a manner enables the patient health management platform 130 to predict a patient's metabolic response to future input stimuli (i.e., patient data 420 recorded by a patient in the future) for not just patients already included in the training dataset, but also new patients included in a holdout dataset because the model only relies on the knowledge representing a patient's current metabolic state and the patient's input stimuli to predict their patient-specific response. Additionally, the model predicts a patient's response to input stimuli for each patient at different stages of his or her treatment because the platform maintains a history of a patient's changing metabolic condition. Finally, it allows for long-range precision prediction of the patient's metabolic state by using current and short-range predictions to inform longer-range predictions.

Figure 8:
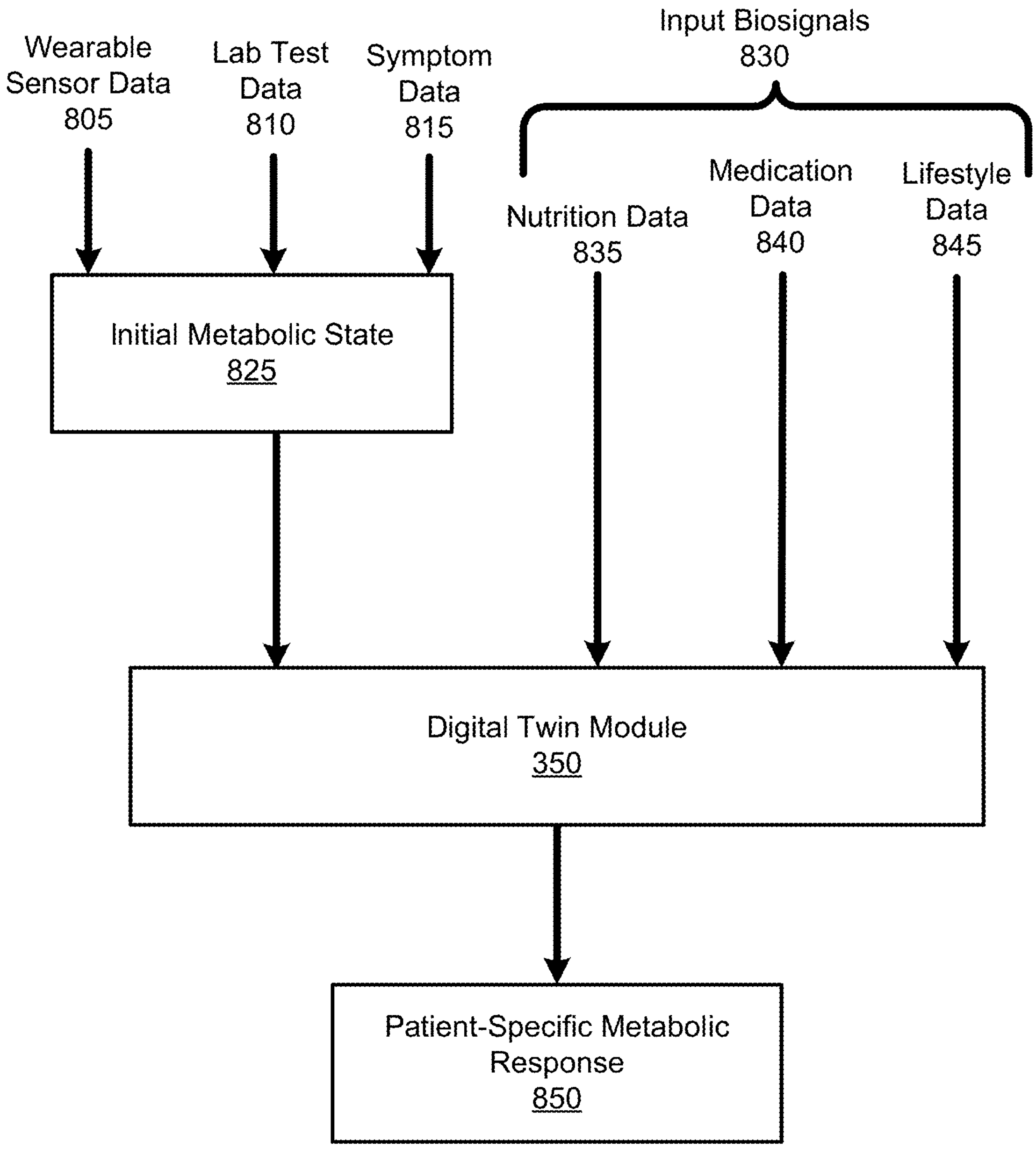
FIG. 8 is an illustration of the process for implementing a machine-learned model to predict a patient-specific metabolic response, according to one embodiment.

FIG. 8A is an illustration of the process for implementing a machine-learned model, according to one embodiment. For a given time period, biosignals recorded as wearable sensor data 805, lab test data 810, and symptom data 815 are representative of a patient's actual, current metabolic state. Accordingly, based on these input biosignals, the patient response module generates an initial metabolic state 825. When sufficient training data exists for a particular patient, the initial metabolic state 825 may be determined using a metabolic model(s). Alternatively, the initial metabolic state 825 may be determined using metabolic model(s) trained for a population of patients. Additionally, the digital twin module 350 relies on input biosignals 830, which represent biosignals that may impact a patient's metabolic state, either deteriorating or improving the state. For example, input biosignals 830 may include nutrition data 835, medication data 840, and lifestyle data 845 recorded for a patient at a time occurring after the generation of the initial metabolic state. In addition to the initial metabolic state 825, the digital twin module 350 receives the input biosignals 830 recorded by the patient as inputs one or more metabolic models. Accordingly, digital twin module 350 models the patient's patient-specific metabolic response 850 to the inputted biosignals. Described differently, the patient-specific metabolic response 850 represents one or more changes in a patient's initial metabolic state caused by, or at least correlated with, the input biosignals 830.

For a second time period following the determination of the patient-specific metabolic response 850, the platform 130 continues to record wearable sensor data 805, lab test data 810, and symptom 815. Given biosignals recorded as wearable sensor data 805 and lab test data 810 as inputs, the aggregated output of the combination of metabolic models (e.g., the true metabolic state) describes what a patient's metabolic response actually is during a time period. Given nutrition data, 835, medication data 840, and lifestyle data 845 (e.g., input biosignals 830) recorded during the same time period as inputs, the aggregated output of the combination of metabolic models (e.g., the predicted metabolic state) describes what a patient's metabolic response should be during the time period. Accordingly, a comparison of the two outputs allows the platform 130 to verify the timeliness, accuracy, and completeness with which a patient recorded the input biosignals 830.

IV.D. 1 Example Glucose Impact Model

One example of a machine-learned model is a glucose impact model. The glucose impact model described herein is an embodiment of a metabolic model that may be implemented by the glucose twin module 615. The glucose impact model is trained to generate a prediction of a patient's metabolic state based on a training dataset of previous metabolic states of the patient and history of recorded patient data contributing to each previous metabolic state. The glucose impact model generates patient-specific, blood-glucose peak predictions and transforms those predictions into a relative glucose impact of an individual food item (e.g., food items recorded as nutrition data) on a patient's blood glucose levels. Such insight enables a patient, or alternatively a TAC manager 470 associated with the platform 130, to study and learn how various foods which have been previously consumed by the patient and have not yet been consumed by the patient affect their blood glucose. Additionally, the recommendation module 355 may recommend specific foods consistent with the most recent insights generated by the model.

In an example implementation, the glucose impact model has a label 'glucoseMax', and input features including, but not limited to, 'calories', 'carb', 'protein', 'fat', 'fibre', 'glycemicIndex', 'quantity', 'glucoseBaseline', 'efficiency', 'minutesAsleep', 'minutesAwake', 'activityCalories', 'marginalCalories', 'caloriesBMR', 'caloriesOut', 'steps', 'fairlyActiveMinutes', 'lightlyActiveMinutes', 'veryActiveMinutes', 'sedentaryMinutes', 'weight', 'height', 'hba1cValue', 'GLICLAZIDE', 'GLIMEPIRIDE', 'METFORMIN', 'OXRA', 'SULFONYLUREA', 'mealType_AFTERNOON_SNACK', 'mealType_BREAKFAST', 'mealType_DINNER', 'mealType_LUNCH', 'mealType_MORNING_SNACK', 'bmiDerived', 'netCarb', 'glycemicLoad', 'netGICarbs'.

Wearable sensors (e.g., continuous glucose monitors) record blood glucose data continuously over a period of time to characterize feature values for 'glucoseBaseline' and 'glucoseMax'. Feature values for 'efficiency', 'minutesAsleep', 'minutesAwake', 'activityCalories', 'marginalCalories', 'caloriesBMR', 'caloriesOut', 'steps', 'fairlyActiveMinutes', 'lightlyActiveMinutes', 'veryActiveMinutes', and ‘sedentaryMinutes’ may be recorded by a different wearable sensor, for example an activity tracker. Feature values for ‘weight’, ‘height’, and ‘hbalcValue’ are all captured or calculated from lab test data, for example tests performed during a doctor’s visit. Feature values for ‘GLICLAZIDE’, ‘GLIMEPIRIDE’, ‘METFORMIN’, ‘OXRA’, ‘SULFONYLUREA’ are captured from the medication history, i.e. the types, dosages, and timings of medicines taken by the patient throughout the treatment. Feature values for ‘quantity’, ‘mealType,’ ‘AFTERNOON_SNACK’, ‘mealType_BREAKFAST’, ‘mealType_DINNER’, ‘mealType_LUNCH’, ‘mealType_MORNING_SNACK’, are manually recorded by a patient as they consume food items (i.e., nutrition data). For specific food items recorded by a patient, features values for ‘calories’, ‘carb’, ‘protein’, ‘fat’, ‘fibre’, ‘glycemicIndex’, ‘netCarb’, ‘glycemicLoad’, ‘netGICarbs’ are accessed from the nutrition database 140 or determined using the nutrition data module 440.

In one specific embodiment, the patient response module implements gradient boosting techniques to model a patient’s metabolic response (e.g., a GradientBoostingRegression from the Sci-Kit Library or the XGBoostRegressor from the XGBoostLibrary). Gradient Boosting creates an n number of weak learners, hereafter referred to as “trees,” where each new tree is made with the goal of reducing the error from the combination of learners that came before it. Most commonly, the model is trained on 80% of the patient data after cleaning and filtering chosen at random through the entire history of the data and is validated on 20% of the data after cleaning and filtering, chosen at random throughout the entire history of the data. The model predicts glucose peaks (‘glucoseMax’) which are found by max peak within meal time windows. Those max peaks are normalized and the platform used gradient boosted regression to predict the glucoseMax labels. In optimized embodiments, the model achieves accuracy metrics of RMSE (room mean squared error) of less than 24.6, MAE (Mean Absolute Error) of less than 17.2, MeAE (Median Absolute Error)=13.3, and 91% of all predictions within 40 points of the actual value.

From the predicted max peaks, the patient response module subtracts the lowest peak predicted food item from the peaks of the remaining food items to determine the relative impact of each food item on the blood glucose level for that patient. Because these predictions are personalized based on a patient’s biometrics, medications, lifestyle, and nutrition data which they consumed, the impact of each food item is highly specific to an individual patient. The measured glucose impact is normalized relative to a “glucoseBaseline” for the patient, which is defined as the lowest 10% value of the distribution of the data for the previous 24 hours. The glucose impact is penalized (increased) as medications increase because the glucose impact is a relative food peak around the baseline and medications may artificially reduce the glucoseBaseline and the impact of particular foods.

The patient health management platform 130 may classify foods based on their patient-specific glucose impact. Individual foods may be categorized based on their impact on metabolism relative to thresholds established for the general population, for example a first category of food items are recommended to the particular patient, a second category of food items should be sparingly consumed by the patient, and a third category of food items should be avoided altogether by the patient.IV.D.2 Example 1DG Model Another example of a machine learned model is a 1DG model which predicts a patient’s resulting 1-Day Average Glucose (i.e., a person’s average blood glucose level over a 24-hour calendar day) given the patient’s starting metabolic state and the record of food items consumed by the patient over 1 or more days (e.g., nutrition data). The 1DG model described herein is an embodiment of a metabolic model that may be implemented by the glucose twin module 615 either instead of or in combination with the glucose impact model describe in Section IV.C.1. The model is trained to generate a prediction of the metabolic state of the patient based on an average blood glucose level of the patient over a 24-hour calendar day given a metabolic profile of the patient and foods consumed by the patient. For example, if a patient adheres to a 7-day long nutrition recommendation outlining particular food items to be eaten as breakfast, lunch, dinner, and snacks during those seven days, the digital twin module 350 is used to predict the patient’s 1DG progression over those seven days.

A patient’s initial metabolic state is determined based on features including, but not limited to, HBa1c, fasting glucose, minutes asleep/awake, sleep efficiency, sedentary minutes, calories BMR, BMI, calories output, exercise calories output, metformin dosage, glimepiride dosage. Nutrition data including, but not limited to, protein, fat, carbohydrates, fiber, net carbohydrates, net glycemic index carbs, calories, and glycemic load for each recorded food item, as well as derived features created as ratios between nutrients. Features representing ratios of nutritional to personal information are used as well. A highly parallelized optimization algorithm is used to find the optimal combination of features for model performance.

In one specific embodiment, the 1DG model implements gradient boosting techniques to predict a patient’s 1DG and their resulting fasting glucose for the first day given all the metabolic features and food features (e.g., a GradientBoostingRegression from the Sci-Kit Library or the XGBoostRegressor from the XGBoostLibrary) in combination with a patient cohorting algorithm. The cohorting algorithm selects discrete subpopulations from the entire universe of patients based on their respective relative metabolic similarity. Separate gradient boosting models are subsequently trained on each of these subpopulations. Gradient Boosting creates an n number of weak learners (trees in our case), where each new tree is made with the goal of reducing the error from the combination of learners that came before it. Most commonly, the model is trained on 80% of the patient data after cleaning and filtering chosen at random through the entire history of the data and is validated on 20% of the data after cleaning and filtering, chosen at random throughout the entire history of the data. In optimized embodiments, the model achieves an accuracy MeAE (Median Absolute Error) of less than 3.5.

Using the 1DG measurement and the fasting glucose measured from the previous day, the 1DG model predicts the 1DG measurement and fasting glucose for the second day. The model iteratively repeats the process from Day n to Day n+1 to predict the IDG progression for each day included in a patient’s nutrition recommendation. In optimized embodiments, the model achieves an accuracy MeAE of less than 6.0 over a 14 day sequence. Based on these personalized predictions, coaches or medical professionals are enabled to understand the impact of a given nutrition recommendation on a patient’s metabolic state and modify the recommendation to achieve the best predicted outcome for the patient. Accordingly, the digital twin module 350 and a coach may collaborate to create a patient-specific nutrition recommendation that significantly reduces a patient’s blood glucose levels to treat their diabetes. The 1DG model described above may also be used to improve a patient’s overall experience using the patient health management platform. In the event that a continuous glucose monitor becomes defective or a patient opts out of wearing a glucose monitor, the 1DG model may be used as an effective replacement for the continuous glucose monitor once it is trained to generate accurate predictions over long timespans.

IV.E Patient-Specific Recommendations

The recommendation module 355 may include a combination of rule-based artificial intelligence techniques representing codified medical knowledge from established medical practice (e.g., American Diabetes Association guidelines, research literature, and insights gained from past medical treatments). The recommendation module 355 applies the codified knowledge in an automated manner to recommend treatments for new patients using the patient health management platform 130.

The platform 130 additionally categorizes patients into a cohort with other patients with similar metabolic profiles. The recommendation module 355 applies a system of rule to assign patients with a similar metabolic profile to the same cohort. The recommendation module 355 then tailors a specific treatment recommendation (i.e., a combination of nutrition and medication regimens) for the metabolic profiles of patients in each cohort. In some implementations, the recommendation module 355 generates a representative metabolic profile for each cohort based on an average of the metabolic profiles for each patient in cohort or an aggregate of the metabolic profiles for each patient in cohort. The rule-based intelligence applied to categorize patients in cohorts is based on biosignals characterizing a patient's metabolic state or general health, for example biosignals recorded by wearable sensors or measured using lab tests. Specific examples of such cohorting rules include, but are not limited to, BMI, 5-day average blood glucose ("5DG"), 5-day average of grams of net carbs eaten per day ("5dgnc"), 5-day average of the number of >50 mg/dL blood glucose spikes per day ("5dspike"), ketone levels, and whether the patient is taking medications like glimepiride.

Each cohorting rule is applied to a patient's metabolic profile to categorize a patient into either a cohort that complies with the cohorting rule or a cohort that does not comply with the rule. Cohorting rules may be codified in a binary format, for example a patient either satisfies the rule and is sorted into a first cohort or does not satisfy the rule and is sorted into a second cohort. In alternate implementations, a rule may be divided into several ranges of measurements, for example BMI=0 to 22, BMI=23 to 50, BMI=50+. In such implementations, each range of measurements may be associated with a particular cohort such that a patient with measurements falling within a particular range is assigned to a particular cohort.

Rules may be iteratively applied to a patient. For example, a first rule (Rule 1) may be applied to categorize a patient into a first cohort (Cohort A) or a second cohort (Cohort B). A patient whose metabolic state or health does not comply with the first rule may be placed into Cohort B. A second rule may be applied to further categorize a patient into either Cohort B1 or Cohort B2. A patient whose metabolic state or health does comply with the second rule may be placed into Cohort B1. Accordingly, when applied, each rule allows the recommendation module 355 to characterize, both in greater detail and in greater specificity, a patient's metabolic state or health.

In addition to cohorting rules, the recommendation module 355 may apply a system of rules to make a medication recommendation for a patient or cohort of patients. In particular, the recommendation module 355 applies a set of medication rules to recommend a particular combination of medications (i.e., a comprehensive medication treatment regimen) based on biosignals such as HbA1c levels, 5-day average blood glucose ("5DG"), recent trends in blood glucose (i.e., increases or decreases in blood glucose), creatine levels, BMI measurements, and previously taken medications.

Consistent with the description above of cohorting rules, each medication rule may be codified into a binary format, for example a patient satisfying a condition or plurality of conditions should be prescribed a particular medication or combination of medications, whereas a patient that does not satisfy the condition or plurality of conditions should not be prescribed the particular medication or combination of medications. In addition to being applied to individual patients, medication rules may be applied in conjunction with cohorting rules, for example certain cohorts of patients may be eligible or ineligible for certain medications. In such implementations, each medication rule is compared to a representative health profile for patients in a cohort to determine whether the medication rule applies to the cohort or not. For example, in the example illustrated by FIG. 9, cohort B comprises patients with BMI<22. A medication, for example medication A, may only be safely taken by patients with BMI>22. Accordingly, the recommendation module 355 may apply a medication rule for medication A to both cohort B comprised of patients with BMI<22 and cohort A comprised of patients with BMI>22 to determine that patients in cohort A may safely take mediation A, but patients in cohort B may not. For patients in cohort B, the recommendation module 355 generates an alternative medication or treatment regimen with the same effects as medication A.

More information regarding cohorting rules and rule-based classifiers implemented by the recommendation module 355 can be found in U.S. patent application Ser. No. 16/993,177, filed on Aug. 13, 2020, which is incorporated by reference herein in its entirety.

V. Digital Twin Clinical Trial Simulator

As discussed above, conventional clinical trials for validating nutrition-based treatment recommendations require significant amounts of time, resources, and costs.

Figure 9:
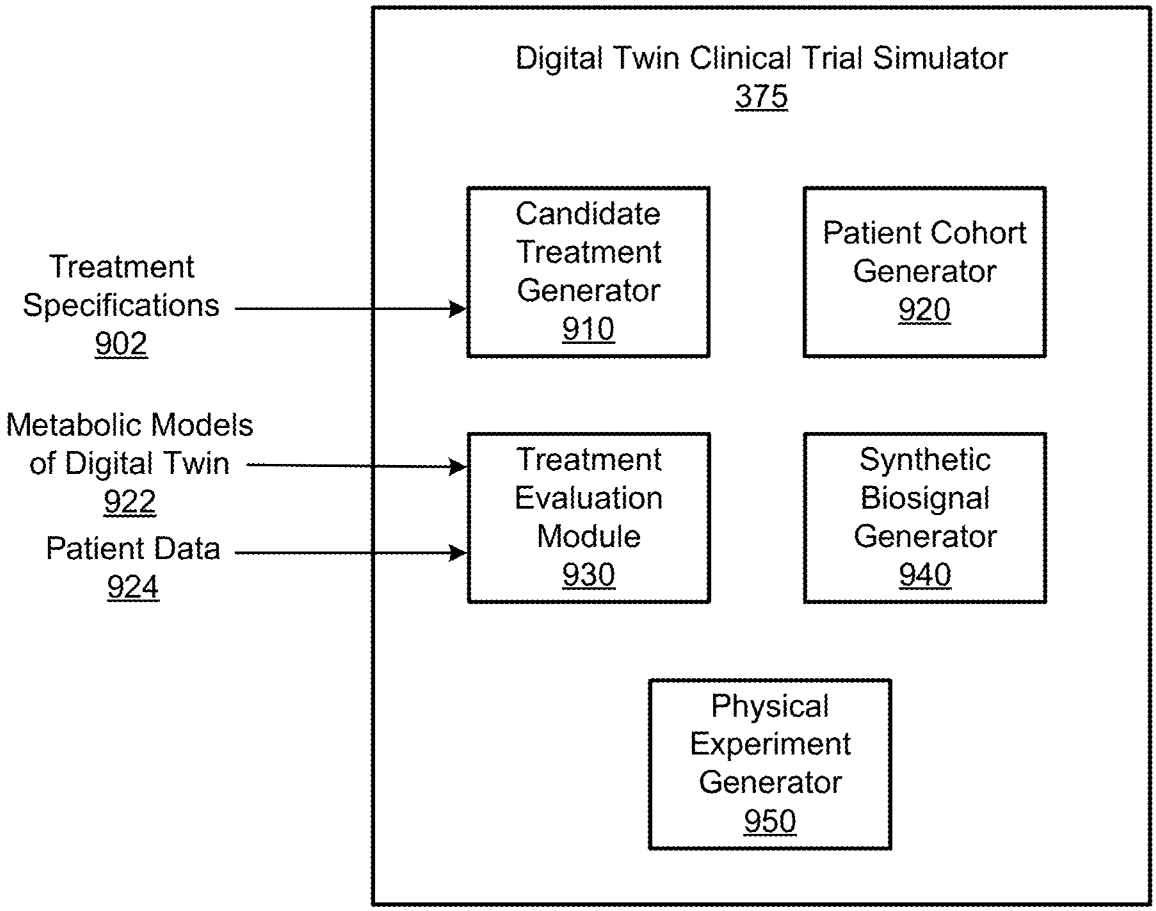
FIG. 9 is a block diagram of the system architecture for a simulator, according to one embodiment.

Accordingly, the Digital Twin clinical trial simulator 375 leverages the digital representations of patients' metabolic state generated and updated by the patient health management platform 130 to evaluate the efficacy of a candidate treatment recommendation. To more closely simulate clinical trials manually performed across a population of patients, the Digital Twin clinical trial simulator 375 identifies a cohort of patient's sensitive to a particular candidate treatment and determines the effect of each candidate treatment recommendation using the personalized metabolic models of each patient in the cohort. FIG. 9 is a block diagram of the system architecture for a Digital Twin clinical trial simulator 375, according to one embodiment. The Digital Twin clinical trial simulator 375 comprises a candidate treatment generator 910, a patient cohort generator 920, a treatment evaluation module 930, a synthetic biosignal generator 940, and a physical experiment generator 950. However, in other embodiments, the patient health management platform 130 may include different and/or additional components.

A provider may interact with the Digital Twin clinical trial simulator 375 independent of the patient health management platform 130 to evaluate whether candidate treatment recommendations address or improve a particular metabolic state, metabolic condition, or aspect of metabolic health (e.g., a deficiency in a particular nutrient). Alternatively, the Digital Twin clinical trial simulator 375 may receive a novel treatment recommendation generated by the patient health management platform 130 to improve or maintain the metabolic state of a particular patient. In such situations, rather than simulating an entire clinical trial, the Digital Twin clinical trial simulator 375 may leverage techniques described herein to evaluate the effectiveness of the candidate treatment recommendation for a particular patient or group of patients.

The candidate treatment generator 910 receives treatment specifications 902 from a provider identifying a target to be accomplished, at least one intervention parameter to be adjusted across candidate treatment recommendations for accomplishing the target, and a domain of patient data upon which to generate candidate treatment recommendations. As described herein, the target refers to a particular aspect of metabolic health to be improved. As described herein, an intervention parameter refers to a measurable biosignal or recordable aspect of patient data, which may be adjusted or manipulated to affect a patient's metabolic state. Examples of such intervention parameters include, but are not limited to, macronutrients, micronutrients, biota nutrients, activity habits, and sleep cycles. As described herein, a "domain" of data refers to all input parameters available for the candidate treatment generator 910 to measure in evaluating the efficacy of candidate treatment recommendations. The domain may be defined as all biosignal and patient data inputs or may be specified to only include patient data such as nutrition, sleep, and activity.

For example, a provider may define the target as "diabetes reversal" and an intervention parameter as daily nutrition. A first candidate treatment recommendation may instruct a patient to consume a cup of rice daily and predict their blood glucose response while a candidate treatment recommendation may instruct a patient to consume a cup of rice and half an avocado daily and predict their blood glucose response. Accordingly, the candidate treatment generator 910 generates various candidate treatment recommendations for reversing diabetes, where each candidate treatment recommendation includes a different adjustment to the intervention parameter. Depending on the significance of a particular intervention parameter to a given target, one candidate treatment recommendation may be more effective in achieving the target than another.

Given the vast number of potential biosignals and patient data inputs affecting a patient's metabolic state, for example the biosignal inputs listed in Table 1, the candidate treatment generator 910 generates a large number of candidate treatment recommendations (e.g., hundreds or thousands of candidate treatment recommendations at a time) for accomplishing a given target, rendering conventional manual clinical trials infeasible. In embodiments where the treatment specifications 902 specify a single intervention parameter, the candidate treatment generator 910 may generate multiple candidate treatment recommendations. For example, where the treatment specifications 902 identify "folate consumption" as an intervention parameter, the candidate treatment generator 910 may generate a variety of meal plans with increased folate. As another example, where the treatment specifications 902 identify "light activity minutes," the candidate treatment generator 910 may generate lifestyle recommendations with a distribution of increased "light activity minutes."

Considering another example of "hypertension reversal," some candidate treatment recommendations may include specific meal plans with instructions for consuming different combinations of macronutrients, micronutrients, and biota nutrients. Other candidate treatment recommendations may include specific activity recommendations, for example different types of exercises to improve endurance, balance, strength, and flexibility. Other candidate treatment recommendations may call for sleep adjustments with different techniques to improve sleep duration and quality. More specifically, the candidate treatment generator 910 may generate candidate treatment recommendations based on a domain of data including nutrition data, sleep data, activity/lifestyle data and intervention parameters including consumption of numerous macronutrients, micronutrients, biota nutrients, activities and sleep patterns. The effectiveness of each candidate treatment recommendation may be evaluated based on changes in the patient's blood pressure measurement (e.g., the "target" specified in the treatment specification 902).

Additionally, as will be discussed below with regards to the physical experiment generator 350, the Digital Twin clinical trial simulator 375 may identify a subset of the most effective candidate treatment recommendations, for example candidate treatment recommendations that satisfied a threshold improvement in the metabolic state of a patient. The Digital Twin clinical trial simulator 375 may identify which intervention parameters were adjusted in the most effective candidate treatment recommendations and generate an aggregate treatment recommendation that adjusts all (or a subset) of the identified intervention parameters simultaneously or sequentially to improve the given outcome.

For each candidate treatment generated by the candidate treatment generator 910, the patient cohort generator 920 identifies sensitive cohorts of patients from a larger population of current patients using the patient health management platform 130 and past patients who used the patient health management platform 130. As described herein, the sensitivity of a patient to a candidate treatment recommendation describes the likelihood that adjustments to the intervention parameter specified in the candidate treatment recommendation will improve the metabolic state of the patient. In some embodiments, a patient may be classified as sensitive to a candidate treatment recommendation if there is at least a threshold likelihood that the candidate treatment recommendation will improve the metabolic state of the patient.

To determine the sensitivity of each patient in the population of patents to a given intervention parameter, the patient cohort generator 920 identifies correlations for the patient between changes in their metabolic state and adjustments to a particular intervention parameter. Patients sensitive to the intervention parameter may experience a significant improvement (e.g., a threshold improvement) in their metabolic health or a significant deterioration (e.g., a threshold deterioration) in their metabolic health when the intervention parameter is adjusted (e.g., increased, decreased, or varied). A patient data store (not shown) stores correlations identified between each patient and each intervention parameter. The patient data store may additionally store labels for each patient of the population of patients describing the sensitivity of the patient to one or more intervention parameters. The labels may identify particular intervention parameters to which the patient is sensitive. Accordingly, the patient cohort generator 920 identifies one or more intervention parameters adjusted in the recommendation and generates a cohort of patients sensitive to each intervention parameter identified in the candidate treatment recommendation based on data stored in the patient data store 430. In some embodiments, the patient cohort generator 920 generates the cohort of patients by narrowing the population of patients down to a subset patients who have not yet improved their metabolic health to a particular category or classification of metabolic health, for example patients suffering from hypertension or patients whose metabolic state may still be improved, and identifies the cohort of sensitive patients from the subset of patients.

In some embodiments, the patient cohort generator 920 analyzes an individual patient's historical changes in their metabolic state and determines whether adjustments to a particular intervention parameter have had long-term effects on the patient's metabolic state. For example, the glucose twin module 615 may predict that adjustments to a given intervention parameter may only temporarily improve a patient's glucose levels before the patient's glucose levels return to an unhealthy level. In such circumstances, the patient cohort generator 920 may exclude the patient from consideration when generating the cohort of patients. In some embodiments, a candidate treatment recommendation may include instructions for a patient to increase consumption of a particular food item. Patients sensitive to increased consumption of the food item are expected to experience a significant improvement in their metabolic health or a significant deterioration in their metabolic health. Patients who are not sensitive to the food item will experience no significant changes in their metabolic health.

Accordingly, the patient cohort generator 820 analyzes correlations between a patient's historical consumption of the food item and changes in their metabolic state to separate the population of patients into a first subset of patients sensitive to the intervention parameter and a second subset of patients insensitive to the intervention parameter. The patient cohort generator 920 may identify patients in the first subset by comparing historical changes in the patient's metabolic health (e.g., glucose measurements, blood pressure measurements) caused by previous adjustments to the intervention parameter to a threshold change. If the historical change(s) satisfies the threshold change, the patient cohort generator 920 labels the patient as sensitive. If the historical change(s) does not satisfy the threshold change, the patient cohort generator 920 labels the patient as insensitive. Once the patient cohort generator 920 labels a patient as sensitive or insensitive to an intervention parameter, the patient data store may store and assign label to the patient in the patent data store to be referenced in future implementations of the Digital Twin clinical trial simulator 375. The patient cohort generator 920 reviews the correlations or labels stored in the patient data store 430 to identify a cohort of patients sensitive to the candidate treatment recommendation. Sensitivity labels assigned to a patient may be periodically reevaluated to confirm whether a patient continues to be or is no longer sensitive to a particular intervention parameter.

In alternate embodiments, the patient cohort generator 920 implements multiple thresholds to classify the population of patients into tiers of sensitivity to an intervention parameter, for example "highly sensitive," "moderately sensitive," and "insensitive." The patient cohort generator 920 generates the cohort of patients by adding patients in the most sensitive tier of patients and may optionally add patients in other tiers until the cohort of patients includes a threshold number of patients or includes a threshold volume of patient data.

In embodiments where a candidate treatment recommendation generated by the generator 910 includes instructions for adjusting multiple intervention parameters, the patient cohort generator 920 may determine the sensitivity of each patient in the population to each intervention parameter adjusted in the candidate treatment recommendation. Additionally, the patient cohort generator 920 may aggregate the sensitivity of the patient to each intervention parameter to determine an overall sensitivity of the patient to the candidate treatment recommendation. The patient cohort generator 820 may determine the overall sensitivity of the patient by averaging the sensitivity determined for each intervention parameter or using any other suitable technique.

In some embodiments, the patient cohort generator 920 categorizes the population of patients based on current metabolic states. Continuing from the hypertension example discussed above, the patient cohort generator 920 classifies the population of patients into patients at particular stages of hypertension, namely Normal, Elevated, Hypertension Stage 1, Hypertension Stage 2, and Hypertensive Crisis (as defined by the American Heart Association). The patient cohort generator 920 may additionally apply the techniques discussed above to patients in a particular category to focus the evaluation of candidate treatment recommendations on patients in a particular category of metabolic state. In one embodiment, the patient cohort generator 920 determines an effect of a candidate treatment recommendation on a category of patients by predicting an effect of the candidate treatment recommendation on each patient in the category. The patient cohort generator 920 determines an overall sensitivity of the category to the candidate treatment recommendation by aggregating the effect of the candidate treatment recommendation predicted for each patient in the category, for example by averaging or any other suitable technique.

The patient cohort generator 920 separates the generated cohort of patients into a control cohort and a test cohort. In selecting patients for the control cohort and the test cohort, the patient cohort generator 920 maintains a similar distribution of patients in both the control and test cohorts. For example, the patient cohort generator 920 may organize patients such that both the control and test cohorts comprise a nearly equal distribution of members in the same age groups (e.g., 25-35, 35-45, 45-65, and 65 and older), similar ethnicities, similar distribution between BMI and diet preferences (e.g., members with height, weight, and diet preferences), similar distribution between the stage of hypertension (e.g., Normal, Elevated, Stage 1, Stage 2, and Hypertensive Crisis), similar blood pressure ranges, or similar medications. If the physical experiment generator 950, further discussed below, selects a candidate treatment recommendation to be executed as a physical experiment, the physical experiment generator 950 may include the patients identified in both the control and test cohorts with the instructions for performing the physical experiment.

The treatment evaluation module 930 leverages the techniques discussed above with regards to the digital twin module 350 and patient-specific metabolic models described in Section IV.D to evaluate the effectiveness of each candidate treatment recommendation generated by the candidate treatment generator 910. To simulate a clinical trial, the treatment evaluation module 930 determines the effectiveness of each candidate treatment recommendation generated by the candidate treatment generator 910 for the cohort of patients identified by the cohort generator 920. The treatment evaluation module 930 evaluates the effect of the candidate treatment recommendation on the metabolic state of each patient in the test cohort and compares the affected metabolic states to the unaffected metabolic states of patients in the control cohort. Because patients in the control cohort represent metabolic states unaffected by the candidate treatment recommendation and patients in the test cohort represent metabolic states affected by the candidate treatment recommendation, the treatment evaluation module 930 may determine the effect of a candidate treatment recommendation on the cohort of patients.

To determine the effect of a candidate treatment recommendation on metabolic states of patients in the test cohort, the treatment evaluation module 930 encodes the candidate treatment recommendation into a feature vector representation and inputs the feature vector representation into the patient-specific metabolic models of the digital twin module 350 for each patient of the test cohort. Accordingly, the digital twin module 350 of each patient in the test cohort outputs a metabolic state of the patient representing a prediction of the effects of the patient's adherence to the candidate treatment recommendation. In some embodiments, the treatment evaluation module 930 determines a representative affected metabolic state based on the outputs of the patient-specific metabolic model of each patient in the test control. The treatment evaluation module 930 may additionally determine a representative control metabolic state based on metabolic states of patients in the control cohort. The treatment evaluation module 930 may determine the effect of the candidate treatment recommendation by comparing the representative affected metabolic state determined from the test cohort to the representative control metabolic state determined from the control cohort.

As discussed above, the digital twin module 350 comprises a plurality of patient-specific metabolic models, each of which is trained to predict a change in particular aspect of a patient's metabolic state. For example, metabolic models of the glucose twin module 615 predict a change in a patient's glucose levels based on a candidate treatment recommendation, whereas metabolic models of the blood pressure twin module 620 predict changes in a patient's systolic and diastolic blood pressure based on a candidate treatment recommendation. Accordingly, for each patient in the test cohort, the treatment evaluation module 930 accesses each metabolic model of the patient's digital twin (e.g., the digital twin module 350) and patient data describing the patient's current metabolic state. The treatment evaluation module 930 implements each of the accessed metabolic models to generate a holistic prediction of the impact of a candidate treatment recommendation on the patient's metabolic state.

In some embodiments, the treatment evaluation module 930 accesses the training dataset(s) upon which the metabolic models were initially trained. The treatment evaluation module 930 may process the training dataset to filter anomalous data points. For example, in a training dataset of continuous glucose measurements (upon which metabolic models of a patient's glucose twin module 615 are trained), the treatment evaluation module recognizes that when a patient first begins to use a wearable sensor, the recorded sensor data must stabilize over an initial time period. Accordingly, the treatment evaluation module 930 may exclude sensor data recorded during the first and last day on which the sensor was used from the training dataset and re-trains the metabolic models based on the updated training dataset. In one embodiment, the treatment evaluation module 930 identifies anomalous data points using data validation techniques and data quality checks to determine whether the range of CGM readings are too high or too low, for example during an initialization period of glucose readings. In another embodiment, the treatment evaluation module 930 identifies anomalous data points based on standard deviations from the mean, for example two or three standard deviations away from the mean. In yet another embodiment, the treatment evaluation module 930 implements supervised and unsupervised machine learning models to identify and remove anomalous data points.

The treatment evaluation module 930 may implement the accessed metabolic models in a serial manner according to known dependencies between the intervention parameter of the candidate treatment and components of the digital twin module 350 and dependencies between components of the digital twin module 350. To begin, the treatment evaluation module 930 identifies a metabolic model (also referred to as a "primary model" of the digital twin) whose output would be most directly affected by the intervention parameter. The treatment evaluation module 930 may determine the primary metabolic model based on the treatment being simulated by the Digital Twin clinical trial simulator 375. In addition to, or in the alternative, the digital twin clinical trial simulator 375 may consider features of metabolic health that are measured to validate the effect of an intervention parameter of the candidate treatment recommendation. For example, to measure the effect of certain nutrition plan on Postprandial glucose response, the treatment evaluation 930 identifies the glucose twin module 615 as the primary metabolic model. Similarly, to evaluate candidate treatment recommendations providing intervention parameters for Hypertension reversal, the blood pressure twin module 620 may be identified as the primary metabolic model.

For example, a candidate treatment recommendation may identify "potassium levels" as an intervention parameter and instruct a patient to increase potassium in their diet. Recognizing that changes in potassium levels directly impact a patient's blood pressure levels, the treatment evaluation module 930 inputs the feature vector representation of the candidate treatment recommendation to the blood pressure twin module 620 to predict a change in the patient's blood pressure level. Next, the treatment evaluation module 930 identifies one or more "secondary models" of the digital twin module 620 whose predictions would be affected by the prediction generated by the primary component of the digital twin module. Continuing from the example above regarding "potassium levels," a prediction generated by the liver twin module 640 may be dynamic given fluctuations in a patient's blood pressure. Accordingly, the treatment evaluation module 930 inputs the blood pressure predictions generated by the blood pressure twin module 620 and the feature vector representation of the candidate treatment recommendation to the liver twin module 640 to predict an accurate representation of the patient's liver function. The techniques discussed above may be iteratively performed for any remaining components of the digital twin module 350 until the treatment evaluation module 930 generates a holistic prediction of the patient's metabolic state based on the candidate treatment recommendation.

To describe the effectiveness of the candidate treatment recommendation across the test cohort of sensitive patients, the treatment evaluation module 930 may determine a representative effect of the candidate treatment recommendation based on the predicted metabolic state generated for each patient in the test cohort. For example, the treatment evaluation module 930 may compare the predicted metabolic state of each patient in the test cohort to the most recently measured true metabolic state of the patient (e.g., the current metabolic state of the patient) to determine a change (e.g., a difference) between the two. An improvement from the most recent true metabolic state to the predicted metabolic state may be characterized as a positive value, while a deterioration from the most recent true metabolic state to the predicted metabolic state may be characterized as a negative value. To determine the representative effect, the treatment evaluation module 930 may determine an average change between the current, true metabolic states and future, predicted metabolic states, or any other suitable metric, and evaluate the effectiveness of the candidate treatment recommendation based on the representative effect.

In one embodiment, the treatment evaluation module 930 determines the effectiveness of a candidate treatment recommendation based on the effect that adherence to the candidate treatment recommendation has on a patient's glucose levels. Accordingly, the treatment evaluation model 930 inputs the feature vector representing the candidate treatment recommendation into patient-specific metabolic models of the glucose twin module 615, for example the Glucose Impact Model and 1DG Model discussed in Section IV.D. More information regarding metabolic models implemented by the glucose twin module 615 can be found in U.S. patent application Ser. No. 17/243,470, filed on Apr. 28, 2021, which is incorporated by reference herein in its entirety.

In one embodiment, the treatment evaluation module 930 determines the effectiveness of a candidate treatment recommendation based on the effect that adherence to the candidate treatment recommendation has on a patient's systolic and diastolic blood pressure levels. Accordingly, the treatment evaluation model 930 inputs the feature vector representing the candidate treatment recommendation into patient-specific metabolic models of the blood pressure twin module 620. More information regarding metabolic models implemented by the blood pressure twin module 620 can be found in U.S. patent application Ser. No. 17/243,473, filed on Apr. 28, 2021, which is incorporated by reference herein in its entirety.

In some embodiments, the synthetic biosignal generator 940 may identify aspects of biosignal data or patient data for which a below threshold amount of data has been collected or is available. The synthetic biosignal generator 940 determines the strength of a correlation between a cohort of patients or a particular feature of patient data or biosignal data and an intervention parameter (or combination of intervention parameters) prescribed by candidate treatment recommendation and compares the determined strength to a confidence interval. If the determined strength of the correlation is less than the confidence interval, the synthetic data generator 940 generates synthetic data using any suitable technique, for example Generative Adversarial Network (GAN) based technique. The Digital Twin clinical trial simulator 375 updates the patient data store 430 with generated synthetic data and repeats the techniques and processes discussed above to validate the candidate treatment recommendation with consideration of the updated synthetic data. As the patient data store 430 is updated with the synthetic data, metabolic models of the patient data store 430 may be iteratively trained based on the updated data stored in the patient data store 430. In one embodiment, the GAN-based synthetic data generation techniques discussed above implement two neural networks—a generator neural network that creates synthetic data and a discriminator neural network that distinguishes synthetic data from real data. The generator neural network is trained to generated synthetic data, which the discriminator neural network cannot distinguish from real data.

The metabolic models implemented by the Digital Twin clinical trial simulator 375 analyze hundreds of input features extracted from personal patient data (e.g., BMI, height, weight, visceral fat, bone mass), nutrition data (e.g., food nutrients stored in the nutrition database for millions of food items), glucose trend factors, and derived features. As the number of features encoded into a feature vector increases, the prediction generated by a metabolic model increases in accuracy and complexity, but the complexity of the model increases. Accordingly, the Digital Twin clinical trial simulator 375 removes similar features which are collinear in nature that do not affect the accuracy of the model and determines the importance of the collinear features to the metabolic models. The Digital Twin clinical trial simulator 375 may determine the importance of a feature using any suitable technique including, but not limited to, tree-based models that determine feature importance at a global level, partial dependence plots (PDP), localized models (eg. Lime & Shap) that provide more model explainability and determine feature importance.

The physical experiment generator 950 generates a shortlist of candidate treatment recommendations (from the larger volume of candidate treatments generated by the generator 910) to be validated with physical experiments. The physical experiment generator 950 identifies candidate treatment recommendations to be included on the shortlist based, at least in part, on the effectiveness of the recommendation (as determined by the treatment evaluation module 930), the sufficiency of the biosignal and patient data upon which the recommendation was evaluated (as determined by the treatment evaluation module 930), and the accuracy of the correlations upon which the effectiveness was determined (as determined by the synthetic biosignal generator 940). In some embodiments, the physical experiment generator 950 transmits the shortlist of candidate treatment recommendations to a medical provider, a patient, or a combination thereof via an application on a computing device.

In addition to the efficacy of a candidate treatment recommendation, the physical experiment generator 950 may determine whether the prediction generated by the treatment evaluation module 930 satisfies one or more confidence thresholds. The Digital Twin clinical trial simulator 375 may generate confidence thresholds using the techniques discussed below to capture the uncertainty in the classification accuracy of a prediction. The generated confidence thresholds may be used to quantify the certainty in predictions generated by the Digital Twin clinical trial simulator 375, providing a lower and upper bound and a likelihood assuming a Gaussian distribution of the error. Based on such pre-defined confidence thresholds, the Digital Twin clinical trial simulator 375 may remove or select certain candidate treatment recommendations from consideration regarding the shortlist of candidate treatment recommendations.

The physical experiment generator 950 may additionally implement one or more data analysis techniques to identify the shortlist of candidate treatment recommendations. The physical experiment generator 950 may additionally consider the volume of patient data, biosignal data, and synthetic data upon which a candidate treatment recommendation is validated. The treatment evaluation module 930 may identify a candidate treatment recommendation as effective given the prediction generated by the treatment evaluation module 930, but the physical experiment generator 950 may determine that the patient health management platform 130 did not collect enough data used to generate a reliable prediction (e.g., the volume of data did not satisfy a threshold amount). The physical experiment generator 950 may remove such candidate treatment recommendations from consideration regarding the shortlist of candidate treatment recommendations. Continuing from the example above regarding hypertension reversal, the treatment evaluation module 930 may determine that a candidate treatment recommendation instructing a patient to participate in cardio exercises is an effective recommendation, but the patient management platform 130 has not collected a threshold amount of patient data to reliably analyze the effect of cardio exercises on hypertension reversal. Accordingly, the physical experiment generator 950 excludes the candidate treatment recommendation from the generated shortlist.

If, after the removal of such candidate treatment recommendations, the number of remaining candidate treatment recommendations does not satisfy a threshold amount, the physical experiment generator 950 may communicate instructions for the candidate treatment generator 950 to generate additional candidate treatment recommendations based on a new or updated domain of data and intervention parameters.

Additionally, the physical experiment generator 950 may evaluate patient data 952 based on data sparsity and data collinearity between intervention parameters and aspects of metabolic health and between intervention parameters and a target improvement for a candidate treatment recommendation. If the data sparsity is very high or if the data is imbalanced for the candidate treatment recommendation being evaluated, the physical experiment generator 950 may implement techniques to balance the dataset by doing undersampling or oversampling, before the treatment evaluation module 115 generates an updated evaluation of the candidate treatment recommendation. If the treatment evaluation module 930 determines that the updated evaluation still fails to satisfy the threshold confidence levels discussed above, the physical experiment generator 950 may remove the candidate treatment recommendation from consideration regarding the shortlist of candidate treatment recommendations.

For each shortlisted candidate treatment recommendation, the physical experiment generator 950 may additionally generate instructions for physically testing the candidate treatment recommendation and identify which intervention parameters to analyze to determine the efficacy of the recommendation, for example by defining a clinical trial to evaluate the candidate treatment recommendation. As discussed above, a physical clinical trial is a complex process for evaluating a candidate treatment recommendation on actual patients that considers many variables including, but not limited to, the number of patients to be enrolled in the experiment, the duration of the experiment, the number of intervention parameters, and adjustments to each intervention parameter. Whereas the treatment evaluation model 930 predicts the effectiveness of a candidate treatment recommendation by simulating its effect on a given cohort of patients, the physical experiment generator 950 designs a physical experiment or clinical trial that will be effective for evaluating the candidate treatment recommendation. The effectiveness of the physical experiment or clinical trial is determined based on the likelihood that the results of the experiment will provide insight regarding the effect predicted by the treatment evaluation module 930 at the conclusion of the experiment. For example, if the experiment is poorly designed, the result of the experiment will provide no insight into the effectiveness of a given candidate treatment recommendation The techniques described herein are described with reference to a clinical trial but a person having ordinary skill in the art would appreciate that the techniques described herein could be applied to any type of physical experiment.

Conventionally, clinical trials are designed manually as organizers/scientists weight the competing interests of keeping the trial small enough to be cost-efficient and keeping the trial large enough to observe a measurable effect of the candidate treatment recommendation. In particular, the size of the trial (e.g., the number of patients enrolled in the trial) and the composition of patients enrolled in the trial is a crucial element to consider when designing a clinical trial. As described herein, improving the "effectiveness" of a clinical trial involve weighting these competing interests. A trial with a large-estimated effect size and a large acceptable risk of failure can be kept relatively small. However, if the estimated effect size is too low, a relatively small trial would be ineffective (e.g., the trial would show no measurable impact). Similarly, if the estimated effect size is too small and the acceptable risk is too small, the necessary size of the trial would be too large and, therefore, too expensive to perform.

For each shortlisted candidate treatment recommendation, the physical experiment generator 950 leverages the insights generated by components to the digital twin clinical trial simulator 375 (e.g., the patient cohort generator 920 and the treatment evaluation module 930) to generate an efficient clinical trial (or physical experiment) for evaluating the treatment recommendation. The physical experiment generator 950 identifies requirements of a physical trial for a candidate treatment recommendation based on the evaluation generated by the treatment evaluation module 930 for the candidate treatment recommendation. For candidate treatment recommendations where the treatment evaluation module 930 predicts that a candidate treatment recommendation will satisfy a target outcome of the candidate treatment recommendation, the physical experiment generator 950 may simulate versions of a clinical trial by adjusting one or more trial parameters including, but not limited to, the length/duration of the trial, the number of subjects enrolled in the trial, the composition of patients to be enrolled in the experiment, adjustments to each intervention parameter (also described herein as "interventions"), the size of each intervention, and a range of additional parameters. As described herein, the size of the intervention describes the magnitude of change or adjustment to the intervention parameter. For example, a candidate treatment recommendation that suggests an increase in activity from 4,000 steps to 6,000 is a larger intervention than an increase from 4,000 to 4,500 steps.

For example, a first variation of a clinical trial including 50 patients may be considered ineffective because the effect predicted by the treatment evaluation model 930 is not observable in a statistically meaningful manner, but a second variation of the clinical trial including 100 patients may be considered effective because the predicted effect is observable in a statistically meaningful manner. As another example, a first variation of a clinical trial lasting 2 weeks may be considered ineffective because the effect predicted by the treatment evaluation module 930 is not observable in a statically meaningful manner, but a second variation of the clinical trial lasting one month may be considered effect because the predicted effect is observable in a statistically meaningful manner.

To determine the effectiveness of each variation of the clinical trial, the physical experiment generator 950 predicts the effectiveness of the clinical trial given an assumed acceptable risk of failure. The physical experiment generator 950 may predict the effectiveness of each variation of the clinical trial by performing a statistical analysis including, but not limited to, a power calculation, a Student's T-test, Z-test, Chi-squared test, or any other suitable statistical analysis. The physical experiment generator 950 communicates each variation of the clinical trial to the patient cohort generator 920 and the treatment evaluation module 930. The patient cohort generator 920 generates a test cohort and a control cohort to determine the effectiveness of the variation using the techniques discussed above. The treatment evaluation module 930 simulates a clinical trial of the variation on the test cohort using the techniques discussed above. In one embodiment, the physical experiment generator 950 considers a null hypothesis that the variation of the clinical trial will have no statistically significant impact on the metabolic state of patients. The physical experiment generator 950 determines whether to reject the null hypothesis using any suitable statistical analysis. If the physical experiment generator 950 determines to reject the null hypothesis, the physical experiment generator 950 identifies the variation as a successful clinical trial where changes in the metabolic state of the test cohort (e.g., improvements in their metabolic state) resulted from the adjustments to the intervention parameter prescribed by the candidate treatment recommendation. If the physical experiment generator 950 determines to accept the null hypothesis, the physical experiment generator 950 identifies the variation as an unsuccessful clinical trial where the difference(s) between the test cohort and control cohort were not statistically significant. In another embodiment, the physical experiment generator 950 predicts the likelihood that each variation of the clinical trial will be successful (e.g., changes in the metabolic state of the test resulted from the adjustments to the intervention parameter prescribed by the candidate treatment recommendation). In such embodiments, the treatment evaluation module 930 performs numerous simulations of each variation of the clinical trial and the physical experiment generator 950 compares the number of simulations where the variation was successful to the number of simulations where the variation was unsuccessful.

The acceptable risk of failure may be defined manually be the entity or health professional overseeing the clinical trial. In other embodiments, the acceptable risk of failure may be determined based on past clinical trial designed for a particular entity, designed to affect a target outcome, or a combination thereof. The physical experiment generator 950 selects a variation of the clinical trial that satisfies a threshold effectiveness. Where multiple variations satisfy the threshold effectiveness, the physical experiment generator 950 selects the variation that is most cost efficient (e.g., optimizes duration and population of patients while satisfying the threshold effectiveness).

Additionally, the physical experiment generator 950 additionally identifies patients or types of patients to participate in the trial who may be more sensitive to the intervention parameters adjusted in a candidate treatment recommendation. As discussed above, the patient cohort generator 920 identifies a cohort of patients sensitive to the intervention parameters adjusted by a particular candidate treatment recommendation. In one embodiment, the physical experiment generator 950 recommends that each patient in the identified cohort be included in the clinical trial. In another embodiment, the physical experiment generator 950 identifies the metabolic feature(s) shared across patients in the cohort that causes each patient to be sensitive to the intervention parameter adjusted in the candidate treatment recommendation. For example, all patients in a given cohort may have a BMI above 28 and a fasting plasma glucose above 120. The physical experiment generator 950 generates instructions for the trial supervisor to include patients in the clinical trial who have the identified metabolic feature. In such embodiments, the physical experiment generator 950 need not have a complete understanding of the relationship between the effect of the candidate treatment recommendation and the identified metabolic feature but need only recognize a correlation between the identified metabolic feature and the effect of the candidate treatment recommendation. The physical experiment generator 950 identifies shared metabolic features from a patient cohort based on simulations performed by the treatment evaluation module 930 and identifying cohorts of patients with improved responses to the candidate treatment recommendation.

In some embodiments the identified factor is a binary feature (e.g., it is present or not present), but in other embodiment is a range of values (e.g., a diastolic blood pressure within a predetermined range). In the latter embodiments, the physical experiment generator 950 may determine more flexible eligibility requirements for patients to be to be enrolled in a clinical trial. For a given metabolic feature, patients in the test cohort whom the treatment evaluation module 930 predicted an improvement in their metabolic state as a result of the candidate treatment recommendation may experience a range of measurements for the identified metabolic feature. For patients in the test cohort who experienced a measurement beyond that range, the treatment evaluation module 930 may predict that their metabolic state will not improve or will deteriorate as a result of the candidate treatment recommendation. For example, when testing the effect of apple cider vinegar consumption on the post prandial glucose response of a rice-based meal, the treatment evaluation module 930 may predict the most significant improvements in patients with a body mass index (BMI) below 26. Thus, the physical experiment generator 950 generates instructions for the trial supervisor to include patients with a BMI below 26.

In some embodiments, the physical experiment generator 950 identifies multiple metabolic features that caused patients in the cohort to be sensitive to a candidate treatment recommendation, for example BMI, muscle mass, triglyceride level, etc. the physical experiment generator 950 leverages the digital twin of each patient in the test cohort to determine the significance of the effect that each metabolic feature has on patients in the test cohort. In some embodiments, the physical experiment generator 950 determines the significance of the effect of a metabolic feature based on the fraction of patients in the test cohort whose digital twins showed increased susceptibility to the candidate treatment recommendation, where the metabolic feature was optimized for susceptibility to the candidate treatment recommendation and the fraction of patients showing increased susceptibility, where the metabolic feature was optimized for insensitivity to the candidate treatment recommendation.

The physical experiment generator 950 ranks each identified metabolic feature based on the determined significance that each metabolic feature has on patients in the test cohort. Additionally, the physical experiment generator 950 generates instructions for the trial supervisor to consider patients for the clinical trial in order of most significant metabolic features to least significant.

In some embodiments, the physical experiment generator 950 generates a recommended cohort of patients to be enrolled in the clinical trial. In other embodiments, the physical experiment generator 950 receives a list of patients enrolled in the clinical trial. From the patients enrolled in a clinical trial for a given candidate treatment recommendation, the physical experiment generator 950 additionally defines a control cohort and a test cohort for the clinical trial (based on the cohorts generated by the patient cohort generator 920). The physical experiment generator 950 may verify that the distribution of the generated control cohort and test cohort are similar (as discussed above) before instructing each actual patient in the test cohort to adhere to the candidate treatment recommendation. As each patient in the test cohort adheres to the candidate treatment recommendation, the patient health management platform 130 further validates the efficacy of the candidate treatment recommendation based on wearable sensor data and lab test data describing the patient's true metabolic state.

More information regarding the implementation of the patient health management platform 130 to monitor a patient's adherence to a treatment recommendation can be found in U.S. patent application Ser. No. 16/993,177, filed on Aug. 13, 2020, which is incorporated by reference herein in its entirety.

Figure 10:
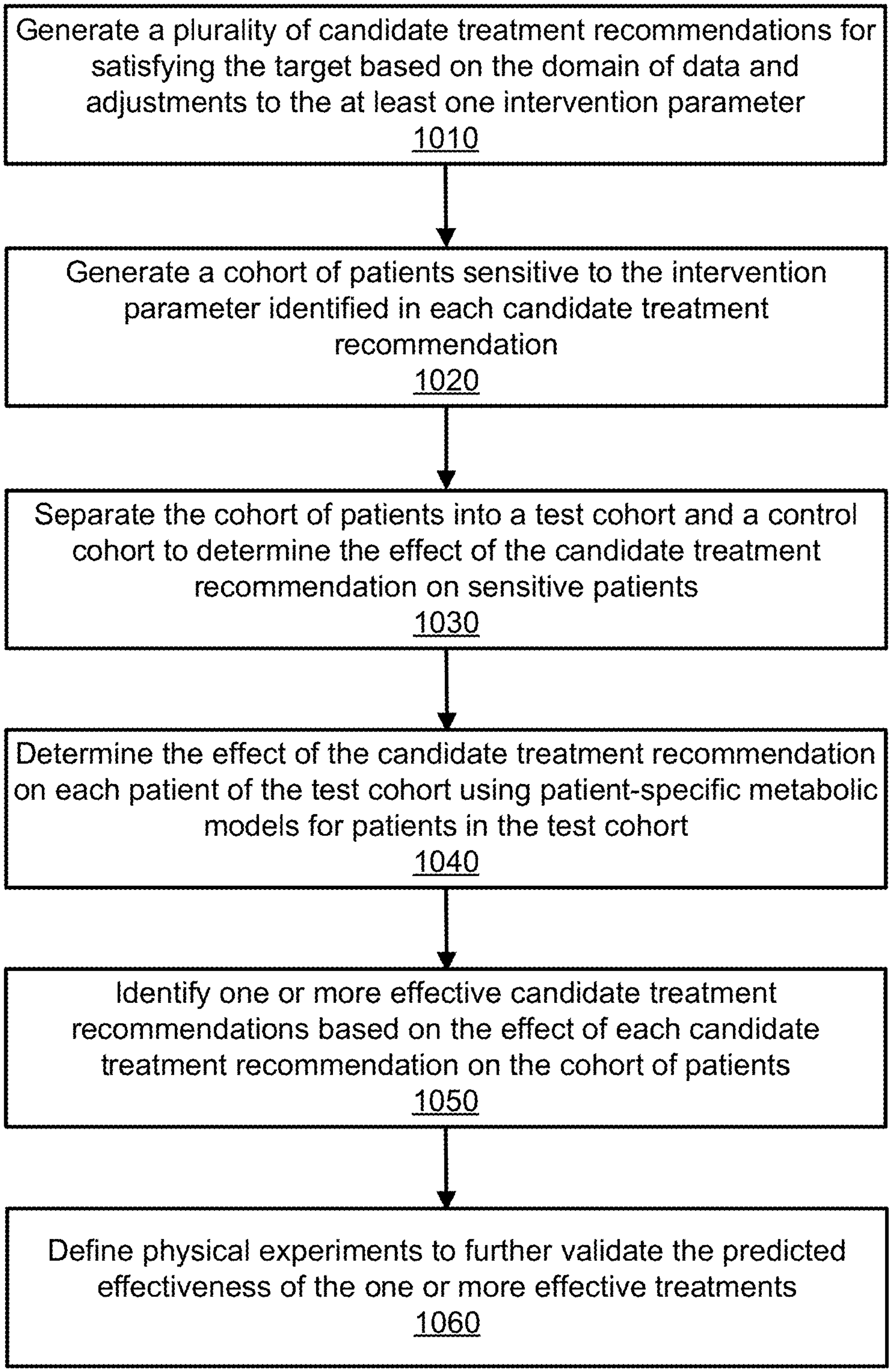
FIG. 10 is a flowchart illustrating a process for identifying one or more effective candidate treatment recommendations for validating by a physical experiment, according to one embodiment.

FIG. 10 is a flowchart illustrating a process for identifying one or more effective candidate treatment recommendations for validating by a physical experiment, according to one embodiment. As discussed above, the Digital Twin clinical trial simulator 375 receives a target for improving metabolic health in patients, at least one intervention parameter to be adjusted in various candidate treatment recommendations, and a domain of data for evaluating candidate treatment recommendations (e.g., from a provider). The target represents an improvement in an aspect of metabolic health and an intervention parameter represents an adjustment to be made in a patient's lifestyle, activity, sleep, or nutrition to affect that improvement. Based on the various combinations of intervention parameters and possible adjustments to each of those intervention parameters, the Digital Twin clinical trial simulator 375 generates 1010 a candidate treatment recommendation for satisfying the target improvement in metabolic health. In some embodiments, the Digital Twin clinical trial simulator 375 generates 1010 a plurality of candidate treatment recommendations and repeats the steps described herein for each candidate treatment recommendation.

To evaluate each candidate treatment recommendation, the Digital Twin clinical trial simulator 375 generates 1020 a cohort of patients sensitive to the intervention parameter identified in the candidate treatment recommendation. The Digital Twin clinical trial simulator 375 identifies patients sensitive to the intervention parameter based on each patient's historical metabolic profile and previously analyzed correlations between adjustments to intervention parameters and their metabolic state. Accordingly, sensitive patients are those whose metabolic state is expected to be impacted by adjustments to a particular intervention parameter. The Digital Twin clinical trial simulator 375 separates 1030 the cohort of patients into a test cohort and a control cohort to determine the effect of candidate treatment recommendations on sensitive patients.

Using the control cohort and the test cohort, the Digital Twin clinical trial simulator 375 evaluates the candidate treatment recommendation. The Digital Twin clinical trial simulator 375 determines 1040 the effect of the candidate treatment recommendation on each patient of the control cohort using patient-specific metabolic models for the patient. The Digital Twin clinical trial simulator 375 inputs a feature vector representation of the candidate treatment recommendation into each patient's metabolic models comprising their digital twin. Accordingly, the Digital Twin clinical trial simulator 375 (via the digital twin module 450) generates a holistic prediction of the impact of the candidate treatment recommendation on the patient's metabolic health. Based on whether the impact satisfies the target improvement in metabolic health, the Digital Twin clinical trial simulator 375 may determine the effectiveness of the candidate treatment recommendation.

The Digital Twin clinical trial simulator 375 identifies 1050 one or more effective candidate treatment recommendations based on the effect of each candidate treatment recommendation on the cohort of patients and aggregates these identified recommendations to a shortlist. The Digital Twin clinical trial simulator 375 defines 1060 physical experiments to be carried out to further confirm or validate the effectiveness of the one or more effective treatments in a laboratory or research environment. For each shortlisted candidate treatment recommendation, the Digital Twin clinical trial simulator 375 may additionally define instructions for patients to adhere to the treatment recommendation, a test cohort of patients, a control cohort of patients, and intervention parameters and data to be monitored by a provider, researcher, or other third party to physically evaluate the effect of the candidate treatment recommendation.

Figure 11:
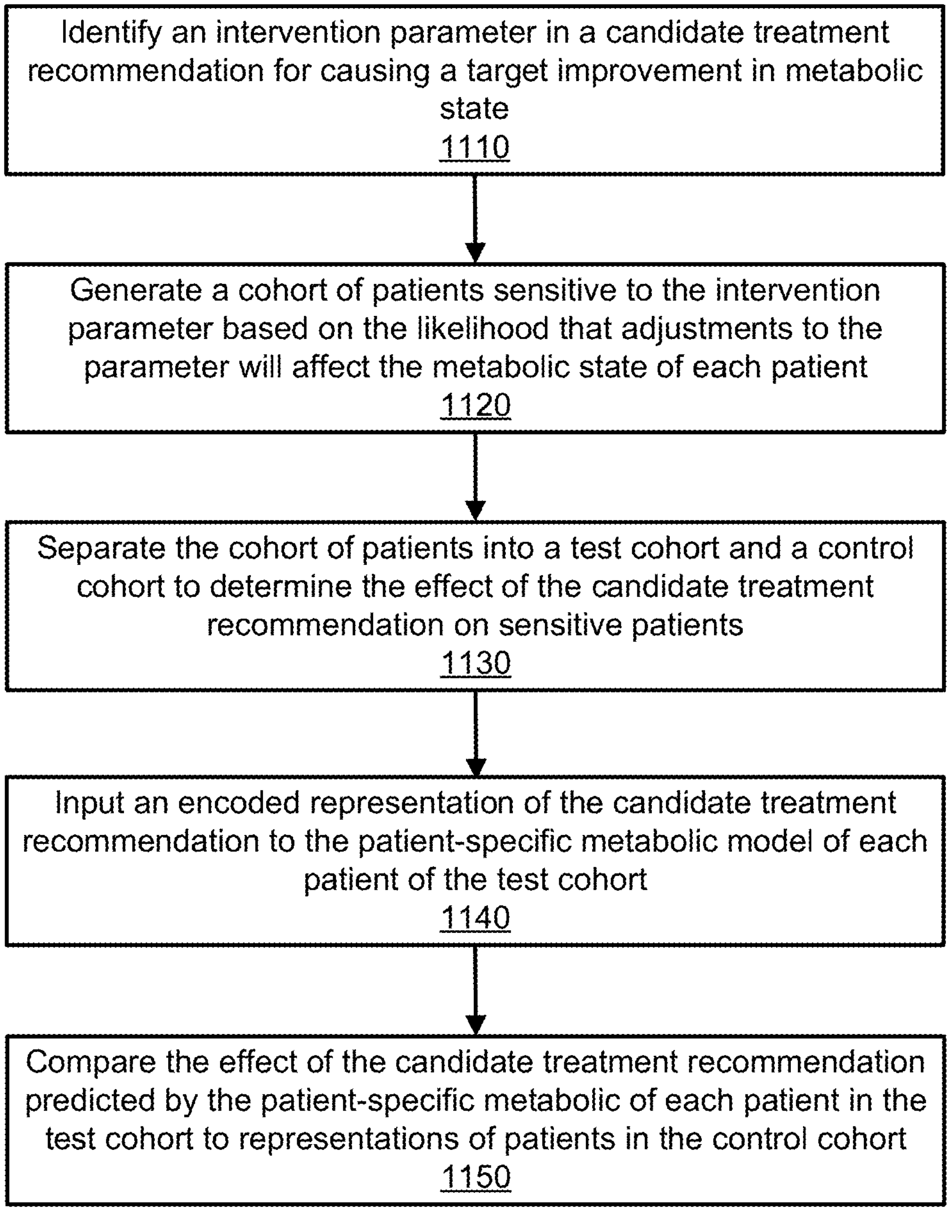
FIG. 11 is a flowchart illustrating a process for generating a cohort of patients, according to one embodiment.

FIG. 11 is a flowchart illustrating a process for generating a cohort of patients, according to one embodiment. Continuing from step 1020, the Digital Twin clinical trial simulator 375 identifies 1110 an intervention parameter in a candidate treatment recommendation for causing a target improvement in a metabolic state of a patient. As described above, the candidate treatment recommendation comprises instructions for adjusting the intervention parameter, which causes the target improvement in the patient's metabolic state. In some embodiments, the candidate treatment recommendation may comprise instructions for adjusting multiple intervention parameters to accomplish the target improvement. In such embodiments, the Digital Twin clinical trial simulator 375 repeats the steps described herein for each intervention parameter.

The Digital Twin clinical trial simulator 375 generates 1120 a cohort of patients sensitive to the intervention parameter from a population of patients. The sensitivity of a patient representing the likelihood that adjustments to the intervention parameter will affect the metabolic state of the patient. Where adjustments to the intervention parameter will have threshold effect on the metabolic state of a patient (either an improvement or deterioration), the patient is labeled as "sensitive" to the intervention parameter. Where adjustments to the intervention parameter will not have a threshold effect on the metabolic state of a patient, the patient is labeled as "insensitive" to the intervention parameter. Accordingly, the Digital Twin clinical trial simulator 375 generates the cohort of patients by analyzing correlations between changes in the metabolic state of each patient of the population and adjustments to the intervention parameter.

The Digital Twin clinical trial simulator 375 separates 1130 the cohort of patients into a test cohort and a control cohort to determine the effect of the candidate treatment recommendation on sensitive patients (e.g., the patients in the generated cohort). The test cohort and the control cohort comprise distinct subsets of patients in the generated cohort, but the Digital Twin clinical trial simulator 375 separates the cohort of patients such that each of the test cohort and the control cohort such that the distribution of patients in the test cohort matches the distribution of patients in the control cohort based on age, ethnicity, gender, metabolic health, overall health or any other suitable factor. The Digital Twin clinical trial simulator 375 determines the effect of the candidate treatment recommendation on each patient of the test cohort using the patient-specific metabolic models for the patient.

The Digital Twin clinical trial simulator 375 inputs 1140 an encoded representation of the instructions of the treatment recommendation to the patient-specific metabolic model(s) (e.g., their Digital Twin) of each patient of the test cohort to predict an effect of the treatment recommendation on the patient. The Digital Twin clinical trial simulator 375 compares 1150 the effect of the candidate treatment recommendation predicted by the effect of each patient in the test cohort to representation of patients in the control cohort. The Digital Twin clinical trial simulator 375 may determine a representative effect of the candidate treatment recommendation on patients in the test cohort by aggregating (or averaging) the effects predicted by patient-specific metabolic models of each patient in the test cohort. The Digital Twin clinical trial simulator 375 may compare the representative effect to a representative metabolic state determined from the unaffected metabolic states of patients in the control cohort.

Figure 12:
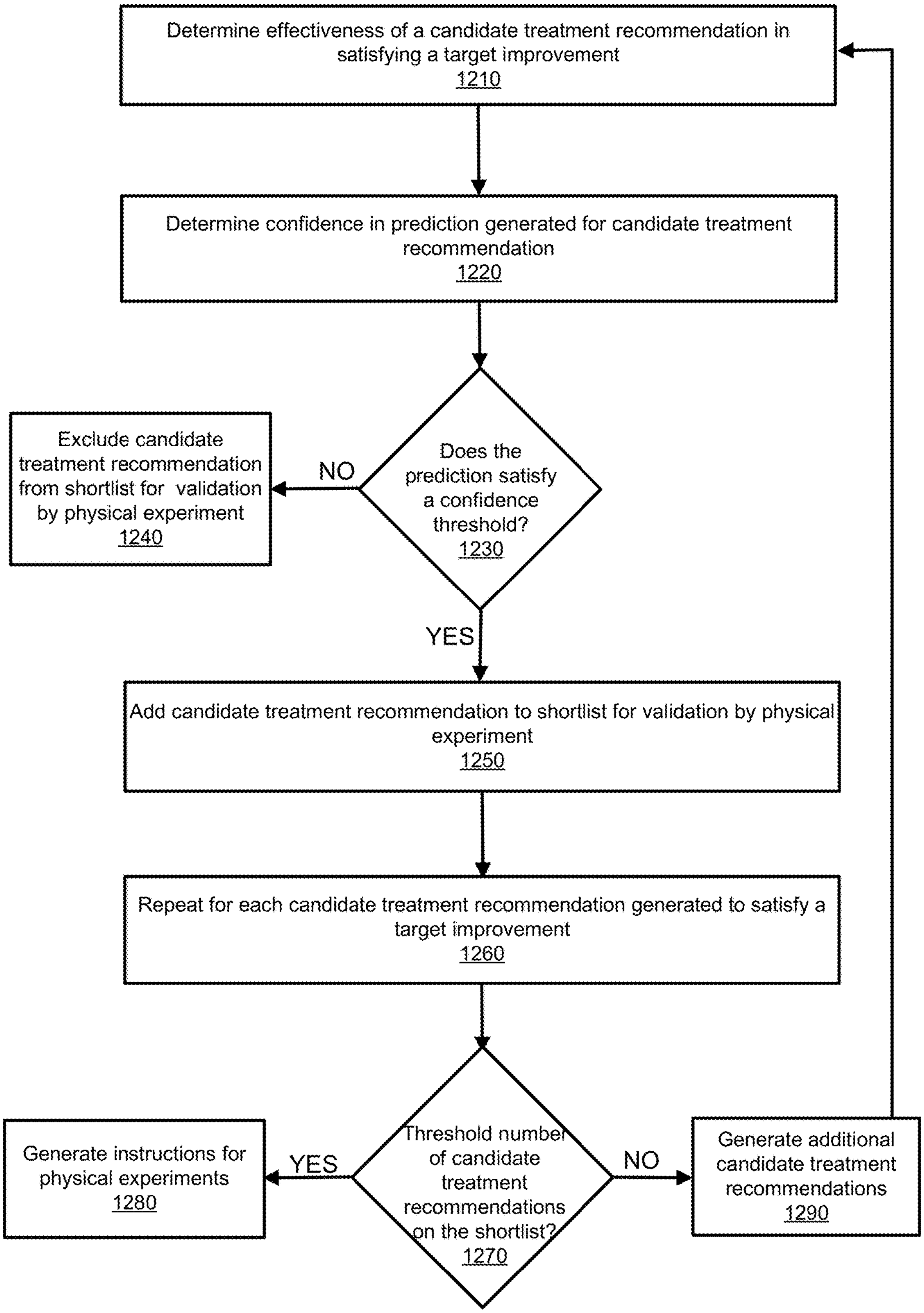
FIG. 12 is a flowchart illustrating a process for generating a shortlist of candidate treatment recommendations, according to one embodiment.

FIG. 12 is a flowchart illustrating a process for generating a shortlist of candidate treatment recommendations, according to one embodiment. Continuing from step 1050 of FIG. 10, the Digital Twin clinical trial simulator 375 determines 1210 the effectiveness of a candidate treatment recommendation for satisfying a target improvement in metabolic health based on the impact of the candidate treatment recommendation predicted by the digital twins of patients in the test cohort. The Digital Twin clinical trial simulator 375 reduces the number of candidate treatment recommendations to a subset of the most effective candidate treatment recommendations or most accurate predictions, which are included in a shortlist for validation by physical experiments.

Accordingly, the Digital Twin clinical trial simulator 375 determines 1120 a confidence in the predictions generated for the candidate treatment recommendation by the digital twins of the test cohort. If the determined confidence does not satisfy 1130 a confidence threshold, the Digital Twin clinical trial simulator excludes 1140 the candidate treatment recommendation from being added to the shortlist. If it does satisfy 1140 the confidence threshold, the Digital Twin clinical trial simulator 375 adds 1150 the candidate treatment recommendation to the shortlist of recommendations to be validated in a physical experiment. The Digital Twin clinical trial simulator 375 may additionally consider the sparsity and collinearity between intervention parameters and the target improvement of candidate treatment recommendation, although not shown. If the data sparsity, data collinearity, or both do not satisfy a threshold condition, the Digital Twin clinical trial simulator excludes the candidate treatment recommendation from being added to the shortlist. If they do satisfy the threshold conditions, the Digital Twin clinical trial simulator adds the candidate treatment recommendation to the shortlist. The Digital Twin clinical trial simulator 375 repeats 1160 the process discussed above for each candidate treatment recommendation generated in step 1020 of FIG. 10.

After filtering candidate treatment recommendations based on prediction confidence, data collinearity, data sparsity, or a combination thereof, the Digital Twin clinical trial simulator 375 determines 1170 whether a threshold number of candidate treatment recommendations have been added to the shortlist. If the threshold number is satisfied, the Digital Twin clinical trial simulator 375 generates 1180 instructions for performing and managing physical experiments to validate each shortlisted candidate treatment recommendation. If the threshold number is not satisfied, the Digital Twin clinical trial simulator 375 generates 1190 additional candidate treatment recommendations and repeats the process described above to determine whether to add the additional recommendations to the shortlist.

Figure 13:
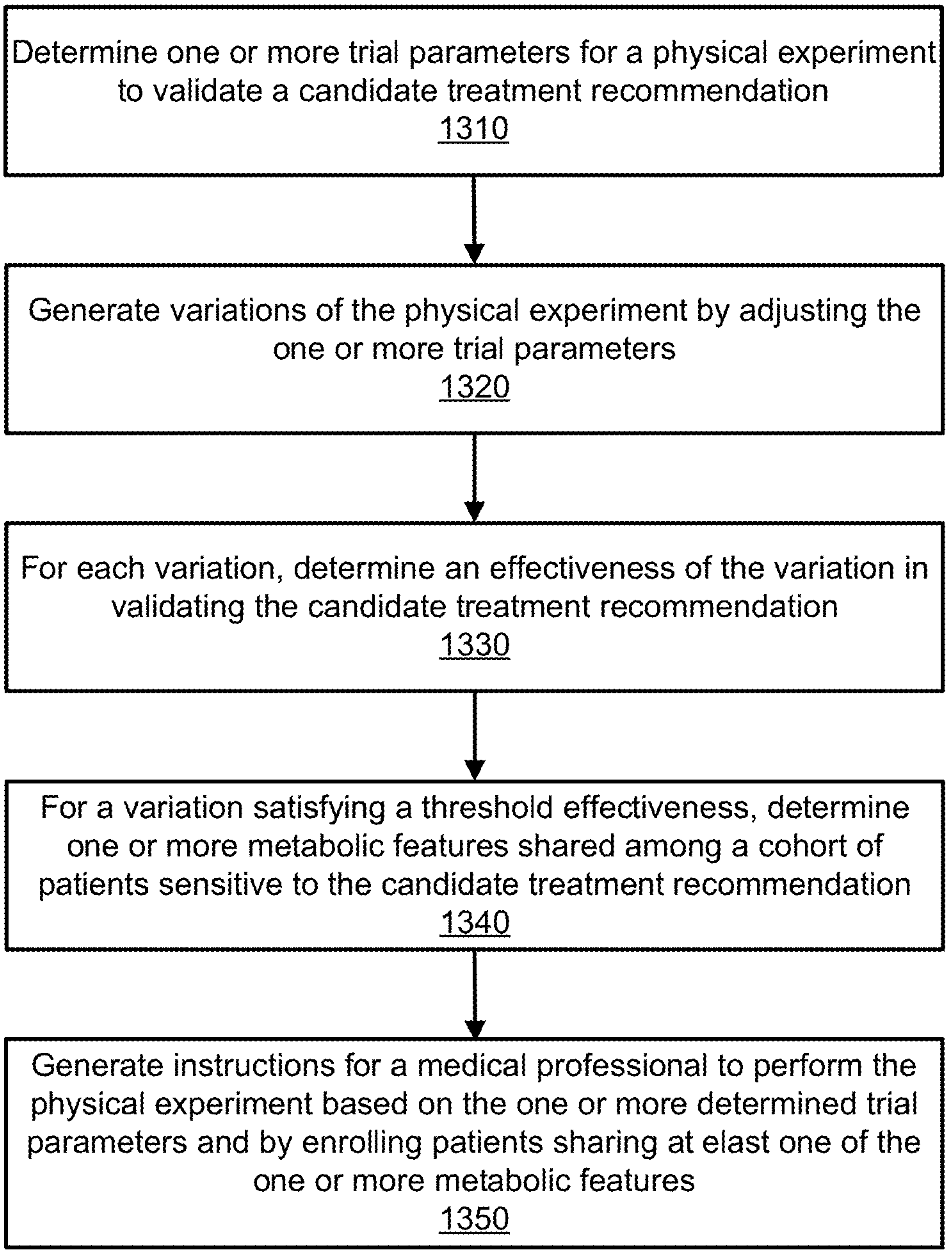
FIG. 13 is a flowchart illustrating a process for designing a physical experiment to validate a shortlisted candidate treatment recommendation, according to one embodiment.

FIG. 13 is a flowchart illustrating a process for designing a physical experiment to validate a shortlisted candidate treatment recommendation, according to one embodiment. Continuing from step 1280 illustrated in FIG. 12, the Digital Twin clinical trial simulator 375 determines 1310 one or more trial parameters for a physical experiment to validate a candidate treatment recommendation. The Digital Twin clinical trial simulator 375 determines the trial parameters to balance the cost of the experiment and the likelihood that the experiment will be effective in evaluating the candidate treatment recommendation. In particular, the Digital Twin clinical trial simulator 375 considers the duration of the experiment, the population of patients enrolled in the experiment, and the composition of patients enrolled in the experiment. The Digital Twin clinical trial simulator 375 generates 1320 variations of the physical experiment by adjusting the one or more trial parameters. For example, the Digital Twin clinical trial simulator 385 may generate physical experiments of varying durations and with varying numbers of enrolled patients.

The Digital Twin clinical trial simulator 375 determines 1330 an effectiveness of each variation of the physical experiment. The effectiveness describes a likelihood that the experiment will provide insight regarding the effect of the candidate treatment recommendation on a metabolic state. The Digital Twin clinical trial simulator 375 selects the variation of the physical experiment that satisfies a threshold effectiveness in a most cost-efficient manner (e.g., optimizes for population of patients and duration). For the selected variation, the Digital Twin clinical trial simulator 375 determines 1340 one or more metabolic features shared among a cohort of patients sensitive to the candidate treatment recommendation, for example the cohort of patients used to simulate the effect of the candidate treatment recommendation. The Digital Twin clinical trial simulator 375 generates 1350 instructions for a medical professional or trial supervisor to perform the selected variation of the physical experiment by adjusting the trial parameters according to the selected variation and enrolling patients sharing at least one of the one or more metabolic features.

Figure 14:
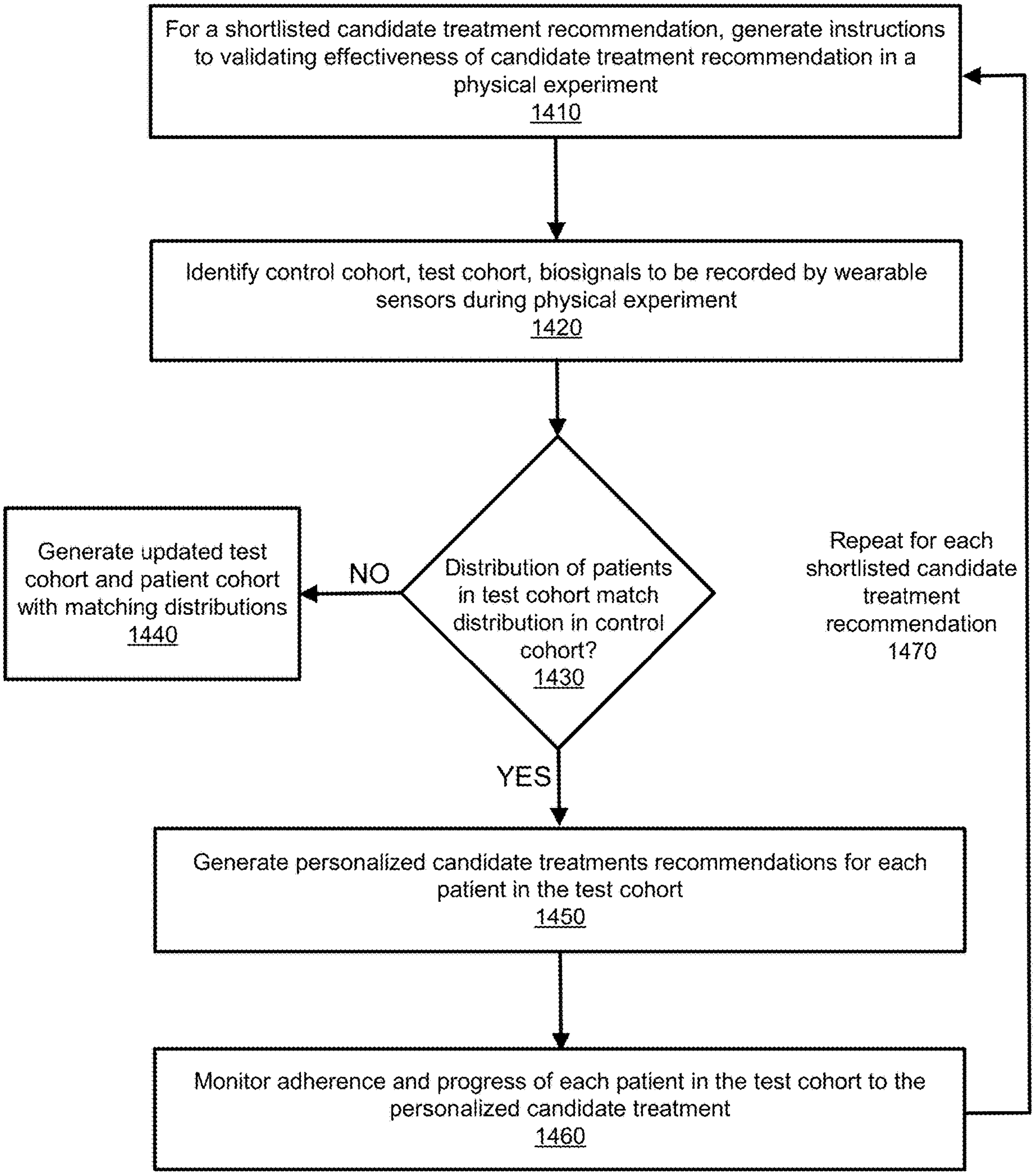
FIG. 14 is a flowchart illustrating a process for generating instructions for performing a physical experiment to validate a shortlisted candidate treatment recommendation, according to one embodiment.

FIG. 14 is a flowchart illustrating a process for implementing a physical experiment to validate a shortlisted candidate treatment recommendation, according to one embodiment. Continuing from step 1280 illustrated in FIG. 13, the Digital Twin clinical trial simulator 375 generates 1410 instructions for validating the effectiveness of a shortlisted candidate treatment recommendation in a physical experiment. The generated instructions may be procedures to be followed by providers or third parties supervising the experiments (e.g., patient data to be measured, duration of the experiment) or a recommendation to be adhered to by patients in a test cohort (e.g., nutrition plans, activity plans). The Digital Twin clinical trial simulator identifies 1420 a control cohort of patients for the experiment, a test cohort of patients for the experiment, and biosignals to be recorded over the duration of the experiment for evaluating the effectiveness of the candidate treatment recommendation.

With regards to the test and control cohorts, the Digital Twin clinical trial simulator 375 determines 1430 whether the distribution of patients in the test cohort matches the distribution of patients in the control cohort based on age, ethnicity, gender, metabolic health, overall health or any other suitable factor. If the distributions do not match within a threshold level of difference, the Digital Twin clinical trial simulator 375 generates 1440 an updated test cohort and patient cohort with more closely matched distributions. If the distributions do match within a threshold level of difference, the Digital Twin clinical trial simulator 375 generates 1450 transmits the candidate treatment recommendations to each patient in the test cohort and monitors 1460 the adherence and progress of each patient in the test cohort to the personalized candidate treatment. The process described above is repeated 1470 to generate instructions for each candidate treatment recommendation included in the shortlist.

Figure 15:
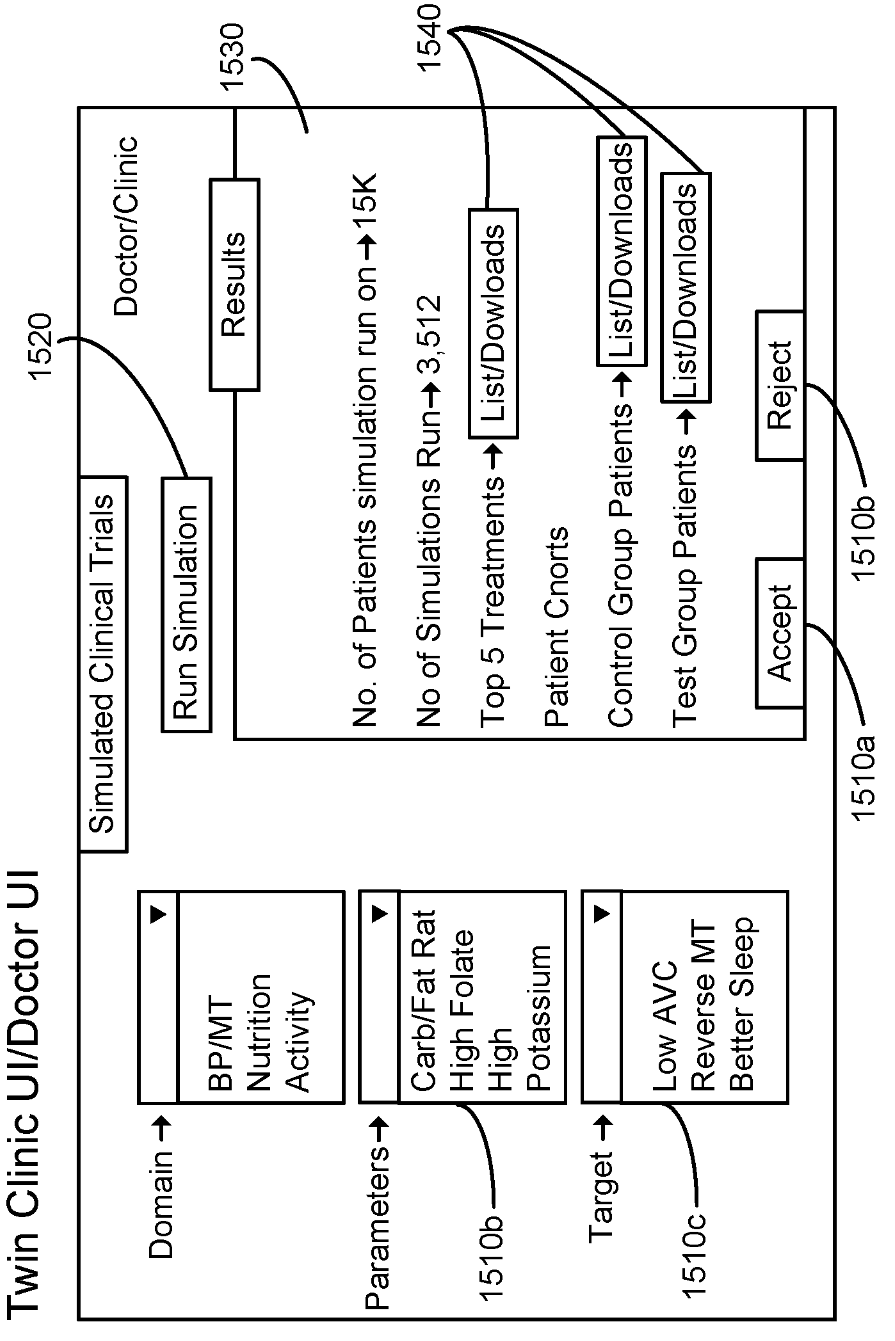
FIG. 15 illustrates an example graphical user interface for simulating a clinical trial, according to one embodiment.

FIG. 15 illustrates an example graphical user interface for simulating a clinical trial, according to one embodiment. In the illustrated embodiment of FIG. 15, the interface 1500 displays selectable elements 1510*a*, 1510*b*, and 1510*c* that allow a provider to define the "domain," "intervention parameters," and "target" of candidate treatment recommendations (each of which are described above). As illustrated in FIG. 15, the domain includes blood pressure measurements, nutrition data, and activity data. The adjustable intervention parameters include carbohydrate intake, high folate consumption, and high potassium consumption. The target improvements of the candidate treatment recommendation include low Postprandial Glucose AUC counts (e.g., a rise in blood glucose following consumption of a meal), reverse hypertension, and improved sleep patterns. Each of the selectable elements 1510 may allow a user to provide a typographic input or to select inputs from a drop-down menu. After defining the scope of the candidate recommendation treatments using the selectable elements 1510, a provider may interact with the selectable element 1520 to initiate a simulation of a clinical trial, consistent with the techniques discussed above with reference to FIGS. 9-14.

Upon conclusion of the simulations, a graphical display panel 1530 displays information describing the number of patients in the test cohort, the number of simulations performed (e.g., the number of candidate treatment recommendations evaluated by the Digital Twin clinical trial simulator 375), the shortlist of the candidate treatment recommendations identified by the physical experiment generator 950, a combination thereof. The graphical display panel 1430 may additionally provide selectable options 1540 to view or download the shortlist of treatments for physical experimentation, the record of patients in the control cohort, and the record of patients in the test cohort. Each of these downloadable options may be communicated to a third-party along with instructions for performing physical experiments to validate the shortlisted candidate treatment recommendations and evaluating the results.

A provider may select the selectable graphical element 1550 to accept the results of the simulation (e.g., the shortlisted candidate treatment recommendation) or graphical element 1550*b* to reject the results and revise the scope of the simulation (e.g., adjust selectable elements 1510*a*, 1510*b*, and 1510*c*).

Figure 16A:
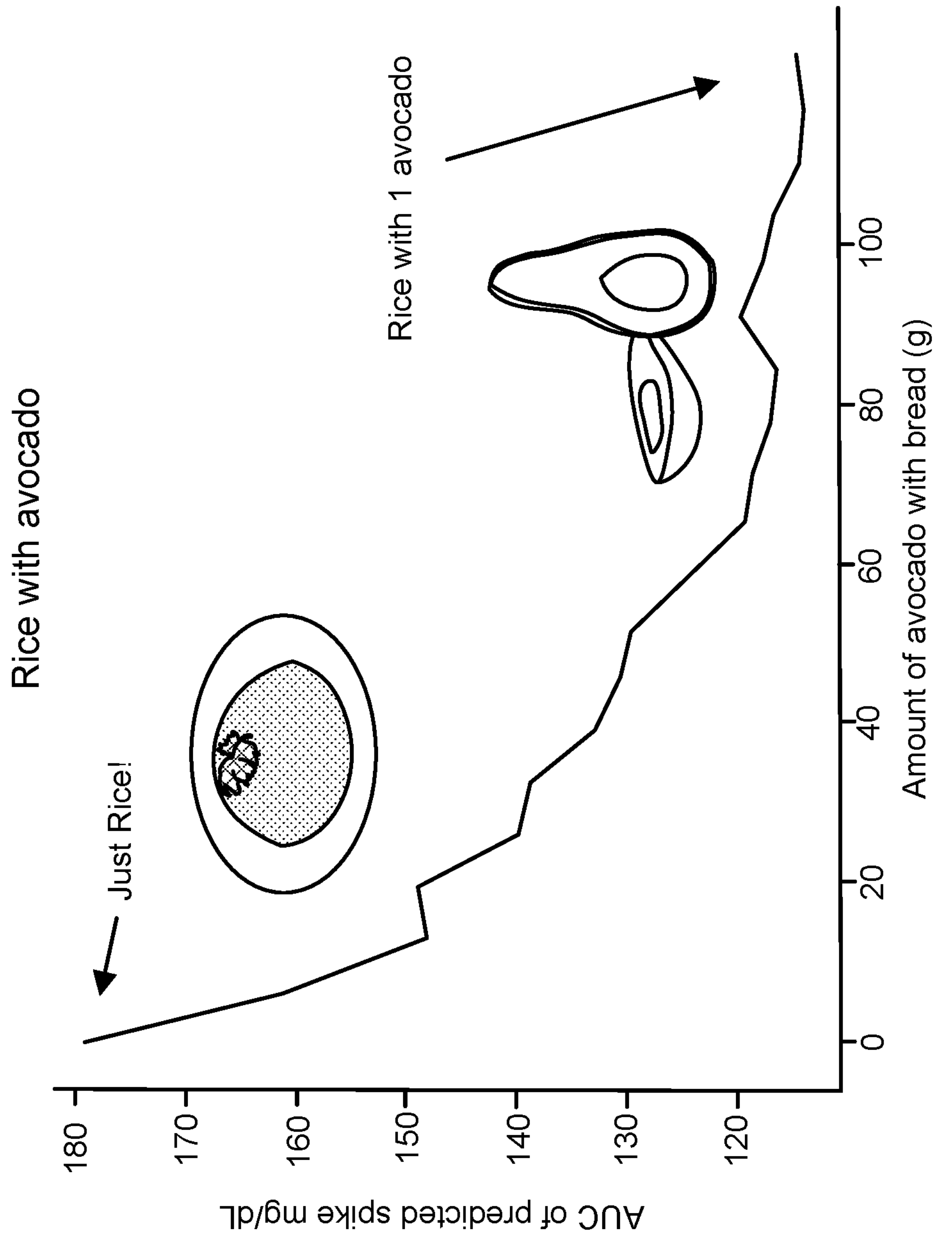
FIGS. 16A-B are diagrams for analyzing patient data for validating the effectiveness of a candidate treatment recommendation, according to one embodiment.
Figure 16B:
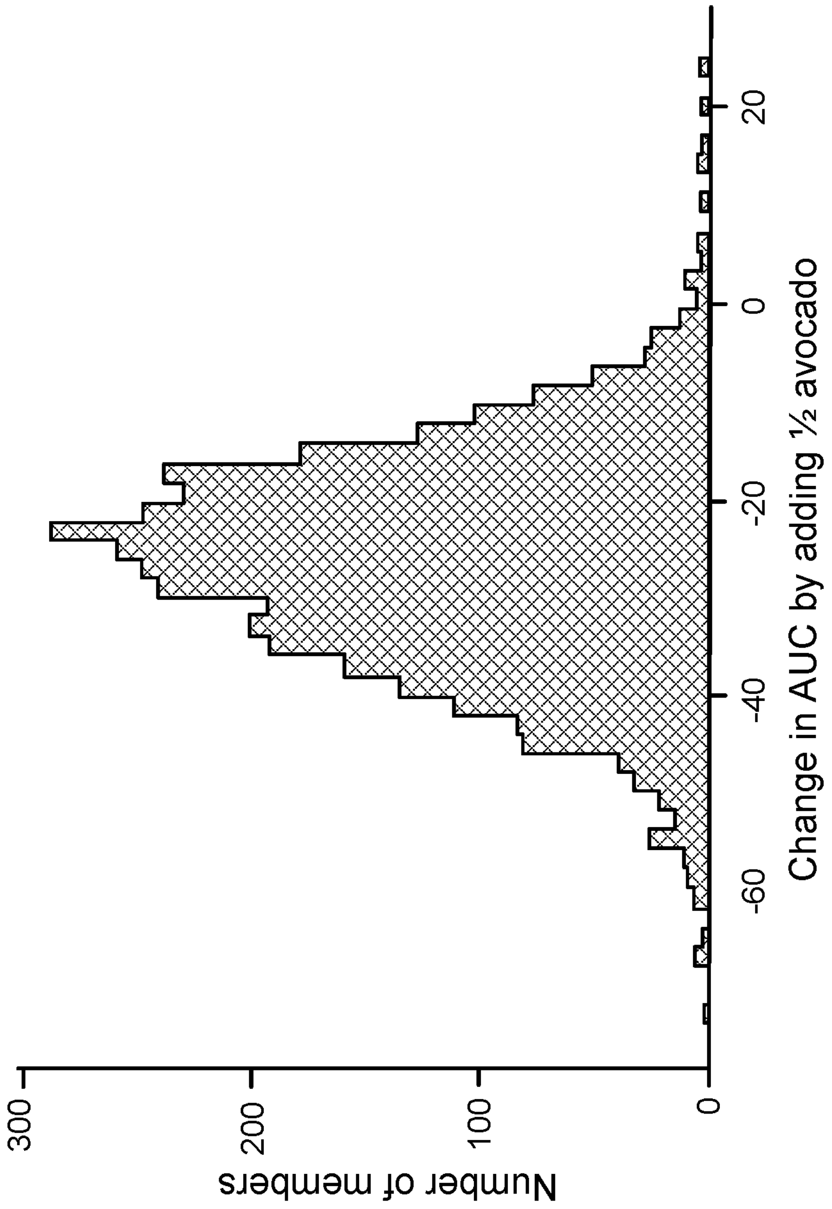

FIGS. 16A-B are diagrams for analyzing patient data for validating the effectiveness of a candidate treatment recommendation, according to one embodiment. FIG. 16A is a graph illustrating the effect of varied avocado consumption (a nutritional intervention parameter specified in a candidate treatment recommendation) on a patient's predicted glucose spike. In the illustrated graph, the predicted glucose spike decreased when an amount of avocado was added to the simulated meal of a cup of rice. With zero avocado added (left of the graph), the AUC of the spike was 180 mg/dL*hr. With 120 g of avocado added to the simulated meal, the predicted AUC of the spike was 110 mg/dL*hr, a decrease of 70 mg/dL*hr.

FIG. 16B illustrates a histogram of patient responses to a nutrition-based candidate treatment recommendation prescribing increased avocado consumption. The glucose spike resulting from the ingestion of one cup of rice was predicted for each member in the twin program in addition to the glucose spike resulting from the ingestion of one cup of rice and half an avocado. The difference between the two glucose spikes was determine. As illustrated in FIG. 16A, on average, one cup of rice with half an avocado resulted in a 20-30 mg/dL*hour smaller spike than just the one cup of rice. Patients who are predicted to have a greater difference in spike between the two meals could be identified and added to a test cohort for a physical experiment to validate the nutrition-based candidate treatment recommendation.

VI. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of the above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:

generating a plurality of candidate treatment recommendations for causing a target improvement in metabolic state, wherein each of the candidate treatment recommendations comprises an intervention parameter and instructions for adjusting the intervention parameter to cause the target improvement; for each of the candidate treatment recommendations, generating, from a population of patients, a cohort of patients sensitive to adjustments to the intervention parameter, the sensitivity of a patient representing a likelihood that adjustments to the intervention parameter will affect the metabolic state of the patient;

for each patient of the cohort of patients, predicting effects of the candidate treatment recommendation on a metabolic state of the patient by inputting the candidate treatment recommendation to a digital twin of the patient, wherein:

the digital twin comprises a plurality of patient-specific metabolic models trained to predict effects of candidate treatment recommendations on metabolic states based on a training dataset of previously adjusted intervention parameters and effects of each previously adjusted intervention parameter on the metabolic state, each patient-specific metabolic model of the plurality models an aspect of a metabolic state of the patient, and predicting the effect of the candidate treatment recommendation on the metabolic state of the patient further comprises:

identifying a primary metabolic model from the plurality of patient-specific metabolic models based on the intervention parameter of the candidate treatment recommendation, wherein the intervention parameter directly affects an output of the primary metabolic model;

identifying one or more secondary metabolic models from the plurality of patient-specific metabolic models, wherein the output of the primary metabolic model directly affects an output of each secondary model;

inputting the candidate treatment recommendation to the primary metabolic model to predict an effect of the candidate treatment recommendation on the aspect of the metabolic state corresponding to the primary model; and inputting the candidate treatment recommendation and the effect predicted by the primary model to each secondary model to predict effects of the candidate treatment recommendation on aspects of the metabolic state of the patient corresponding to the secondary model;

identifying, from the plurality of candidate treatment recommendations, a shortlist comprising one or more effective treatments identified based on their effects predicted by the plurality of patient-specific metabolic models of the digital twin; and displaying the shortlist of candidate treatment recommendations to a patient or medical provider via an application on a computing device.

2. The method of claim 1, wherein each candidate treatment recommendation of the plurality of candidate treatment recommendations represents a distinct combination of intervention parameters of the population of intervention parameters.

3. The method of claim 1, further comprising:

responsive to receiving a domain for the plurality of candidate treatment recommendations, identifying patient data recorded for the population of patients within the domain, wherein the domain represents types of patient data to be measured for evaluating each candidate treatment; and generating the plurality of candidate treatment recommendations based on patient data identified within the domain.

4. The method of claim 1, further comprising:

defining a population of intervention parameters, wherein each intervention parameter of the population represents a feature of the candidate treatment to be input to the patient-specific metabolic model; and generating the plurality of candidate treatment recommendations based on the population of intervention parameters, wherein each of the plurality of candidate treatment recommendations represents a distinct combination of intervention parameters of the population of intervention parameters.

5. The method of claim 1, wherein generating the cohort of patients comprises:

accessing patient data for the population of patients, the patient data comprising labels describing the sensitivity of each patient of the population of patients to the intervention parameter; and generating the cohort of patients based on patients sensitive to the intervention parameter in the candidate treatment recommendation based on the accessed patient data.

6. The method of claim 5, wherein assigning the label describing the sensitivity of a patient to the intervention parameter to the patient comprises:

determining historical changes in a metabolic state of the patient caused by previous adjustments to the intervention parameter; and assigning the patient to either a first subset of patients sensitive to the intervention parameter or a second subset of patients insensitive to the intervention parameter based on the historical changes.

7. The method of claim 1, wherein generating the cohort of patients comprises:

identifying, from the population of patients, a subset of patients whose metabolic state is below a threshold metabolic state; and generating the cohort of patients from the subset of patients.

8. The method of claim 1, wherein generating the cohort of patients comprises:

determining a long-term effect of adjustments to the intervention parameter on each patient of the population of patients based on historical changes in the metabolic state of the patient; and generating the cohort of patients based on the long-term effect of adjustments to the intervention parameter determined for each patient of the population of patients.

9. The method of claim 1, wherein the candidate treatment recommendation comprises instructions for adjusting a plurality of intervention parameters and generating the cohort of patients comprises:

for each patient of the population of patients, determining a sensitivity of each patient to each intervention parameter of the plurality; and determining an overall sensitivity of the patient to the candidate treatment recommendation based on the sensitivity of the patient to each intervention parameter of the plurality; and generating the cohort of patients based on the overall sensitivity of each patient of the population of patients.

10. The method of claim 1, wherein generating the cohort of patients comprises:

categorizing the population of patients into categories of patients with a shared metabolic state;

for each category of patients, predicting an effect of the candidate treatment recommendation on each patient of the category by inputting the candidate treatment recommendation to a patient-specific metabolic model of the patient; and determining an overall sensitivity of the category of patients to the candidate treatment recommendation based on the predicted effect of the candidate treatment recommendation on each patient of the cohort; and determining a category of patients most sensitive to the candidate treatment recommendation based on a comparison of the overall sensitivity of each category of patients; and generating the cohort of patients based on the category of patients most sensitive to the candidate treatment recommendation.

11. The method of claim 1, further comprising:

separating the cohort of patients into a control cohort and a test cohort, wherein the candidate treatment recommendation is input to the patient-specific metabolic model for each patient of the test cohort; and determining the overall effect of the candidate treatment recommendation on the cohort based on a comparison of the effect of the candidate treatment recommendation predicted by the patient-specific metabolic model of each patient in the test cohort to representations of metabolic states of patients in the control cohort.

12. The method of claim 1, wherein the primary metabolic model is identified based on:

an effect of the intervention parameter on outputs of each patient-specific metabolic model of the digital twin; or features of metabolic health measured to validate the effect of the intervention parameter.

13. The method of claim 1, wherein predicting the effect of the candidate treatment recommendation on the metabolic state of the patient further comprises:

predicting an effect of the candidate treatment recommendation on the metabolic state of each patient of the cohort of patients;

determining a change in metabolic state of each patient of the cohort of patients based on a comparison of the predicted effect and a current metabolic state of the patient; and determining an aggregate effect of the candidate treatment recommendation on the cohort of patients based on an average change between the predicted effect and current metabolic state of patients in the cohort of patients.

14. The method of claim 1, wherein predicting the effect of the candidate treatment recommendation on the metabolic state of the patient further comprises:

encoding a feature vector representation of the candidate treatment recommendation; and inputting the feature vector representation into each of the patient-specific metabolic models of the digital twin for each patient of the cohort.

15. The method of claim 1, further comprising:

determining a strength of correlation between an intervention parameter adjusted for the candidate treatment recommendation and a feature of patient data;

responsive to determining an amount of data collected for the feature to be below a threshold amount, generating synthetic data for the feature; and labeling the synthetic data with a first label and the collected data with a second label.

16. The method of claim 1, wherein identifying the shortlist of candidate treatment recommendations comprises:

identifying candidate treatment recommendations based on the effectiveness of the candidate treatment recommendation, the effectiveness characterized by comparing the predicted effect of each candidate treatment recommendation on the cohort of patients to a threshold improvement; and ranking each candidate treatment recommendation of the shortlist based on the effectiveness of the candidate treatment recommendation.

17. The method of claim 1, wherein the shortlist of candidate treatment recommendations is identified based on:

an amount of biosignal and patient data collected for evaluating the intervention parameters of the candidate treatment recommendation; and data sparsity or data collinearity between intervention parameters of the candidate treatment recommendation and the target improvement of the candidate treatment recommendation; and an accuracy of correlations between the intervention parameters and the predicted effect of the candidate treatment recommendation on the metabolic state of the patient.

18. The method of claim 1, further comprising:

identifying candidate treatment recommendations that cause a threshold improvement in metabolic state by comparing the predicted changes in metabolic states of the cohort of patients to a threshold improvement, wherein the predicted changes in metabolic states represent the effectiveness of a candidate treatment recommendation;

extracting intervention parameters adjusted in the one or more effective treatments of the candidate treatment recommendations; and generating an aggregate treatment recommendation comprising adjustments to one or more of the extracted intervention parameters to cause the target improvement.

19. The method of claim 1, further comprising:

generating, for each of the one or more candidate treatment recommendations on the shortlist, instructions for performing a physical experiment to validate the performance of the candidate treatment recommendation.

20. A non-transitory computer readable medium storing instructions encoded thereon that, when executed by a processor, cause the one or more processors to:

generate a plurality of candidate treatment recommendations for causing a target improvement in metabolic state, wherein each of the candidate treatment recommendations comprises one or more intervention parameters and instructions for adjusting the one or more intervention parameters to cause the target improvement;

for each of the candidate treatment recommendations, identify, from a population of patients, a cohort of patients, wherein each patient of the cohort is sensitive to adjustments to the one or more intervention parameters, the sensitivity of a patient representing a likelihood that adjustments to the one or more intervention parameters will affect the metabolic state of the patient;

for each patient of the cohort of patients, predict effects of the candidate treatment recommendation on a metabolic state of the patient by inputting the candidate treatment recommendation to a digital twin of the patient, wherein:

the digital twin comprises a plurality of patient-specific metabolic models trained to predict effects of candidate treatment recommendations on metabolic states based on a training dataset of previously adjusted intervention parameters and effects of each previously adjusted intervention parameter on the metabolic state, each patient-specific metabolic model of the plurality models an aspect of a metabolic state of the patient, and predicting the effect of the candidate treatment recommendation on the metabolic state of the patient further comprises:

identifying a primary metabolic model from the plurality of patient specific metabolic models based on the one or more intervention parameters of the candidate treatment recommendation, wherein the one or more intervention parameters directly affect an output of the primary metabolic model;

identifying one or more secondary metabolic models from the plurality of patient-specific metabolic models, wherein the output of the primary metabolic model directly affects an output of each secondary model;

inputting the candidate treatment recommendation to the primary metabolic model to predict an effect of the candidate treatment recommendation on the aspect of the metabolic state corresponding to the primary model; and inputting the candidate treatment recommendation and the effect predicted by the primary model to each secondary model to predict effects of the candidate treatment recommendation on aspects of the metabolic state of the patient corresponding to the secondary model;

identify, from the plurality of candidate treatment recommendations, a shortlist comprising one or more effective treatments identified based on their effects predicted by the plurality of patient-specific metabolic models of the digital twin; and generate, for each of the one or more effective treatments, instructions for performing a physical experiment to validate the performance of the effective treatment.

21. A system comprising:

one or more processors; and a non-transitory computer readable medium storing instructions encoded thereon that, when executed by the one or more processors, cause the one or more processors to:

generate a plurality of candidate treatment recommendations for causing a target improvement in metabolic state, wherein each of the candidate treatment recommendations comprises one or more intervention parameters and instructions for adjusting the one or more intervention parameters to cause the target improvement;

for each of the candidate treatment recommendations, identify, from a population of patients, a cohort of patients, wherein each patient of the cohort is sensitive to adjustments to the one or more intervention parameters, the sensitivity of a patient representing a likelihood that adjustments to the one or more intervention parameters will affect the metabolic state of the patient;

for each patient of the cohort of patients, predict effects of the candidate treatment recommendation on a metabolic state of the patient by inputting the candidate treatment recommendation to a digital twin of the patient, wherein:

the digital twin comprises a plurality of patient-specific metabolic models trained to predict effects of candidate treatment recommendations on metabolic states based on a training dataset of previously adjusted intervention parameters and effects of each previously adjusted intervention parameter on the metabolic state, each patient-specific metabolic model of the plurality models an aspect of a metabolic state of the patient, and predicting the effect of the candidate treatment recommendation on the metabolic state of the patient further comprises:

identifying a primary metabolic model from the plurality of patient-specific metabolic models based on the one or more intervention parameters of the candidate treatment recommendation, wherein the one or more intervention parameters directly affect an output of the primary metabolic model;

identifying one or more secondary metabolic models from the plurality of patient-specific metabolic models, wherein the output of the primary metabolic model directly affects an output of each secondary model;

inputting the candidate treatment recommendation to the primary metabolic model to predict an effect of the candidate treatment recommendation on the aspect of the metabolic state corresponding to the primary model; and inputting the candidate treatment recommendation and the effect predicted by the primary model to each secondary model to predict effects of the candidate treatment recommendation on aspects of the metabolic state of the patient corresponding to the secondary model;

identify, from the plurality of candidate treatment recommendations, a shortlist comprising one or more effective treatments identified based on their effects predicted by the plurality of patient-specific metabolic models of the digital twin; and generate, for each of the one or more effective treatments, instructions for performing a physical experiment to validate the performance of the effective treatment.

* * * * *